(12) United States Patent
Takahashi

(10) Patent No.: US 10,711,033 B2
(45) Date of Patent: *Jul. 14, 2020

(54) BRANCHED CHAIN-CONTAINING AROMATIC COMPOUND

(71) Applicant: AJINOMOTO CO., INC., Tokyo (JP)

(72) Inventor: Daisuke Takahashi, Yokkaichi (JP)

(73) Assignee: AJINOMOTO CO., INC., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/274,463

(22) Filed: Sep. 23, 2016

(65) Prior Publication Data

US 2017/0008922 A1    Jan. 12, 2017

Related U.S. Application Data

(62) Division of application No. 14/013,590, filed on Aug. 29, 2013, now Pat. No. 9,499,579, which is a division of application No. 13/220,841, filed on Aug. 30, 2011, now Pat. No. 8,546,534.

(60) Provisional application No. 61/378,170, filed on Aug. 30, 2010.

(30) Foreign Application Priority Data

Aug. 30, 2010 (JP) .................................. 2010-192961

(51) Int. Cl.

| C07C 43/225 | (2006.01) |
| C07K 1/06 | (2006.01) |
| C07C 43/23 | (2006.01) |
| C07C 235/42 | (2006.01) |
| C07K 5/093 | (2006.01) |
| C07K 5/113 | (2006.01) |
| C07K 7/06 | (2006.01) |
| C07C 41/09 | (2006.01) |
| C07C 209/08 | (2006.01) |
| C07C 217/58 | (2006.01) |
| C07C 231/14 | (2006.01) |
| C07C 233/25 | (2006.01) |
| C07K 5/068 | (2006.01) |
| C07K 5/078 | (2006.01) |
| C07K 5/097 | (2006.01) |
| C07K 5/103 | (2006.01) |

(52) U.S. Cl.
CPC .............. *C07K 1/066* (2013.01); *C07C 41/09* (2013.01); *C07C 43/225* (2013.01); *C07C 43/23* (2013.01); *C07C 209/08* (2013.01); *C07C 217/58* (2013.01); *C07C 231/14* (2013.01); *C07C 233/25* (2013.01); *C07C 235/42* (2013.01); *C07K 1/062* (2013.01); *C07K 5/06086* (2013.01); *C07K 5/06165* (2013.01); *C07K 5/0819* (2013.01); *C07K 5/0821* (2013.01); *C07K 5/1008* (2013.01); *C07K 5/1021* (2013.01); *C07K 7/06* (2013.01); *C07C 2603/18* (2017.05)

(58) Field of Classification Search
None
See application file for complete search history.

(56) References Cited

U.S. PATENT DOCUMENTS

| 5,712,367 A | 1/1998 | Bernard et al. |
| 2004/0214989 A1 | 10/2004 | Chiba et al. |
| 2007/0066799 A1 | 3/2007 | Chiba et al. |
| 2009/0299103 A1 | 12/2009 | Chiba et al. |
| 2010/0029904 A1 | 2/2010 | Chiba et al. |
| 2010/0184952 A1 | 7/2010 | Takahashi |
| 2010/0249374 A1 | 9/2010 | Takahashi |
| 2014/0213761 A1 | 7/2014 | Takahashi |

FOREIGN PATENT DOCUMENTS

| CN | 1699404 A | 11/2005 |
| CN | 101277921 A | 10/2008 |
| CN | 101405240 A | 4/2009 |
| CN | 101463072 A | 6/2009 |
| JP | 2579699 | 7/1996 |
| JP | 2000-044493 | 2/2000 |
| JP | 2004-059509 | 2/2004 |
| JP | 2004-067555 | 3/2004 |
| JP | 2006-015283 | 1/2006 |
| JP | 2010-106084 | 5/2012 |
| WO | WO 00/31120 A2 | 6/2000 |
| WO | 2003/018188 | 3/2003 |
| WO | 2006/104166 | 10/2006 |
| WO | 2007/034812 | 3/2007 |
| WO | 2007/122847 | 11/2007 |

(Continued)

OTHER PUBLICATIONS

CAS RN 1226814-95-4 (entered into STN Jun. 2, 2010) (Year: 2010).*

Office Action dated Aug. 18, 2015 in Japanese Patent Application No. 2012-531896.

Yoshimitsu Sagara, et al., "Brightly Tricolored Mechanochromic Luminescence from a Single-Luminophore Liquid Crystal: Reversible Writing and Erasing of Images" Angewandte Chemie International Edition, vol. 50, 2011, pp. 9128-9132.

(Continued)

*Primary Examiner* — Craig D Ricci
(74) *Attorney, Agent, or Firm* — Oblon, McClelland, Maier & Neustadt, L.L.P.

(57) ABSTRACT

The present invention provides a particular branched chain-containing aromatic compound. The branched chain-containing aromatic compound of the present invention is easily-soluble in isopropyl acetate superior in liquid-separation operability, and can be used for a production method of peptide and the like, which provides a final product simply by extraction separation, without crystallization and isolation of each intermediate in each step.

1 Claim, No Drawings

(56) References Cited

FOREIGN PATENT DOCUMENTS

| WO | 2009/014176 A1 | 1/2009 |
| WO | 2009/014177 A1 | 1/2009 |
| WO | 2010/113939 A1 | 10/2010 |

European Search Report dated Jul. 2, 2015, in European Patent Application No. 11821809.8 filed Aug. 30, 2011.
CAS RN 1226814-93-2 (published May 13, 2010).
Scott et al. (concise Encyclopedia Biochemistry and Molecular Biology, pp. 491-493, $3^{rd}$ edition, 1997).
Bull. Chem. Soc. Japan vol. 74 (2001) pp. 733-738.
Combined Chinese Office Action and Search Report dated Mar. 27, 2018 in Patent Application No. 201610569960.9, received Apr. 26, 2018 (with English translation of Categories of Cited Documents), 8 pages.

\* cited by examiner

BRANCHED CHAIN-CONTAINING AROMATIC COMPOUND

CROSS REFERENCES TO RELATED APPLICATIONS

This application is a divisional application of U.S. patent application Ser. No. 14/013,590, filed on Aug. 29, 2013, which is a divisional application of U.S. patent application Ser. No. 13/220,841, filed on Aug. 30, 2011, and claims priority to U.S. Provisional Patent Application No. 61/378,170, filed on Aug. 30, 2010, and Japanese Patent Application No. 2010-192961, filed on Aug. 30, 2010.

TECHNICAL FIELD

The present invention relates to an aromatic compound containing a particular branched chain. The present invention further relates to a protecting reagent containing the compound or an adduct thereof. The present invention also relates to a production method of peptide by using the compound, and further relates to an organic synthesis method including the production method of the peptide.

BACKGROUND ART

The production methods of peptide are generally divided into solid phase methods and liquid phase methods. The solid phase methods are advantageous since isolation and purification after reaction can be performed by only washing resin. However, they are associated with problems in that the reaction is essentially that of heterogeneous phases, reaction agents and reagents need to be used in excess to compensate for the low reactivity, and tracing of reaction and analysis of reaction product supported by carrier are difficult. On the other hand, the liquid phase method is advantage since it shows good reactivity, and intermediate peptide can be purified by extraction and washing, isolation and the like after condensation reaction. However, the method is associated with problems since the production step is complicated due to an extraction and washing step with a nonpolar organic solvent and an acidic or basic aqueous solution to remove residual reagents and/or byproducts in each step of coupling reaction and deprotection, and/or an isolation and purification step such as crystallization and the like, and the like.

In recent years, approaches to improve the problems of the aforementioned two methods have been ongoing.

Patent document 1 and non-patent document 1 each disclose a method using a 3,4,5-tris(n-octadecyloxy)benzyl alcohol type compound as a protecting reagent of carboxyl group and the like. Patent documents 2-4 each disclose a 3,5-di(docosyloxy)benzyl alcohol type compound, a 2,4-di(docosyloxy)benzyl alcohol type compound, a trityl type compound and the like as protecting reagents. Using these protecting reagents, the reaction can be performed in a homogeneous liquid phase, a precipitate can be produced by changing the solvent composition after the reaction, which can be isolated and purified by filtration and washing alone. However, use of these protecting reagents is associated with problems in that a reaction solvent evaporation step for precipitation is required, a long time is necessary for a precipitate filtration step, and these protecting reagents are insoluble or slightly-soluble in acetate ester or toluene. Therefore, the methods disclosed in the above-mentioned documents are not entirely industrially universal methods.

Patent document 5 introduces an example of a peptide synthesis reaction using a 3,4,5-tris(n-octadecyloxy)benzyl alcohol type compound as a protecting reagent. However, the document only discloses an example of a specific layer-separating separation of organic solvents under dilute conditions, and this example is not entirely an industrially universal method.

DOCUMENT LIST

Patent Documents patent document 1: JP-A-2000-44493
patent document 2: WO2006/104166
patent document 3: WO2007/034812
patent document 4: WO2007/122847
patent document 5: WO2003/018188

Non-Patent Document non-patent document 1: Bull. Chem. Soc. Jpn 74, 733-738 (2001)

SUMMARY OF THE INVENTION

Problems to be Solved by the Invention

The problem of the present invention is to provide a novel compound which is easily-soluble in isopropyl acetate superior in liquid-separating operability, and usable for a production method of peptide and the like which leads to a final product simply by extraction separation without crystallization and isolation of each intermediate in each step (one-pot synthesis method).

Means of Solving the Problems

The present inventors have conducted intensive studies and found that the aforementioned problems can be solved by a particular branched chain-containing aromatic compound, which resulted in the completion of the present invention. The present invention includes the following embodiments.

A branched chain-containing aromatic compound represented by the formula (I):

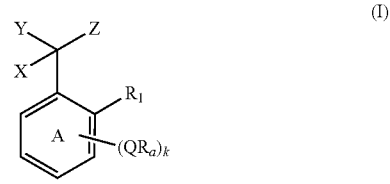

(I)

wherein
Q in the number of k are each a single bond, or —O—, —S—, —C(=O)O—, —C(=O)NH— or —NH—;
$R_a$ in the number of k are each independently an organic group having at least one aliphatic hydrocarbon group having one or more branched chains, a total number of the branched chain of not less than 3 and a total carbon number of not less than 14 and not more than 300;
k is an integer of 1-4;
$R_1$ is a hydrogen atom or, when Z is a group represented by the following formula (a), it optionally shows a single bond together with $R_2$ to form a fluorene ring together with ring B; ring A optionally further has, in addition to $R_1$, $QR_a$ in the number of k, and C(X)(Y)Z, substituent(s) selected from the group consisting of a halogen atom, a $C_{3-6}$ alkyl group optionally substituted by one or more halogen atoms, and a $C_{1-6}$ alkoxy group optionally substituted by one or more halogen atoms;

X is a hydrogen atom or a phenyl group;

Y is a hydroxyl group or an —NHR group (R is a hydrogen atom, an alkyl group or an aralkyl group); and Z is a hydrogen atom or a group represented by the formula (a):

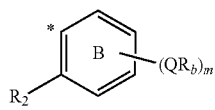

(a)

wherein * shows a bonding position;

m is an integer of 0-4;

Q in the number of m are as defined above;

$R_b$ in the number of m are each independently an organic group having at least one aliphatic hydrocarbon group having one or more branched chains, a total number of the branched chain of not less than 3 and a total carbon number of not less than 14 and not more than 300;

$R_2$ is a hydrogen atom, or optionally shows a single bond together with $R_1$ to form a fluorene ring together with ring A; and ring B optionally further has, in addition to $QR_b$ in the number of m, and $R_2$, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms);

the organic group having at least one aliphatic hydrocarbon group having one or more branched chains, a total number of the branched chain of not less than 3 and a total carbon number of not less than 14 and not more than 300 for the aforementioned $R_a$ and $R_b$ is a group having 3 or more the same or different divalent groups, which is represented by the formula (b):

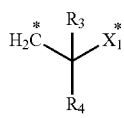

(b)

wherein * shows a bonding position with the adjacent atom;

$R_3$ and $R_4$ are each independently a hydrogen atom or a $C_{1-4}$ alkyl group;

$X_1$ is a single bond, a $C_{1-4}$ alkylene group or an oxygen atom, provided that $R_3$ and $R_4$ are not hydrogen atoms at the same time.

[2] The branched chain-containing aromatic compound of the aforementioned [1], wherein the organic group having at least one aliphatic hydrocarbon group having one or more branched chains, a total number of the branched chain of not less than 3 and a total carbon number of not less than 14 and not more than 300 for the aforementioned $R_a$ and $R_b$ is a group represented by the formula (c):

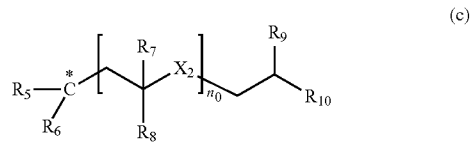

(c)

wherein * shows a bonding position to Q;

$R_5$ and $R_6$ are both hydrogen atoms, or taken together to show =O;

$n_0$ is an integer of 2-40;

$R_7$ and $R_8$ in the number of no are each independently a hydrogen atom or a $C_{1-4}$ alkyl group;

$X_2$ in the number of $n_0$ are each independently a single bond or a $C_{1-4}$ alkylene group; and $R_9$ is a hydrogen atom or a $C_{1-4}$ alkyl group;

$R_{10}$ is a $C_{1-4}$ alkyl group or the formula (I'):

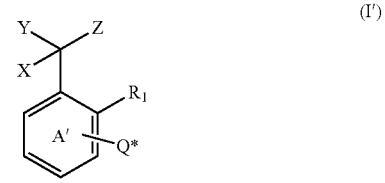

(I')

wherein * shows a bonding position;

other symbols are as defined above, and ring A' optionally has, in addition to $R_1$, Q, and C(X)(Y)Z, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms, provided that $R_7$ and $R_8$ are not hydrogen atoms at the same time, and when $n_0$ is 2, $R_9$ is a $C_{1-4}$ alkyl group.

[3] The branched chain-containing aromatic compound of the aforementioned [2], wherein, in the aforementioned formula (c), $R_5$ and $R_6$ are both hydrogen atoms;

$R_7$ and $R_8$ in the number of $n_0$ are each independently a hydrogen atom, a methyl group or an ethyl group;

$X_2$ in the number of $n_0$ are each independently a single bond, a methylene group or an ethylene group; and $R_9$ is a hydrogen atom, a methyl group or an ethyl group.

[4] The branched chain-containing aromatic compound of the aforementioned [1], wherein the organic group having at least one aliphatic hydrocarbon group having one or more branched chains, a total number of the branched chain of not less than 3 and a total carbon number of not less than 14 and not more than 300 for the aforementioned $R_a$ and $R_b$ is a group represented by the formula (d):

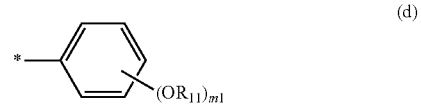

(d)

wherein * shows a bonding position to Q;

$OR_{11}$ in the number of $m_1$ is a hydroxyl group substituted by a group represented by the formula (c'):

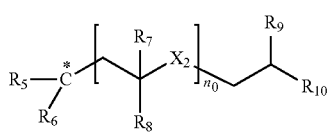
(c')

wherein * shows a bonding position to O;
$R_5$ and $R_6$ are both hydrogen atoms, or taken together show =O;
$n_0$ is an integer of 2-40;
$R_7$ and $R_8$ in the number of $n_0$ are each independently a hydrogen atom or a $C_{1-4}$ alkyl group;
$X_2$ in the number of $n_0$ are each independently a single bond or a $C_{1-4}$ alkylene group; and
$R_9$ is a hydrogen atom or a $C_{1-4}$ alkyl group;
$R_{10}$ is a $C_{1-4}$ alkyl group or a group represented by the formula (I'):

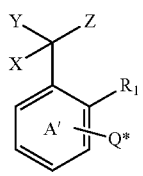
(I')

wherein * shows a bonding position;
other symbols are as defined above, and ring A' optionally has, in addition to $R_1$, Q, and C(X)(Y)Z, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms,
provided that $R_7$ and $R_8$ are not hydrogen atoms at the same time, and when $n_0$ is 2, $R_9$ is a $C_{1-4}$ alkyl group; and $m_1$ is an integer of 1-3.
[5] The branched chain-containing aromatic compound of the aforementioned [1], wherein the organic group having at least one aliphatic hydrocarbon group having one or more branched chains, a total number of the branched chain of not less than 3 and a total carbon number of not less than 14 and not more than 300 for the aforementioned $R_a$ and $R_b$ is a group represented by the formula (e):

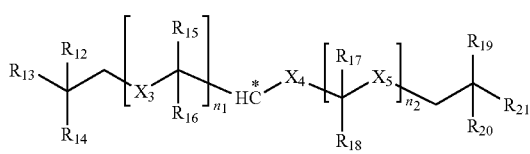
(e)

wherein * shows a bonding position to Q;
$n_1$ is an integer of 1-10;
$n_2$ is an integer of 1-10;
$R_{15}$ and $R_{16}$ in the number of $n_1$ are each independently a hydrogen atom or a $C_{1-4}$ alkyl group;
$X_3$ in the number of $n_1$ is a single bond or a $C_{1-4}$ alkylene group;
$R_{17}$ and $R_{18}$ in the number of $n_2$ are each independently a hydrogen atom or a $C_{1-4}$ alkyl group;

$X_5$ in the number of $n_2$ is a single bond or a $C_{1-4}$ alkylene group;
$X_4$ is a single bond or a $C_{1-4}$ alkylene group; and
$R_{12}$, $R_{13}$, $R_{14}$, $R_{19}$, $R_{20}$ and $R_{21}$ are each independently a hydrogen atom or a $C_{1-4}$ alkyl group,
provided when $R_{15}$ and $R_{16}$, and/or $R_{17}$ and $R_{18}$ are not hydrogen atoms at the same time, and when $n_1+n_2$ is 2, then two or more of $R_{12}$, $R_{13}$ and $R_{14}$ are each independently a $C_{1-4}$ alkyl group, or two or more of $R_{19}$, $R_{20}$ and $R_{21}$ are each independently a $C_{1-4}$ alkyl group.
[6] The branched chain-containing aromatic compound of the aforementioned [5], wherein, in the aforementioned formula (e),
$n_1$ is an integer of 1-5;
$n_2$ is an integer of 1-5;
$R_{15}$ and $R_{16}$ in the number of $n_1$ are each independently a hydrogen atom, a methyl group or an ethyl group;
$X_3$ in the number of $n_1$ is a single bond, a methylene group or an ethylene group;
$R_{17}$ and $R_{18}$ in the number of $n_2$ are each independently a hydrogen atom, a methyl group or an ethyl group;
$X_5$ in the number of $n_2$ is a single bond, a methylene group or an ethylene group; and
$X_4$ is a single bond, a methylene group or an ethylene group.
[7] The branched chain-containing aromatic compound of the aforementioned [6], wherein, in the aforementioned formula (e),
$R_{15}$ and $R_{16}$ in the number of $n_1$ are each independently a hydrogen atom or a methyl group;
$X_3$ in the number of $n_1$ is a single bond or a methylene group;
$R_{17}$ and $R_{18}$ in the number of $n_2$ are each independently a hydrogen atom or a methyl group;
$X_5$ in the number of $n_2$ is a single bond or a methylene group;
$X_4$ is a single bond or a methylene group; and
$R_{12}$, $R_{13}$, $R_{14}$, $R_{19}$, $R_{20}$ and $R_{21}$ are each a methyl group.
[8] The branched chain-containing aromatic compound of the aforementioned [1], wherein $R_a$ and $R_b$ are each independently a 3,7,11,15-tetramethylhexadecyl group, a 3,7,11-trimethyldodecyl group, a 2,2,4,8,10,10-hexamethyl-5-dodecanoyl group, a 3,4,5-tri(3',7',11',15'-tetramethylhexadecyloxy)benzyl group, a 3,5-di(3',7',11', 15'-tetramethylhexadecyloxy)benzyl group, a group represented by the formula (f):

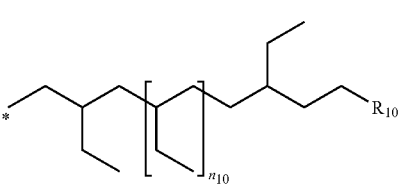
(f)

wherein * shows a bonding position to Q, $n_{10}$ is 23-34, $R_{10}$ is a group represented by the formula (I'):

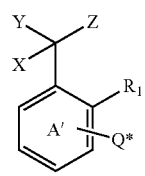
(I')

wherein * shows a bonding position; and other symbols are as defined above, wherein ring A' optionally has, in addition to $R_1$, Q, and C(X) (Y)Z, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms, a group represented by the formula (g):

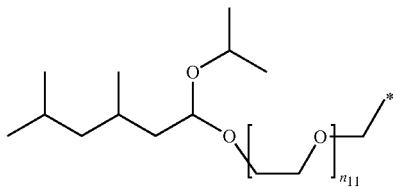

(g)

wherein * shows a bonding position to Q, and $n_{11}$ is 1-10, a group represented by the formula (h):

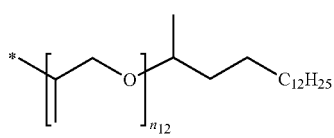

(h)

wherein shows a bonding position to Q, and $n_{12}$ is 2-10, a group represented by the formula (i):

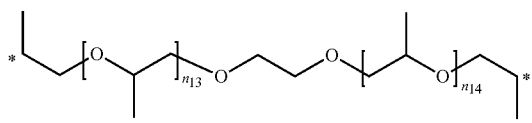

(i)

wherein * shows a bonding position to Q, and $n_{13}$ and $n_{14}$ are each independently 1-10, or
a group represented by the formula (j):

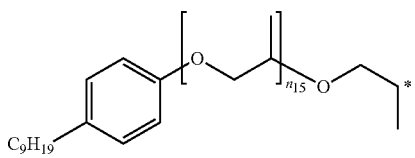

(j)

wherein * shows a bonding position to Q, and $n_{15}$ is 2-20.

[9] The branched chain-containing aromatic compound of any one of the aforementioned [1]-[8], wherein X and Z are both hydrogen atoms, and $R_1$ is a hydrogen atom.
[10] The branched chain-containing aromatic compound of any one of the aforementioned [1]-[8], wherein X is a hydrogen atom, $R_1$ is a hydrogen atom, k is 1, and Z is a group represented by the formula (a) ($R_2$ is a hydrogen atom, and m is 0).
[11] The branched chain-containing aromatic compound of any one of the aforementioned [1]-[8], wherein X is a phenyl group, k is 1, Z is a group represented by the formula (a) (m 0), and $R_2$ is a single bond together with $R_1$ to form a fluorene ring with ring A.
[12] The branched chain-containing aromatic compound of any one of the aforementioned [1]-[11], wherein Q is —O—.
[13] The branched chain-containing aromatic compound of any one of the aforementioned [1]-[12], wherein Y is a hydroxyl group.
[14] The branched chain-containing aromatic compound of any one of the aforementioned [1]-[12], wherein Y is an —NHR group.
[15] The branched chain-containing aromatic compound of the aforementioned [1], which is selected from the group consisting of 2,4-di(2',3'-dihydrophytyloxy)benzyl alcohol; 3,5-di(2',3'-dihydrophytyloxy)benzyl alcohol; 4-(2',3'-dihydrophytyloxy)benzyl alcohol; 1-[(2-chloro-5-(2',3'-dihydrophytyloxy)phenyl)]-1-phenylmethanamine; 3,4,5-tri(2',3'-dihydrophytyloxy)benzyl alcohol; 3,4,5-tri(2',3'-dihydrophytyloxy)benzylamine; 4-(2',3'-dihydrophytyloxy) benzylamine; 2-[3',4',5'-tri(2'',3''-dihydrophytyloxy) benzyloxy]-4-methoxybenzyl alcohol; 4-(2',3'-dihydrophytyloxy)-2-methoxybenzyl alcohol; 4-(2',3'-dihydrophytyloxy)-2-methoxybenzylamine; 4-(2',3'-dihydrophytyloxy)-2-methylbenzyl alcohol; 4-(2',3'-dihydrophytyloxy)-2-methylbenzylamine; 2,2,4,8,10,10-hexamethyl-5-dodecanoic acid (4-hydroxymethyl) phenylamide; 4-(3,7,11-trimethyldodecyloxy)benzyl alcohol; 2-(3,7,11-trimethyldodecyloxy)-9-phenylfluoren-9-ol; a compound represented by the formula:

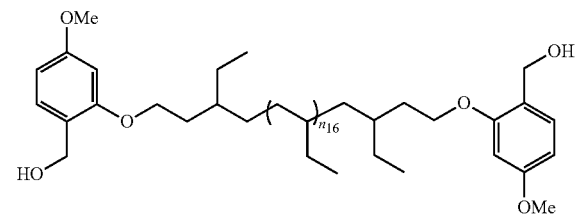

wherein $n_{16}$ is 23 or 34;
a compound represented by the formula:

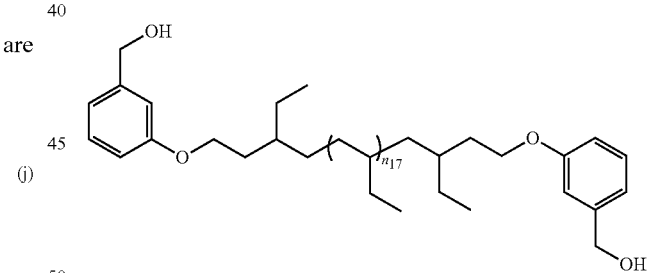

wherein $n_{17}$ is 23 or 34;
a compound represented by the formula:

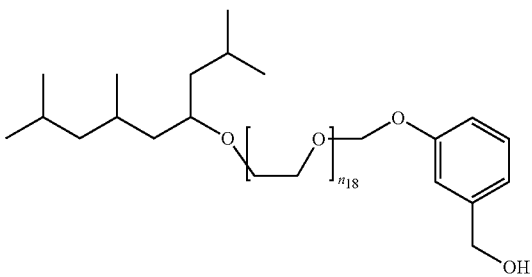

wherein $n_{18}$ is 5-7; and
a compound represented by the formula:

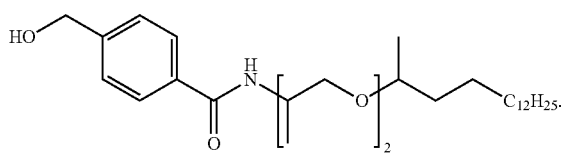

[16] The branched chain-containing aromatic compound of any one of the aforementioned [1]-[15], which shows a saturation solubility in isopropyl acetate (100 g) at 20° C. of 1-95 wt %.
[17] The branched chain-containing aromatic compound of any one of the aforementioned [1]-[15], which shows a saturation solubility in isopropyl acetate (100 g) at 20° C. of 10-95 wt %.
[18] A protecting reagent for a carboxyl group or an amido group of amino acid or peptide, comprising the branched chain-containing aromatic compound of any one of the aforementioned [1]-[17].
[19] The protecting reagent of the aforementioned [18], wherein the amino acid or peptide is protected at the C-terminus.
[20] A branched chain-containing aromatic compound adduct which is protected by the branched chain-containing aromatic compound of any one of the aforementioned [1]-[17].
[21] A method of producing a peptide comprising steps (1)-(4);
(1) a step of condensing the branched chain-containing aromatic compound of any one of the aforementioned [1]-[17] with a C-terminus of an N-protected amino acid or an N-protected peptide in a solvent solubilizing the compound to give an N-protected C-protected amino acid or N-protected C-protected peptide having a C-terminus protected with an anchor which is a protecting group derived from the compound,
(2) a step of removing the N-terminal protecting group from the obtained N-protected C-protected amino acid or N-protected C-protected peptide to give a C-protected amino acid or C-protected peptide,
(3) a step of condensing an N-protected amino acid or N-protected peptide with the N-terminus of the obtained C-protected amino acid or C-protected peptide to give an N-protected C-protected peptide, and
(4) a step of removing the N-terminal protecting group and the C-terminal anchor from the obtained N-protected C-protected peptide to give a peptide.
[22] The method of the aforementioned [21], further comprising one or more repetitions of steps (5)-(7);
(5) a step of removing the N-terminal protecting group of the obtained N-protected C-protected peptide to give a C-protected peptide,
(6) a step of condensing N-protected amino acid or N-protected peptide with the N-terminus of the obtained C-protected peptide to give an N-protected C-protected peptide, and
(7) a step of adding water to the reaction system after step (6), and separating the impurity by extraction into an aqueous layer.
[23] The method of the aforementioned [21], further comprising one or more repetitions of steps (5)-(7');
(5) a step of removing the N-terminal protecting group of the obtained N-protected C-protected peptide to give a C-protected peptide,
(6) a step of condensing N-protected amino acid or N-protected peptide with the N-terminus of the obtained C-protected peptide to give an N-protected C-protected peptide, and
(7') a step of adding a hydrophilic organic solvent to the reaction system after step (6), and separating the impurity by extraction into a hydrophilic organic solvent layer.
[24] An organic synthesis method comprising the peptide production method of any one of the aforementioned [21]-[23].
[25] A branched chain-containing aromatic compound represented by the formula (I):

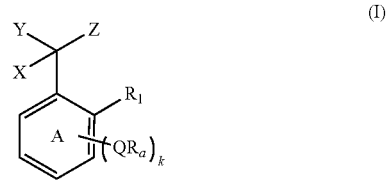

wherein
Q in the number of k are each a single bond, or —O—, —S—, —C(=O)O—, —C(=O)NH— or —NH—;
$R_a$ in the number of k are each independently an organic group having at least one aliphatic hydrocarbon group having one or more branched chains, a total number of the branched chain of not less than 3 and a total carbon number of not less than 14 and not more than 300;
k is an integer of 1-4;
$R_1$ is a hydrogen atom or, when Z is a group represented by the following formula (a), it optionally shows a single bond together with $R_2$ to form a fluorene ring together with ring B; ring A optionally further has, in addition to $R_1$, $QR_a$ in the number of k, and C(X)(Y)Z, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms;
X is a hydrogen atom or a phenyl group;
Y is a hydroxyl group, an —NHR group (wherein R is a hydrogen atom, an alkyl group, or an aralkyl group), or a halogen atom (preferably halogen atom); and
Z is a hydrogenatom or a group represented by the formula (a):

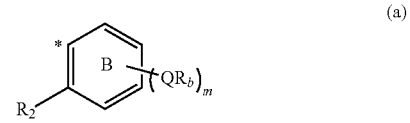

wherein * shows a bonding position;
m is an integer of 0-4;
Q in the number of m are as defined above;
$R_b$ in the number of m are each independently an organic group having at least one aliphatic hydrocarbon group having one or more branched chains, a total number of the branched chain of not less than 3 and a total carbon number of not less than 14 and not more than 300;

$R_2$ is a hydrogen atom, or optionally shows a single bond together with $R_1$ to form a fluorene ring together with ring A; and ring B optionally further has, in addition to $QR_b$ in the number of m, and $R_2$, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms); the organic group having at least one aliphatic hydrocarbon group having one or more branched chains, a total number of the branched chain of not less than 3 and a total carbon number of not less than 14 and not more than 300 for the aforementioned $R_a$ and $R_b$ is a group having 3 or more the same or different divalent groups, which is represented by the formula (b):

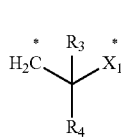

(b)

wherein * shows a bonding position with the adjacent atom; $R_3$ and $R_4$ are each independently a hydrogen atom or a $C_{1-4}$ alkyl group;

$X_1$ is a single bond, a $C_{1-4}$ alkylene group or an oxygen atom, provided that $R_3$ and $R_4$ are not hydrogen atoms at the same time.

[26] A protecting reagent for a carboxyl group or an amido group of amino acid or peptide, comprising the branched chain-containing aromatic compound of the aforementioned [25].

[27] A branched chain-containing aromatic compound adduct which is protected by the branched chain-containing aromatic compound of the aforementioned [25].

[28] A method of producing a peptide comprising steps (1)-(4);

(1) a step of condensing the branched chain-containing aromatic compound of the aforementioned [25] with a C-terminus of an N-protected amino acid or an N-protected peptide in a solvent solubilizing the compound to give an N-protected C-protected amino acid or N-protected C-protected peptide having a C-terminus protected with an anchor which is a protecting group derived from the compound, (2) a step of removing the N-terminal protecting group from the obtained N-protected C-protected amino acid or N-protected C-protected peptide to give a C-protected amino acid or C-protected peptide, (3) a step of condensing an N-protected amino acid or N-protected peptide with the N-terminus of the obtained C-protected amino acid or C-protected peptide to give an N-protected C-protected peptide, and (4) a step of removing the N-terminal protecting group and the C-terminal anchor from the obtained N-protected C-protected peptide to give a peptide.

[29] The method of the aforementioned [28], further comprising one or more repetitions of steps (5)-(7);

(5) a step of removing the N-terminal protecting group of the obtained N-protected C-protected peptide to give a C-protected peptide, (6) a step of condensing N-protected amino acid or N-protected peptide with the N-terminus of the obtained C-protected peptide to give an N-protected. C-protected peptide, and (7) a step of adding water to the reaction system after step (6), and separating the impurity by extraction into an aqueous layer.

[30] The method of the aforementioned [28], further comprising one or more repetitions of steps (5)-(7');

(5) a step of removing the N-terminal protecting group of the obtained N-protected C-protected peptide to give a C-protected peptide, (6) a step of condensing N-protected amino acid or N-protected peptide with the N-terminus of the obtained C-protected peptide to give an N-protected C-protected peptide, and (7') a step of adding a hydrophilic organic solvent to the reaction system after step (6), and separating the impurity by extraction into a hydrophilic organic solvent layer.

[31] An organic synthesis method comprising the peptide production method of any one of the aforementioned [28]-[30].

Effect of the Invention

The branched chain-containing aromatic compound of the present invention is easily-soluble in isopropyl acetate superior in liquid-separating operability. Using the branched chain-containing aromatic compound of the present invention, therefore, a production method of peptide and the like comprising leading to a final product via extraction separation alone, without crystallization and isolation of each intermediate in each step, can be performed.

DESCRIPTION OF EMBODIMENTS

Unless otherwise specified in the sentences, any technical terms and scientific terms used in the present specification, have the same meaning as those generally understood by those of ordinary skill in the art the present invention belongs to. Any methods and materials similar or equivalent to those described in the present specification can be used for practicing or testing the present invention, and preferable methods and materials are described in the following. All publications and patents referred to in the present specification are hereby incorporated by reference so as to describe and disclose constructed products and methodology described in, for example, publications usable in relation to the described invention.

[The Compound of the Present Invention]

The branched chain-containing aromatic compound of the present invention (hereinafter sometimes to be abbreviated as the compound of the present invention) is represented by the following formula (I). The compound of the present invention encompasses a particular benzyl compound (in the formula (I), X and Z are both hydrogen atoms, and $R_1$ is a hydrogen atom); a particular diphenylmethane compound (in the formula (I), X is a hydrogen atom, $R_1$ is a hydrogen atom, k is 1, and Z is a group represented by the formula (a) wherein $R_2$ is a hydrogen atom and m is 0; and a particular fluorene compound (in the formula (I), X is a phenyl group, k is 1, Z is a group represented by the formula (a) wherein m is 0, and $R_2$ is a single bond together with $R_1$ to form a fluorene ring with ring A).

The formula (I):

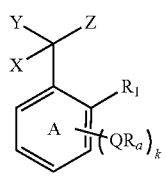

wherein
Q in the number of k are each a single bond, or —O—, —S—, —C(=O)O—, —C(=O)NH— or —NH—;
$R_a$ in the number of k are each independently an organic group having at least one aliphatic hydrocarbon group having one or more branched chains, a total number of the branched chain of not less than 3 and a total carbon number of not less than 14 and not more than 300;
k is an integer of 1-4;
$R_1$ is a hydrogen atom or, when Z is a group represented by the following formula (a), it optionally shows a single bond together with $R_2$ to form a fluorene ring together with ring B; ring A optionally further has, in addition to $R_1$, $QR_a$ in the number of k, and C(X)(Y)Z, substituent(s) selected from the group consisting of a halogen atom, a $C_1$-6 alkyl group optionally substituted by one or more halogen atoms, and a $C_{1-6}$ alkoxy group optionally substituted by one or more halogen atoms;
X is a hydrogen atom or a phenyl group;
Y is a hydroxyl group, an —NHR group (R is a hydrogen atom, an alkyl group or an aralkyl group) or a halogen atom; and
Z is a hydrogen atom or a group represented by the formula (a):

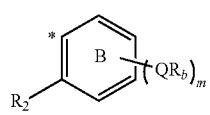

wherein * shows a bonding position;
m is an integer of 0-4;
Q in the number of m are as defined above;
$R_b$ in the number of m are each independently an organic group having at least one aliphatic hydrocarbon group having one or more branched chains, a total number of the branched chain of not less than 3 and a total carbon number of not less than 14 and not more than 300;
$R_2$ is a hydrogen atom, or optionally shows a single bond together with $R_1$ to form a fluorene ring together with ring A; and
ring B optionally further has, in addition to $QR_b$ in the number of m, and $R_2$, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms).

The compound represented by the formula (I) of the present invention and compounds intended to protect are bonded by a condensation reaction of a hydroxyl group, an NHR group or a halogen atom for Y group with a carboxyl group of a compound to be protected or the like.

In the present specification, examples of the "alkyl group" for R include a $C_{1-30}$ alkyl group, preferably a $C_{1-10}$ alkyl group, more preferably a $C_{1-6}$ alkyl group. Preferable examples include methyl, ethyl, propyl, isopropyl, butyl, isobutyl, sec-butyl, tert-butyl, and the like, and particularly preferred are methyl and ethyl.

In the present specification, examples of the "aralkyl group" for R include a $C_{7-30}$ aralkyl group. Preferred is a $C_{7-20}$ aralkyl group, more preferred is a $C_{7-16}$ aralkyl group (a $C_{6-10}$ aryl-$C_{1-6}$ alkyl group). Preferable examples include benzyl, 1-phenylethyl, 2-phenylethyl, 1-phenylpropyl, α-naphthylmethyl, 1-(α-naphthyl)ethyl, 2-(α-naphthyl)ethyl, 1-(α-naphthyl) propyl, β-naphthylmethyl, 1-(β-naphthyl)ethyl, 2-(β-naphthyl)ethyl, 1-(β-naphthyl)propyl and the like, and particularly preferred is benzyl.

As R, a hydrogen atom, a $C_{1-6}$ alkyl group or a $C_{7-16}$ aralkyl group is preferable, a hydrogen atom, methyl, ethyl or benzyl is more preferable, and a hydrogen atom is particularly preferable.

In the present specification, the "halogen atom" is a fluorine atom, a chlorine atom, a bromine atom or an iodine atom. Preferred as the "halogen atom" for Y is a chlorine atom, a bromine atom or an iodine atom, and more preferred is a bromine atom.

In the present specification, the "organic group having at least one aliphatic hydrocarbon group having one or more branched chains, a total number of the branched chain of not less than 3 and a total carbon number of not less than 14 and not more than 300" for $R_a$ and $R_b$ is an organic group having at least one aliphatic hydrocarbon group having one or more branched chains in a molecular structure thereof, a total number of the branched chain of not less than 3 and a total carbon number of not less than 14 and not more than 300.

The "branched chain" of the "aliphatic hydrocarbon group having one or more branched chains" is a straight or branched saturated aliphatic hydrocarbon group. Preferred is a $C_{1-6}$ alkyl group, more preferred is a $C_{1-4}$ alkyl group, and still more preferred is a methyl group or an ethyl group. In addition, the "branched chain" is optionally substituted by one or more halogen atoms.

The "aliphatic hydrocarbon group" of the "aliphatic hydrocarbon group having one or more branched chains" is a straight saturated or unsaturated aliphatic hydrocarbon group, a $C_2$-$C_{300}$ alkyl group (preferably, a $C_3$-$C_{100}$ alkyl group, more preferably, a $C_3$-$C_{60}$ alkyl group), a $C_2$-$C_{300}$ alkenyl group (preferably, a $C_3$-$C_{00}$ alkenyl group, more preferably, a $C_3$-$C_{60}$ alkenyl group) or a $C_2$-$C_{300}$ alkynyl group (preferably, a $C_3$-$C_{100}$ alkynyl group, more preferably, a $C_3$-$C_{60}$ alkynyl group).

The moiety of the "aliphatic hydrocarbon group having one or more branched chains" of the "organic group having at least one aliphatic hydrocarbon group having one or more branched chains, a total number of the branched chain of not less than so 3 and a total carbon number of not less than 14 and not more than 300" is not particularly limited, and it may be present at the terminal (monovalent group), or other site (e.g., divalent group).

Specific examples of the "aliphatic hydrocarbon group having one or more branched chains" include a monovalent group having one or more branched chain(s) of a branched isomer of a propyl group, a butyl group, a pentyl group, a hexyl group, a heptyl group, an octyl group, a nonyl group, a decyl group, an undecyl group, a dodecyl group (a lauryl group), a tridecyl group, a myristyl group, a cetyl group, a stearyl group, an arachyl group, a behenyl group, an oleyl group, a linolyl group, a lignoceryl group and the like, and a divalent group derived therefrom, preferably, a 3,7,11-trimethyldodecyl group, a 3,7,11,15-tetramethylhexadecyl group (hereinafter sometimes to be referred to as a 2,3- dihydrophytyl group), a 2,2,4,8,10,10-hexamethylundecan-5-yl group, a group represented by the formula:

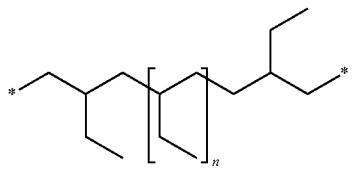

n = 23-34 wherein * shows a bonding position to Q, and the like.

When plural "aliphatic hydrocarbon groups having one or more branched chains" are in the "organic group having at least one aliphatic hydrocarbon group having one or more branched chains, a total number of the branched chain of not less than 3 and a total carbon number of not less than 14 and not more than 300", each may be same or different.

The moiety other than the "aliphatic hydrocarbon group having one or more branched chains" of the "organic group having at least one aliphatic hydrocarbon group having one or more branched chains, a total number of the branched chain of not less than 3 and a total carbon number of not less than 14 and not more than 300" can be set freely. For example, the group optionally has moieties such as —C—, —S—, —CO—, —NH—, —COO—, —OCONH—, —CONH—, —NHCO—, hydrocarbon group (monovalent group or divalent group) and the like. Examples of the "hydrocarbon group" include an aliphatic hydrocarbon group, an aromatic aliphatic hydrocarbon group, a monocyclic saturated hydrocarbon group, an aromatic hydrocarbon group and the like. Specifically, for example, monovalent groups such as an alkyl group, an alkenyl group, an alkynyl group, a cycloalkyl group, an aryl group, an aralkyl group and the like, and divalent groups derived therefrom are used. As the "alkyl group", a $C_{1-6}$ alkyl group and the like are preferable and, for example, methyl, ethyl, propyl, isopropyl, butyl, isobutyl, sec-butyl, tert-butyl, pentyl, hexyl and the like can be mentioned. As the "alkenyl group", a $C_{2-6}$ alkenyl group and the like are preferable and, for example, vinyl, 1-propenyl, allyl, isopropenyl, butenyl, isobutenyl and the like can be mentioned. As the "alkynyl group", a $C_{2-6}$ alkynyl group and the like are preferable and, for example, ethynyl, propargyl, 1-propynyl and the like can be mentioned. As the "cycloalkyl group", a $C_{3-6}$ cycloalkyl group and the like are preferable and, for example, cyclopropyl, cyclobutyl, cyclopentyl and cyclohexyl can be mentioned. As the "aryl group", for example, a $C_{6-14}$ aryl group and the like are preferable and, for example, phenyl, 1-naphthyl, 2-naphthyl, biphenylyl, 2-anthryl and the like can be mentioned. Of these, a $C_{6-10}$ aryl group is more preferable, and phenyl is particularly preferable. As the "aralkyl group", a $C_{7-20}$ aralkyl group is preferable and, for example, benzyl, 1-phenylethyl, 2-phenylethyl, 1-phenylpropyl, naphthylmethyl, 1-naphthylethyl, 1-naphthylpropyl and the like can be mentioned. Of these, a $C_{7-16}$ aralkyl group ($C_{6-10}$ aryl-$C_{1-6}$ alkyl group) is more preferable, and benzyl is particularly preferable. The "hydrocarbon group" is optionally substituted by a substituent selected from a halogen atom (a chlorine atom, a bromine atom, a fluorine atom, an iodine atom), an oxo group and the like.

The compound of the present invention has a $QR_a$ group in the number of k. Here, Q is a single bond, or —O—, —S—, —C(=O)O—, —C(=O)NH— or —NH—, preferably O. The $QR_a$ group in the number of k may be the same or different.

In the compound of the present invention, the "organic group having at least one aliphatic hydrocarbon group having one or more branched chains, a total number of the branched chain of not less than 3 and a total carbon number of not less than 14 and not more than 300" for $R_a$ and $R_b$ preferably has a total carbon number of not less than 14, preferably not less than 16, more preferably not less than 18. The "organic group having at least one aliphatic hydrocarbon group having one or more branched chains, and an aliphatic hydrocarbon group having a total number of the branched chain of not less than 3" for $R_a$ and $R_b$ preferably has a total carbon number of not more than 300, preferably not more than 200, more preferably not more than 160. In addition, in the compound of in the present invention, the "organic group having at least one aliphatic hydrocarbon group having one or more branched chains, and an aliphatic hydrocarbon group having a total number of the branched chain of not less than 3" for $R_a$ and $R_b$ preferably has a total number of the branched chain of not less than 3, preferably not less than 4, more preferably not less than 8, further preferably not less than 10. When the total number of the branched chain is higher, a compound protected by the compound of the present invention becomes an oil showing good solubility in various organic solvents even when the peptide chain becomes long.

As the "organic group having at least one aliphatic hydrocarbon group having one or more branched chains, a total number of the branched chain of not less than 3 and a total carbon number of not less than 14 and not more than 300" for $R_a$ and $R_b$, a group having 3 or more, the same or different divalent groups represented by the formula (b):

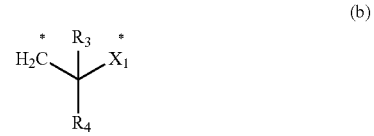

(b)

wherein shows a bonding position with the adjacent atom; $R_3$ and $R_4$ are each independently a hydrogen atom or a $C_1$-$C_4$ alkyl group; $X_1$ is a single bond, a $C_{1-4}$ alkylene group or an oxygen atom, provided that $R_3$ and $R_4$ are not hydrogen atoms at the same time, is preferable and, for example, a group represented by any of the following formulas (c)-(e) can be mentioned.

The carbon number, repeat unit number ($m_1$, $n_0$-$n_9$) and the like in the definition of each symbol in the formulas (c)-(e) are shown for convenience, and can be changed as appropriate within the range defined above, so that the total number of the carbon will be not less than 14 (preferably not less than 16, more preferably not less than 18) and not more than 300 (preferably not more than 200, more preferably not more than 160). In the following, the formulas (c)-(e) are explained in this order.

The formula (c) is as described below.

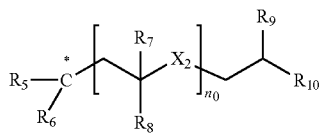
(c)

wherein * shows a bonding position to Q;

$R_5$ and $R_6$ are both hydrogen atoms, or show =O in combination;

$n_0$ is an integer of 2-40;

$R_7$ and $R_8$ in the number of $n_0$ are each independently a hydrogen atom or a $C_{2-4}$ alkyl group;

$X_2$ in the number of $n_0$ are each independently a single bond or a $C_{1-4}$ alkylene group; and $R_9$ is a hydrogen atom or a $C_{1-4}$ alkyl group;

$R_{10}$ is a $C_{1-4}$ alkyl group or the formula (I')

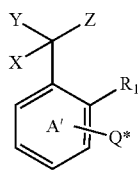
(I')

wherein * shows a bonding position;

other symbols are as defined above, and ring A' optionally has, in addition to $R_1$, Q, and C(X)(Y)Z, substituent(s) selected from the group consisting of a halogen atom, a $C_{1-6}$ alkyl group optionally substituted by one or more halogen atoms, and a $C_{1-6}$ alkoxy group optionally substituted by one or more halogen atoms, provided that $R_7$ and $R_8$ are not hydrogen atoms at the same time, and when $n_0$ is 2, $R_9$ is a $C_{1-4}$ alkyl group.

In the group of the formula (c), a group wherein $R_5$ and $R_6$ are both hydrogen atoms;

$n_0$ is an integer of 2-40;

$R_7$ and $R_8$ in the number of $n_0$ are each independently a hydrogen atom, a methyl group or an ethyl group;

$X_2$ in the number of $n_0$ are each independently a single bond, a methylene group or an ethylene group; and $R_9$ is a hydrogen atom, a methyl group or an ethyl group is preferable, provided that $R_7$ and $R_8$ are not hydrogen atoms at the same time, and when $n_0$ is 2, $R_9$ is methyl or an ethyl group.

More preferable group of the formula (c) is a group of a branched isomer having a carbon number of 14 to 160, of a myristyl group, a cetyl group, a stearyl group, an arachyl group, a behenyl group and the like, wherein the total number of the branched chain is not less than 3. Of these, a 2,3-dihydrophytyl group, a 3,7,11-trimethyldodecyl group and a 2,2,4,8,10,10-hexamethyl-5-dodecanoyl group are particularly preferable.

The formula (d) is as described below.

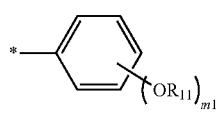
(d)

wherein * shows a bonding position to Q;

$OR_{11}$ in the number of $m_1$ is hydroxyl group substituted by a group represented by the formula (c') or a hydroxyl group substituted by a group having a polyalkyleneglycol group wherein the total number of the branched chain is not less than 3 (e.g., a polypropylene glycol group, a polyneopentylglycol group); and $m_1$ is an integer of 1-3.

The explanation of the group represented by the above-mentioned formula (c') is the same as the explanation of a group represented by the above-mentioned formula (c) except that * does not show a bonding position to Q but shows a bonding position to O.

In the group of the formula (d), $R_{11}$ is more preferably a group of a branched isomer having a carbon number of 14 to 30 of a myristyl group, a cetyl group, a stearyl group, an arachyl group, a behenyl group and the like, wherein the total number of the branched chain is not less than 3. Of these, a 2,3-dihydrophytyl group and a 3,7,11-trimethyldodecyl group are particularly preferable.

The formula (e) is as described below.

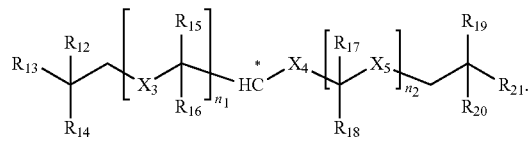
(e)

wherein * shows a bonding position to Q;

$n_1$ is an integer of 1-10;

$n_2$ is an integer of 1-10;

$R_{15}$ and $R_{16}$ in the number of $n_1$ are each independently a hydrogen atom or a $C_{1-4}$ alkyl group;

$X_3$ in the number of $n_1$ is a single bond or a $C_1$-4 alkylene group;

$R_{17}$ and $R_{18}$ in the number of $n_2$ are each independently a hydrogen atom or a $C_{1-4}$ alkyl group;

$X_5$ in the number of $n_2$ is a single bond or a $C_{1-4}$ alkylene group;

$X_4$ is a single bond or a $C_{1-4}$ alkylene group; and $R_{12}$, $R_{13}$, $R_{14}$, $R_{19}$, $R_{20}$ and $R_{21}$ are each independently a hydrogen atom or a $C_{1-4}$ alkyl group, provided that $R_{15}$ and $R_{16}$ and/or $R_{17}$ and $R_1$ are not hydrogen atoms at the same time, and when $n_1+n_2$ is 2, two or more of $R_{12}$, $R_{13}$ and $R_{14}$ are each independently a $C_{1-4}$ alkyl group, or two or more of $R_{19}$, $R_{20}$ and $R_{21}$ are each independently a $C_{1-4}$ alkyl group.

A group of the formula (e), wherein $n_1$ is an integer of 1-5;

$n_2$ is an integer of 1-5;

$R_{15}$ and $R_{16}$ in the number of $n_1$ are each independently a hydrogen atom, a methyl group or an ethyl group;

$X_3$ in the number of $n_1$ is a single bond, a methylene group or an ethylene group;

$R_{17}$ and $R_{18}$ in the number of $n_2$ are each independently a hydrogen atom, a methyl group or an ethyl group;

$X_5$ in the number of $n_2$ is a single bond, a methylene group or an ethylene group;
$X_4$ is a single bond, a methylene group or an ethylene group; and
$R_{12}$, $R_{13}$, $R_{14}$, $R_{19}$, $R_{20}$ and $R_{21}$ are each independently a hydrogen atom or a $C_{1-4}$ alkyl group is more preferable, provided that $R_{15}$ and $R_{16}$ and/or $R_{17}$ and $R_{18}$ are not hydrogen atoms at the same time, and when $n_1+n_2$ is 2, two or more of $R_{12}$, $R_{13}$ and $R_{14}$ are each independently a $C_{1-4}$ alkyl group, or two or more of $R_{19}$, $R_{20}$ and $R_{21}$ are each independently a $C_{1-4}$ alkyl group.

A group of the formula (e), wherein
$n_1$ is an integer of 1-5;
$n_2$ is an integer of 1-5;
$R_{15}$ and $R_{16}$ in the number of $n_1$ are each independently a hydrogen atom or a methyl group;
$X_3$ in the number of $n_1$ is a single bond or a methylene group;
$R_{17}$ and $R_{18}$ in the number of $n_2$ are each independently a hydrogen atom or a methyl group;
$X_5$ in the number of $n_2$ is a single bond or a methylene group;
$X_4$ is a single bond or a methylene group; and
$R_{12}$, $R_{13}$, $R_{14}$, $R_{19}$, $R_{20}$ and $R_{21}$ are each a methyl group, provided that $R_{15}$ and $R_{16}$ and/or $R_{17}$ and $R_{18}$ are not hydrogen atoms at the same time is particularly preferable.

The "organic group having at least one aliphatic hydrocarbon group having one or more branched chains, a total number of the branched chain of not less than 3 and a total carbon number of not less than 14 and not more than 300" for $R_a$ and $R_b$ may be a group represented by any of the above-mentioned formulas (c)-(e), or a group having 3 or more groups of the above-mentioned formula (b), wherein $X_1$ is an oxygen atom, i.e., a group containing a polyalkyleneglycol group such as a polypropyleneglycol group, a polyneopentylglycol group and the like, wherein the total number of the branched chain is not less than 3.

Specific examples of the "organic group having at least one aliphatic hydrocarbon group having one or more branched chains, a total number of the branched chain of not less than 3 and a total carbon number of not less than 14 and not more than 300" for $R_a$ and $R_b$ include the following groups, wherein in each group shows a bonding position, $n_3$ in the formula is an integer of not less than 3, and $n_4$ can be appropriately adjusted so that the total carbon number of the group will be not less than 14 and not more than 300.

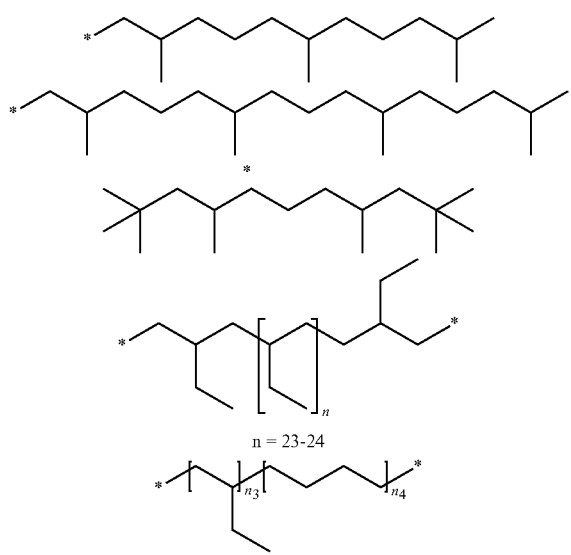

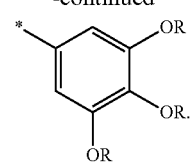

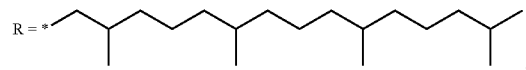

In addition, examples of other embodiment of the "organic group having at least one aliphatic hydrocarbon group having one or more branched chains, a total number of the branched chain of not less than 3 and a total carbon number of not less than 14 and not more than 300" for $R_a$ and $R_b$ include the following groups, wherein in each group shows a bonding position.

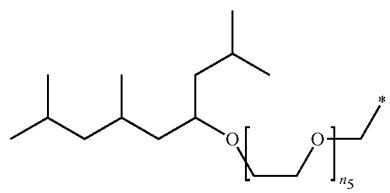

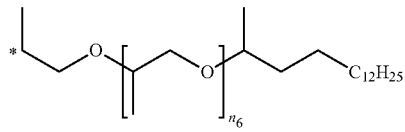

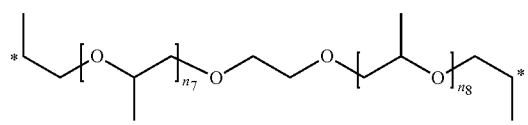

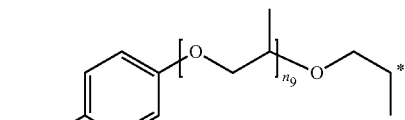

wherein $n_5$-$n_9$ can be appropriately adjusted so that the total carbon number of each group will be not less than 14 and not more than 300.

Specific preferable examples of the "organic group having at least one aliphatic hydrocarbon group having one or more branched chains, a total number of the branched chain of not less than 3 and a total carbon number of not less than 14 and not more than 300" for $R_a$ and $R_b$ include the following groups:

a 3,7,11,15-tetramethylhexadecyl group;

a 3,7,11-trimethyldodecyl group;

a 2,2,4,8,10,10-hexamethyl-5-dodecanoyl group;

a 3,4,5-tri(3',7',11',15'-tetramethylhexadecyloxy)benzyl group;

a 3,5-di(3',7',11',15'-tetramethylhexadecyloxy)benzyl group;

a group represented by the formula (f):

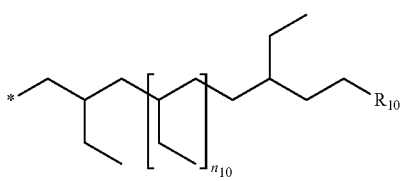

wherein * shows a bonding position to Q, $n_{10}$ is 23-34, and $R_{10}$ is a group represented by the formula (I');

a group represented by the formula (g):

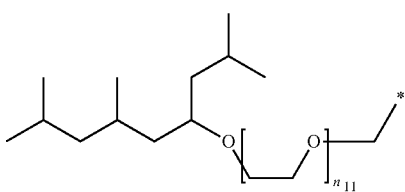

wherein * shows a bonding position to Q, and $n_{11}$ is 1-10; a group represented by the formula (h):

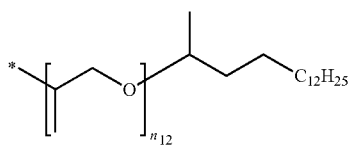

wherein * shows a bonding position to Q, and $n_{12}$ is 2-10; a group represented by the formula (i):

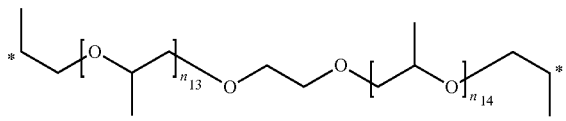

wherein * shows a bonding position to Q, $n_{13}$ and $n_{14}$ are each independently 1-10; and a group represented by the formula (j):

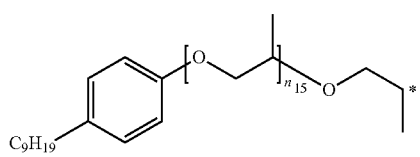

wherein * shows a bonding position to Q, and $n_{15}$ is 2-20.

Preferable examples of the compound of the present invention include, but are not limited to the following benzyl compound, diphenylmethane compound and fluorene compound:

2,4-di(2',3'-dihydrophytyloxy)benzyl alcohol;
3,5-di(2',3'-dihydrophytyloxy)benzyl alcohol;
4-(2',3'-dihydrophytyloxy)benzyl alcohol;
1-[(2-chloro-5-(2',3'-dihydrophytyloxy)phenyl)]-1-phenyl-methanamine;
3,4,5-tri(2',3'-dihydrophytyloxy)benzyl alcohol;
3,4,5-tri(2',3'-dihydrophytyloxy)benzylamine;
4-(2',3'-dihydrophytyloxy)benzylamine;
2-[3',4',5'-tri(2'',3''-dihydrophytyloxy)benzyloxy]-4-methoxybenzylalcohol;
4-(2',3'-dihydrophytyloxy)-2-methoxybenzylalcohol;
4-(2',3'-dihydrophytyloxy)-2-methoxybenzylamine;
4-(2',3'-dihydrophytyloxy)-2-methylbenzylalcohol;
4-(2',3'-dihydrophytyloxy)-2-methylbenzylamine;
2,2,4,8,10,10-hexamethyl-5-dodecanoic acid (4-hydroxymethyl)phenylamide;
4-(3,7,11-trimethyldodecyloxy)benzyl alcohol;
2-(3,7,11-trimethyldodecyloxy)-9-phenylfluoren-9-ol;

a compound represented by the formula:

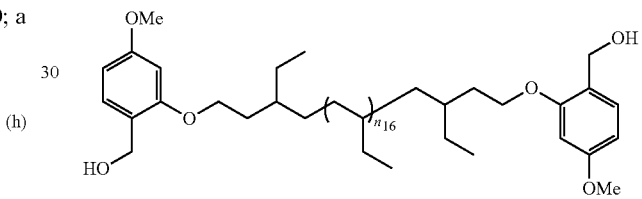

wherein $n_{16}$ is 23-34;

a compound represented by the formula:

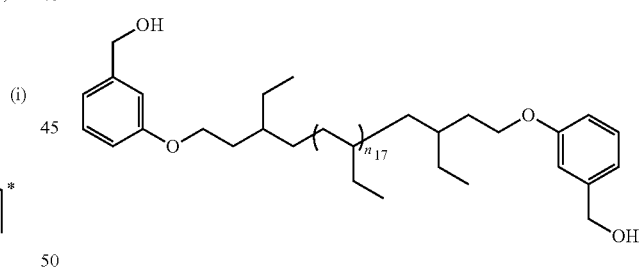

wherein $n_{17}$ is 23-34; and a compound represented by the formula:

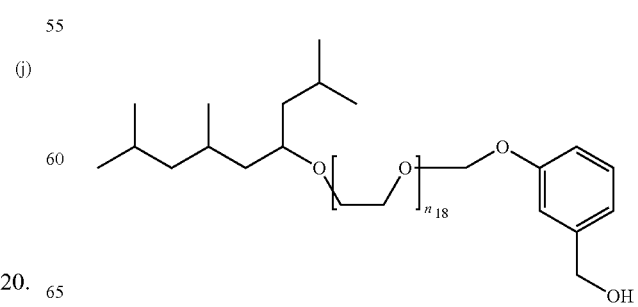

wherein $n_{18}$ is 1-10;
a compound represented by the formula:

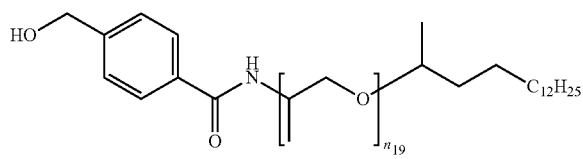

wherein $n_{18}$ is 2-10.

Of these,
2,4-di(2',3'-dihydrophytyloxy)benzyl alcohol;
3,5-di(2',3'-dihydrophytyloxy)benzyl alcohol;
4-(2',3'-dihydrophytyloxy)benzyl alcohol;
1-[(2-chloro-5-(2',3'-dihydrophytyloxy)phenyl)]-1-phenyl-methanamine;
3,4,5-tri(2',3'-dihydrophytyloxy)benzyl alcohol;
3,4,5-tri(2',3'-dihydrophytyloxy)benzylamine;
s 4-(2',3'-dihydrophytyloxy)benzylamine;
2-[3',4',5'-tri(2'',3''-dihydrophytyloxy)benzyloxy]-4-methoxybenzyl alcohol;
4-(2',3'-dihydrophytyloxy)-2-methoxybenzyl alcohol;
4-(2',3'-dihydrophytyloxy)-2-methoxybenzylamine;
4-(2',3'-dihydrophytyloxy)-2-methylbenzyl alcohol;
4-(2',3'-dihydrophytyloxy)-2-methylbenzylamine;
2,2,4,8,10,10-hexamethyl-5-dodecanoic acid (4-hydroxymethyl)phenylamide;
4-(3,7,11-trimethyldodecyloxy)benzyl alcohol;
2-(3,7,11-trimethyldodecyloxy)-9-phenylfluoren-9-ol;
a compound represented by the formula:

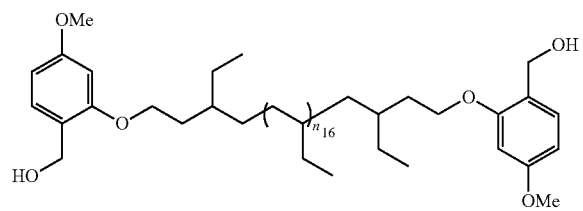

wherein $n_{16}$ is 23 or 34;
a compound represented by the formula:

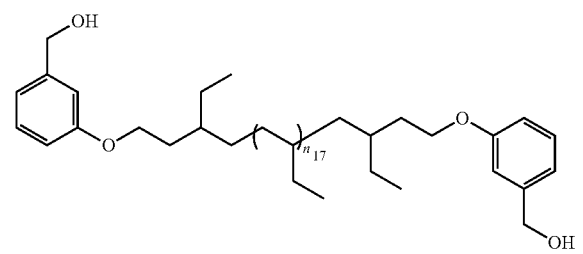

wherein $n_{17}$ is 23 or 34;
a compound represented by the formula:

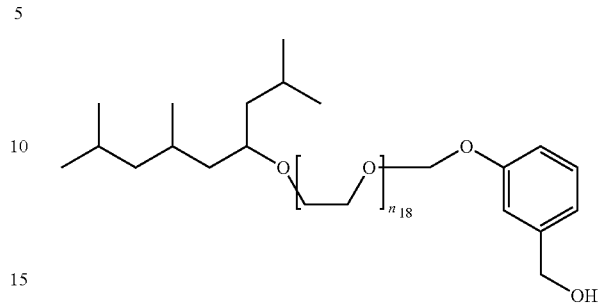

wherein $n_{18}$ is 5-7; and
a compound represented by the formula:

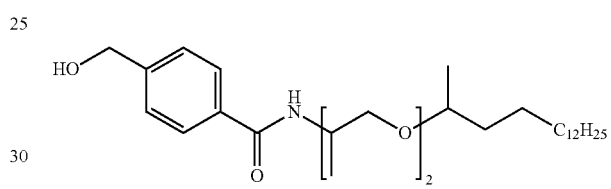

are particularly preferable.

[Production Method of the Compound of the Present Invention]

While the production method of the compound of the present invention is not particularly limited, it can be synthesized, for example, via the following reactions.

Unless otherwise specified, the starting compound may be a commercially available product, or can be produced according to a method known per se or a method analogous thereto.

While the yield of the compound obtained by each of the following methods may vary depending on the reaction conditions employed, the compound can be isolated and purified from the resulting product by a general method (recrystallization, column chromatography and the like), and then precipitated by a method of changing the solution temperature, a method of changing the solution composition and the like.

In each reaction, when the starting compound has a hydroxy group, an amino group, a carboxy group, a carbonyl group or the like, a protecting group generally used in the peptide chemistry and the like may be introduced into these groups, and the objective compound can be obtained by removing the protecting group as necessary after the reaction.

The compound of the present invention can be produced, for example, according to the following steps.

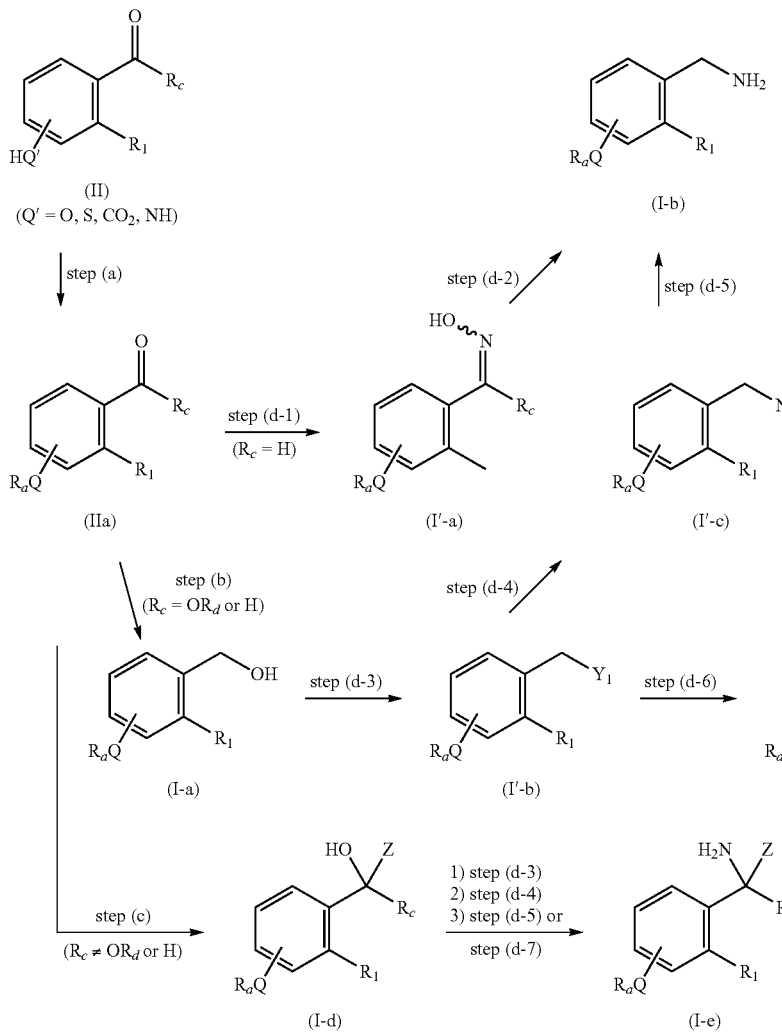

wherein Q' is —O—, —S—, —C(=O)O— or —NH—, $R_c$ is a hydrogen atom, an $OR_d$ group ($R_d$ is an alkyl group such as a $C_{1-6}$ alkyl group and the like, an aralkyl group such as a benzyl group etc. and the like) or a group represented by the formula (a):

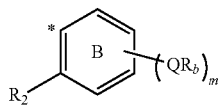

wherein each symbol is as defined above, $Y_1$ is a leaving group such as a halogen atom and the like, other symbols are as defined above.

Step (a)

In this step, an $R_a$ group is introduced into a Q'H group wherein Q' is —O—, —S—, —C(=O)O— or —NH— of a compound represented by the formula (II) (hereinafter to be abbreviated as compound (II)) to give a compound represented by the formula (IIa) (hereinafter to be abbreviated as compound (IIa)).

When Q' is —O—, —S— or —NH—, the reaction is carried out in a solvent that does not influence the reaction, in the presence or absence of a base and using a halide corresponding to an $R_a$ group (chloride, bromide or iodide), a carboxylic acid or an acid halide corresponding to an $R_a$ group or alkylsulfonyloxylation product (e.g., methanesulfonyloxylation product etc.) or an arylsulfonyloxylation product (e.g., p-toluenesulfonyloxylation product etc.) corresponding to an $R_a$ group. In addition, when Q' is —O—, the reaction can be carried out by reacting compound (II) with hydroxide corresponding to an $R_a$ group in the presence of triphenylphosphine and diisopropyl azodicarboxylate, under the conditions of Mitsunobu reaction. Furthermore, when Q' is —C(=O)O—, for example, compound (IIa) can be synthesized by reacting compound (II) with amine or hydroxide corresponding to an $R_a$ group in the presence of the below-mentioned condensing agent.

Examples of the base include alkali metal salt such as sodium carbonate, sodium hydrogen carbonate, potassium carbonate, sodium hydride, potassium hydride, potassium tert-butoxide and the like; amines such as pyridine, triethylamine, N,N-dimethylaniline, 1,8-diazabicyclo[5.4.0]undec-7-ene etc., and the like. Of these, sodium carbonate, potassium carbonate, sodium hydride and the like are preferable.

Examples of the solvent include aromatic hydrocarbons such as toluene, xylene and the like; ethers such as tetrahydrofuran, dioxane and the like; amides such as dimethylformamide, dimethylacetamide and the like; halogenated hydrocarbons such as chloroform, dichloromethane and the like; nitriles such as acetonitrile and the like, N-methylpyrrolidone, and a mixture thereof. Of these, dimethylformamide, tetrahydrofuran, toluene, N-methylpyrrolidone and the like are preferable.

The reaction temperature is generally 50° C. to 150° C., preferably 60° C. to 130° C. The reaction time is generally 2-hr, preferably 3-10 hr.

Step (b)

In this step, compound (IIa) is reduced to give a compound represented by the formula (I-a) (hereinafter to be abbreviated as compound (I-a)). The reduction reaction can be performed by a method using a reducing agent.

Examples of the reducing agent to be used for the reduction reaction include metal hydride (sodium borohydride, lithium borohydride, sodium cyanoborohydride, sodium triacetoxyborohydride, dibutylaluminum hydride, aluminum hydride, lithium aluminum hydride, etc.) and the like. Of these, sodium borohydride, dibutylaluminum hydride and the like are preferable.

The reaction is performed in a solvent that does not influence the reaction. Examples of the solvent include alcohols such as methanol, ethanol and the like; ethers such as diethyl ether, tetrahydrofuran, dioxane and the like; aromatic hydrocarbons such as toluene, xylene and the like; and a mixture thereof. Of these, tetrahydrofuran, toluene and the like are preferable.

The reaction temperature is generally 0° C. to 100° C., preferably 30° C. to 70° C., and the reaction time is generally 1-24 hr, preferably 2-5 hr.

step (c)

In this step, compound (IIa) (in the formula (IIa), $R_c$ is not a hydrogen atom or an $OR_d$ group) is reduced in the same manner as in the above-mentioned step (b) or a phenyl group (corresponding to the above-mentioned Z group) is introduced by a Grignard reaction.

In the Grignard reaction, a commercially available Grignard reagent (e.g., phenylmagnesium bromide, phenylmagnesium chloride etc.) can be used, or a reagent prepared by reacting magnesium with halobenzene (chlorobenzene, bromobenzene, iodobenzene) in the presence of iodine or dibromoethane can be used.

The Grignard reaction is carried out in a solvent that does not influence the reaction. Examples of the solvent include ethers such as diethyl ether, tetrahydrofuran, 1,2-dimethoxyethane and the like; aromatic hydrocarbons such as toluene, xylene and the like; and a mixture thereof. Of these, tetrahydrofuran, 1,2-dimethoxyethane and the like are preferable.

The reaction temperature is generally −20 to 100° C., preferably 0 to 70° C., and the reaction time is generally 1-24 hr, preferably 2-10 hr.

Step (d-1)

In this step, compound (IIa) (in the formula (IIa), $R_c$ is a hydrogen atom) is oximated to give a compound represented by the formula (I'-a) (hereinafter to be abbreviated as compound (I'-a)).

The oximation reaction includes reacting compound (IIa) with hydroxylamine acid addition salt in a solvent that does not influence the reaction in the presence of a base.

Examples of the hydroxylamine acid addition salt include mineral acid salts such as hydrochloride, sulfate, nitrate and the like, organic acid salts such as acetate, trifluoroacetate, methanesulfonate, trifluoromethanesulfonate, p-toluenesulfonate etc., and the like, and hydrochloride is particularly preferable.

Examples of such base include alkali metal salts such as potassium hydroxide, sodium hydroxide, sodium hydrogen carbonate, potassium carbonate and the like; organic amines such as pyridine, triethylamine, diisopropylethylamine, N,N-dimethylaniline, 1,8-diazabicyclo[5.4.0]undec-7-ene etc., and the like. Of these, triethylamine, diisopropylethylamine and the like are preferable.

Examples of the solvent include halogen solvents such as chloroform, dichloromethane and the like; aromatic hydrocarbons such as toluene, xylene and the like; ethers such as tetrahydrofuran, dioxane and the like; and/or a mixture thereof. Of these, dichloromethane, chloroform, toluene and the like are preferable.

The reaction temperature is generally 10° C. to 100° C., preferably 20° C. to 60° C., and the reaction time is generally 0.5-30 hr, preferably 2-20 hr.

Step (d-2)

In this step, compound (I'-a) is reduced by a catalytic hydrogenation reaction in the presence of a metal catalyst such as palladium-carbon, Raney-nickel and the like, or by a reducing agent such as metal hydride and the like, which is similar to those in the aforementioned step (b), to give a compound represented by the formula (I-b) (hereinafter to be abbreviated as compound (I-b)), which is the compound of the present invention.

Compound (I-b) can also be produced from step (d-3) via step (d-4) and step (d-5).

Step (d-3)

In this step, compound (I-a) is halogenated with, for example, a chlorinating agent such as acetyl chloride, thionyl chloride and the like or, for example, a brominating agent such as acetyl bromide, phosphorus tribromide, diphenylphosphine/bromine and the like to give a compound represented by the formula (I'-b) (hereinafter to be abbreviated as compound (I'-b)).

Examples of the solvent include halogenated hydrocarbons such as chloroform, dichloromethane, and the like; aromatic hydrocarbons such as toluene, xylene, and the like; ethers such as tetrahydrofuran, dioxane, and the like; and a mixture thereof. Of these, chloroform, tetrahydrofuran, toluene, and the like are preferable.

The reaction temperature is generally 10° C. to 150° C., preferably 30° C. to 80° C., and the reaction time is generally 0.5-30 hr, preferably 2-20 hr.

Step (d-4)

In this step, compound (I'-b) is azidated with an azidating agent such as sodium azide and the like to give a compound represented by the formula (I'-c) (hereinafter to be abbreviated as compound (I'-c)).

The reaction includes reacting compound (I'-b) with an azidating agent in a solvent that does not influence the reaction.

Examples of the solvent include halogenated hydrocarbons such as chloroform, dichloromethane, and the like; aromatic hydrocarbons such as toluene, xylene, and the like; ethers such as tetrahydrofuran, dioxane, and the like; amides such as N,N-dimethylformamide and the like; and a mixture thereof. Of these, chloroform, N,N-dimethylformamide, and the like are preferable.

The reaction temperature is generally 10° C. to 150° C., preferably 20° C. to 100° C., and the reaction time is generally 0.5-30 hr, preferably 2-20 hr.

step (d-5)

In this step, compound (I'-c) is aminated to give compound (I-b).

The reaction is carried out by reacting compound (I'-c) with triphenylphosphine in a solvent that does not influence the reaction in the presence of water or catalytic hydrogenation.

The amount of triphenylphosphine to be used is preferably 1-10 mol, particularly preferably 1-5 mol, per 1 mol of compound (I'-c).

The amount of water to be used is preferably 1-10 mol, particularly preferably 1-5 mol, per 1 mol of compound (I'-c).

Examples of the solvent include aromatic hydrocarbons such as toluene, xylene, and the like; ethers such as tetrahydrofuran, dioxane, and the like; and a mixture thereof. Of these, toluene, tetrahydrofuran, and the like are preferable.

The reaction temperature is generally 10° C. to 150° C., preferably 20° C. to 100° C., and the reaction time is generally 0.5-30 hr, preferably 2-20 hr.

Step (d-6)

In this step, compound (I'-b) is reacted with $RNH_2$ (wherein R is as defined above) to give a compound represented by the formula (I-c) (hereinafter to be abbreviated as compound (I-c)), which is the compound of the present invention wherein Y is an —NHR group.

The reaction includes reacting compound (I'-b) with amine represented by R—$NH_2$ in a solvent that does not influence the reaction in the presence of, where necessary, for example, a base such as tertiary amine (triethylamine, diisopropylethylamine etc.) and the like.

Examples of the solvent include aromatic hydrocarbons such as toluene, xylene, and the like; ethers such as tetrahydrofuran, dioxane, and the like; and, halogen solvents such as chloroform, dichloromethane, and the like and a mixture thereof. Of these, toluene, tetrahydrofuran, chloroform, and the like are preferable.

The reaction temperature is generally 10° C. to 100° C., preferably 20° C. to 60° C., and the reaction time is generally 0.5-30 hr, preferably 2-20 hr.

step (d-7)

In this step, compound (I-d) is reacted with a compound having a —$CONH_2$ group or a —$OCONH_2$ group, and treated with a base to give compound (I-e).

The reaction of compound (I-d) with a compound having a —$CONH_2$ group or a —$OCONH_2$ group is carried out in a solvent that does not influence the reaction and under an acid catalyst.

Examples of the acid catalyst include methanesulfonic acid, trifluoromethanesulfonic acid, toluenesulfonic acid and the like. Of these, methanesulfonic acid and toluenesulfonic acid are preferable.

The amount of the acid catalyst to be used is preferably 0.05-0.5 mol, particularly preferably 0.1-0.3 mol, per 1 mol of compound (I-d).

Examples of the compound having a —$CONH_2$ group or a —$OCONH_2$ group include Fmoc-$NH_2$, $HCONH_2$, $CF_3CONH_2$, Ac$NH_2$, EtO$CONH_2$, Cbz-$NH_2$ and the like. Of these, Fmoc-$NH_2$, EtO$CONH_2$ and the like are preferable.

Here, the "Fmoc-" means a 9-fluorenylmethoxycarbonyl group (hereinafter to be also referred to as a Fmoc group), and "Cbz-" means a benzyloxycarbonyl group (hereinafter to be also referred to as a Cbz group).

The $R_a$ forming-reagent to be used as a starting compound of step (a) [i.e., hydroxide, halide, an alkylsulfonyloxylation product (e.g., methanesulfonyloxylation product etc.) or an arylsulfonyloxylation product (e.g., p-toluenesulfonyloxylation product etc.) corresponding to $R_a$ group] may be a commercially available product. In addition, the $R_a$ forming-reagent can be produced by, for example, (1) halogenation, alkylsulfonyloxylation or arylsulfonyloxylation of hydroxide corresponding to an $R_a$ group, or (2) reduction reaction of unsaturated hydroxide corresponding to an $R_a$ group (e.g., catalytic hydrogenation reaction in the presence of a metal catalyst such as platinum-carbon (Pt/C), palladium-carbon (Pd/C), rhodium-carbon (Rh/C), Raney-nickel etc. and the like), and subsequently halogenation, alkylsulfonyloxylation or arylsulfonyloxylation.

In the production of the $R_a$ forming-reagent, examples of the reagent to be used for conversion to a leaving group from a hydroxyl group include, in addition to halogenating agent such as chlorinating agent (thionyl chloride, N-chlorosuccinimide (NCS) and the like), brominating agent (hydrobromic acid, acetyl bromide, N-bromosuccinimide (NBS), phosphorus tribromide, diphenylphosphine/bromine and the like) and the like, alkylsulfonylating agent such as methanesulfonyl chloride, trifluoromethanesulfonyl chloride and the like, arylsulfonylating agent such as benzenesulfonyl chloride, p-toluenesulfonyl chloride etc. and the like. Of these, thionyl chloride, hydrobromic acid and the like are preferable, which are the halogenating agents.

The reaction is performed in a solvent that does not influence the reaction. Examples of the solvent include water, halogenated hydrocarbons such as chloroform, dichloromethane and the like; aromatic hydrocarbons such as benzene, toluene, xylene and the like; nitriles such as acetonitrile, propionitrile and the like; ethers such as tetrahydrofuran, 1,4-dioxane, diethyl ether and the like. Of these, water, halogenated hydrocarbons such as chloroform and the like are preferable.

The reaction temperature is generally 10-120° C., preferably 50-100° C., and the reaction time is generally 1-72 hr, preferably 3-24 hr.

The compound of the present invention (a compound represented by the formula (I) wherein the aforementioned Q is a single bond) can be also produced by, for example, the following method. That is, introduction of an $R_a$ group onto a benzene ring can be carried out by (1) Friedel-Crafts reaction using halide corresponding to an $R_a$ group (chloride, bromide, or iodide), carboxylic acid or acid halide corresponding to an $R_a$ group, (2) a method comprising subjecting a compound corresponding to the above-mentioned compound (II) (a compound wherein a Q'H group is substituted by a —CHO group) to carbon homologation by a Wittig reaction and, followed by catalytic hydrogenation and the like, or (3) conventional organic synthesis reaction such as cross coupling using a metal catalyst and the like.

In each scheme above, the carbon number of an organic group for $R_a$, the kind of halogen atom, reaction reagents and the like are shown for the sake of convenience, and can be appropriately changed within the scope of the above-mentioned definitions.

[Organic Synthesis Reaction]

The compound of the present invention can be used as a protecting reagent in an organic synthesis reaction of peptide, oligonucleic acid, and other organic compounds. The compound of the present invention is preferably used as a protecting reagent of amino acid or peptide in the peptide synthesis and the like. To be specific, the compound of the present invention is preferably introduced into amino acid or peptide as a protecting group of C-terminal carboxyl group, carboxamido group (amido group), i.e., a —CONHR' group that an amino acid forming a C-terminus has (R' is a hydrogen atom, an alkyl group or an aralkyl group), a functional group such as —SH group and the like, and a side chain functional group (hereinafter C-terminus and the like). The explanations of the alkyl group and aralkyl group for R' are the same as those of the alkyl group and aralkyl group for R. R' is preferably a hydrogen atom. When used as a protecting reagent, the compound of the present invention may be activated or converted to an equivalent before reaction with a substituent to be protected. An "organic compound protected by a branched chain-containing aromatic compound of the present invention" is referred to as a "branched chain-containing aromatic compound adduct".

The compound of the present invention can be used as a protecting reagent for various organic synthesis reactions. For example, organic synthesis reactions can be performed by the following steps:

step (i) a step of dissolving the compound of the present invention in a compound-solubilizing solvent (dissolving step), step (ii) a step of bonding the compound of the present invention dissolved in the solubilizing solvent as obtained in the above-mentioned step to a reaction substrate (bonding step), step (iii): a step of washing the reaction solution containing the bonded product obtained in the above-mentioned step with water, separating the layers and removing the aqueous layer (layer-separating step), step (iv): a step of subjecting the solution after washing with water, which contains the bonded product obtained in the above-mentioned step to a reaction, washing the resultant product after the reaction with water, separating the layers and removing the aqueous layer (reacting and layer-separating step), step (v): a step of removing a protecting group derived from the compound of the present invention and other protecting groups from a resultant product in the solution after washing with water (deprotection step).

In the present specification, the "protecting group derived from the compound of the present invention" and "other protecting group" may be distinguished by referring them as "anchor" and "temporary protecting group", respectively.

Each of the above-mentioned steps is explained in detail in the following.

Step (i) (Dissolving Step)

In this step, the compound of the present invention is dissolved in a compound-solubilizing solvent.

As such solubilizing solvent, general organic solvents can be used for the reaction. Since the compound of the present invention has a long branched chain aliphatic hydrocarbon group, it shows high solubility in various organic solvents and is expected to show a superior reactivity.

Specific examples of the solubilizing solvent include ethers such as diethyl ether, tetrahydrofuran, 1,4-dioxane, methyl-t-butylether, cyclopentylmethylether (CPME) and the like; acetate esters such as ethyl acetate, isopropyl acetate and the like; halogenated hydrocarbons such as chloroform, dichloromethane and the like; aromatic hydrocarbons such as toluene, xylene and the like; and hydrocarbons such as hexane, heptane, cyclohexane and the like. Two or more kinds of these solvents may be used in a mixture at appropriate proportions. Since good extraction operation can be expected, and industrial use is possible, ethyl acetate, isopropyl acetate, dichloromethane, cyclopentylmethylether and toluene are preferable, ethyl acetate, isopropyl acetate, cyclopentylmethylether and toluene are more preferable, ethyl acetate, isopropyl acetate and cyclopentylmethylether are more preferable, and isopropyl acetate and cyclopentylmethylether are further preferable.

While "the solubility of the compound of the present invention in an organic solvent" should be evaluated as "solubility of a bonded product of a substrate such as each starting material and each resultant product in each reaction and the compound of the present invention in an organic solvent", it is extremely difficult to assume and confirm solubility of a bonded product of a substrate and the compound of the present invention for various substrates. Therefore, it was evaluated as "solubility of the compound of the present invention itself in an organic solvent".

In the following, the characteristics of the compound of the present invention are shown by referring to isopropyl acetate as a representative example of the solubilizing solvent.

While the lower limit of saturation solubility of the compound of the present invention in isopropyl acetate (100 g) at 20° C. is not particularly limited as long as the bonding to a reaction substrate and the reaction thereafter proceed, 1 wt % is preferable, 2 wt % is more preferable, 5 wt % is further preferable, 10 wt % is still more preferable, 25 wt % is especially preferable and 50 wt % is particularly preferable, since the reaction proceeds stably with any industrial substrate.

While the upper limit of saturation solubility of the compound of the present invention in isopropyl acetate (100 g) at 20° C. is not particularly limited as long as a reaction solution with a sufficiently high concentration can be obtained, 80 wt % is preferable, 85 wt % is more preferable, 90 wt % is further preferable, and 95 wt % is still more preferable, since the reaction proceeds stably irrespective of the degree of progress of industrial reactions.

The above-mentioned solubilizing solvent may contain various hydrophilic organic solvents so as to improve solubility of a substrate at a reaction time point; improve solubility of unreacted compounds and by-products in an aqueous layer at a time point of extraction (i.e., to facilitate removal of unreacted compounds and by-products); or improve layer-separating ability.

To remove and wash unreacted compounds and by-products at a time point of extraction, various hydrophilic organic solvents may be used instead of water. Specifically, when heptane is used as a reaction solvent, acetonitrile may be used for extraction and washing.

Specific examples of various hydrophilic organic solvents include nitriles such as acetonitrile, propionitrile and the like; ketones such as acetone, methylethyl ketone, 2-butanone and the like; amides such as N,N-dimethylformamide, N-methylpyrrolidone and the like; and sulfoxides such as dimethyl sulfoxide and the like. Acetonitrile, N,N-dimethylformamide, N-methylpyrrolidone are preferable, N,N-dimethylformamide, N-methylpyrrolidone are more preferable, and N-methylpyrrolidone are further preferable, since they aid solubility and do not influence layer-separating ability.

Step (ii) (Bonding Step)

In this step, the compound of the present invention dissolved in a compound-solubilizing solvent, which is obtained in the above-mentioned step (i), is bonded to a reaction substrate.

Here, the reaction substrate has a carboxyl group and the like such as protected amino acid and the like, and the amount of the reaction substrate to be used is 1-10 mol, preferably 1-5 mol, per 1 mol of the compound of the present invention.

When Y is a hydroxyl group, an ester bond can be formed by adding a condensing agent into a solvent that does not influence the reaction in the presence of a dimethylaminopyridine catalyst.

When Y is a group NHR, an amide bond can be formed by adding a condensing agent in the presence of a condensation additive such as 1-hydroxybenzotriazole (HOBt), ethyl 1-hydroxy-1H-1,2,3-triazole-5-carboxylate (HOCt), 1-hydroxy-7-azabenzotriazole (HOAt), 3,4-dihydro-3-hydroxy-4-oxo-1,2,3-benzotriazine (HOOBt) and the like.

When Y is a halogen atom, an ester bond can be formed by adding a base such as diisopropylethylamine and the like into a solvent that does not influence the reaction.

The amount of the condensing additive to be used is not particularly limited as long as the reaction proceeds, and is preferably 0.05-1.5 mol per 1 mol of the compound of the present invention.

While the condensing agent is not particularly limited as long as the reaction proceeds, specific examples of the condensing agent include dicyclohexylcarbodiimide (DCC), diisopropylcarbodiimide (DIC), N-ethyl-N'-3-dimethylaminopropylcarbodiimide and hydrochloride thereof (EDC HCl), hexafluorophosphoric acid (benzotriazol-1-yloxy) tripyrrolizinophosphonium (PyBop), O-(benzotriazol-1-yl)-N,N,N',N'-tetramethyluronium tetrafluoroborate (TBTU), 1-[bis(dimethylamino)methylene]-5-chloro-1H-benzotriazolium 3-oxide hexafluorophosphate (HCTU), O-benzotriazole-N,N,N',N'-tetramethyluronium hexafluoroborate (HBTU), and the like.

The amount of the condensing agent to be used can be 1-mol, preferably 1-5 mol, per 1 mol of the compound of the present invention.

As the solvent, the aforementioned solubilizing solvent is preferable.

The reaction temperature is generally −10° C. to 30° C., preferably 0° C. to 20° C., and the reaction time is generally 1-hr.

For confirmation of the progress of the reaction, a method similar to general liquid phase organic synthesis reaction can be applied. That is, thin layer silica gel chromatography, high performance liquid chromatography and the like can be used to track the reaction.

Step (iii) (Layer-Separating Step)

In this step, a reaction solution containing a bonded product obtained in the above-mentioned step (ii) is added with water (and/or hydrophilic organic solvent such as acetonitrile and the like), and the mixture is stirred, washed, and a water-soluble reaction residue (and/or reaction residue soluble in hydrophilic organic solvent) is removed by layer-separation (liquid-separating operation).

Step (iv) (Reacting and Layer-Separating Step)

In this step, a desired organic synthesis reaction is performed in an organic solution containing a bonded product obtained in the above-mentioned step (iii) after washing with water, and the resultant product obtained by the organic synthesis reaction is crudely purified by adding water to a reaction solution containing the resultant product dissolved therein, and the mixture is stirred, washed, and a water-soluble reaction residue is removed by layer-separation (liquid-separation operation).

Step (v) (Deprotecting Step)

In this step, a protecting group derived from the compound of the present invention (anchor) alone, or simultaneously the anchor and a temporary protecting group is/are finally removed from the resultant product contained in a solution after layer-separating step in the above-mentioned step (iv) to give the objective product.

The anchor to be removed here is a group represented by the formula (I-f):

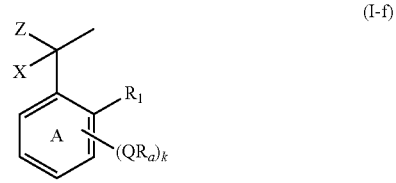

wherein each group is as defined above.

When Y is a hydroxyl group or a halogen atom, the compound of the present invention reacts with a carboxyl group of the first reaction substrate to form an ester bond. In this case, deprotection of anchor converts the C-terminus of the peptide to a carboxyl group.

When Y is an —NHR group, the compound of the present invention reacts with a carboxyl group of the first reaction substrate to form an amide bond. In this case, deprotection of anchor converts the C-terminus of the peptide to a —CONHR group.

In this step, only an anchor can be selectively removed without removing the temporary protecting group. For example, the compound of the present invention (anchor) wherein X and Z are each a hydrogen atom, Y is a hydroxyl group, and group $QR_a$(particularly $OR_a$) on the benzene ring is present at the 2-position and the 4-position, or the 2-position, the 4-position and the 6-position is used, and when the temporary protecting group of peptide and the like is an Fmoc group or Cbz group, the deprotection is preferably performed by an acid treatment.

Examples of the acid to be used include trifluoroacetic acid (hereinafter to be referred to as TFA), hydrochloric acid, sulfuric acid, methanesulfonic acid, p-toluenesulfonic acid and the like, with preference given to TFA. The deprotection is preferably performed under solution conditions using a solution such as chloroform, dichloromethane and THF, having an acid concentration of 0.1%-5%.

It is also possible to remove a protecting group (anchor) derived from the compound of the present invention simultaneously with a temporary protecting group. In this case, a method conventionally used in the pertinent field, particularly peptide synthesis, is used, with preference given to a method including hydrogen reduction conditions, acidic conditions and the like. As an acid, TFA, hydrochloric acid, sulfuric acid, mesylic acid, tosylic acid, trifluoroethanol, hexafluoroisopropanol and the like can be used. Of these, TFA is particularly preferable.

The amount of the acid to be used is appropriately determined depending on the kind of the acid to be used, and an amount suitable for removing the anchor is used. The amount that can be used is 3-100 mol, preferably 5-50 mol, per 1 mol of the bonded product. When the above-mentioned TFA is used, trifluoromethanesulfonic acid, trimethylsilyl trifluoromethanesulfonate, boron trifluoride etherate ($BF_3$ $Et_2O$) and the like can also be added as a further strong acid source.

The reaction temperature is generally 0° C.-80° C., preferably 0° C.-30° C.

The reaction time is generally 0.5-24 hr.

By utilizing the above-mentioned steps, peptide can be produced. The compound of the present invention can be mainly used as, but is not limited to, a protecting reagent for C-terminus and the like of amino acid or peptide. In addition, since the compound of the present invention wherein Y is a hydroxyl group can be converted to a corresponding chloroformate form by a method conventionally used in the pertinent field, for example, reaction with phosgene, the chloroformate form can also be used as a protecting reagent of N-terminus and the like.

A method of producing a peptide utilizing the above-mentioned steps, comprising the following steps;
(1) a step of condensing the compound of the present invention with a C-terminus and the like of an N-protected amino acid or an N-protected peptide in a solvent solubilizing the compound to give an N-protected C-protected amino acid or N-protected C-protected peptide having a C-terminus protected with an anchor (protecting step of C-terminus and the like),
(2) a step of removing the N-terminal protecting group from the obtained N-protected C-protected amino acid or N-protected C-protected peptide to give a C-protected amino acid or C-protected peptide (N-terminal deprotecting step),
(3) a step of condensing an N-protected amino acid or N-protected peptide with the N-terminus of the obtained C-protected amino acid or C-protected peptide to give an N-protected C-protected peptide (peptide chain elongating step), and
(4) a step of removing the N-terminal protecting group and the C-terminal anchor from the obtained N-protected C-protected peptide to give an objective peptide (deprotecting step).

In the present invention, the "N-protected amino acid" and "N-protected peptide" mean amino acid and peptide wherein the N-terminal amino group is protected with a temporary protecting group, and the C-terminal carboxyl group is not protected, respectively. These are sometimes indicated as "P-AA-OH" etc. below (P is an N-terminal protecting group).

In the present invention, the "N-protected C-protected amino acid" and "N-protected C-protected peptide" mean amino acid and peptide wherein the N-terminal amino group is protected with a temporary protecting group, and the C-terminal carboxyl group is protected with anchor, respectively.

In the present invention, the "C-protected amino acid" and "C-protected peptide" mean amino acid and peptide wherein the N-terminal amino group is not protected, and the C-terminal carboxyl group is protected with anchor, respectively.

Step (1) (Protecting Step of C-Terminus and the Like)

In this step, the compound of the present invention is condensed with C-terminus and the like of N-protected amino acid or N-protected peptide in a compound-solubilizing solvent to give an N-protected C-protected amino acid or N-protected C-protected peptide. This step can be performed according to, for example, the above-mentioned step (ii) and step (iii).

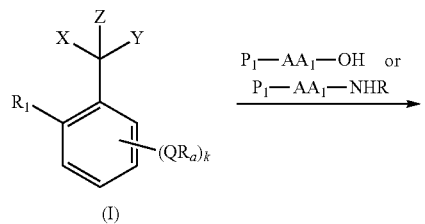

P$_1$—AA$_1$—OH or
P$_1$—AA$_1$—NHR

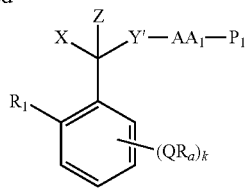

wherein P$_1$ is an N-terminal amino-protecting group, AA$_1$ is a group derived from amino acid, Y' is O or NR and other symbols are as defined above.

The condensation reaction of the compound of the present invention and C-terminus of N-protected amino acid or N-protected peptide is preferably performed in a solvent that does not influence the reaction. For example, when Y is a hydroxyl group or —NHR group, the condensation reaction is performed in the presence of a condensing agent, and when Y is a halogen atom, the condensation reaction is performed in the presence of a base. As a result, when Y is hydroxyl or a halogen atom, an ester bond is formed, and when Y is an —NHR group, an amide bond is formed. Examples of the condensing agent include dicyclohexylcarbodiimide, diisopropylcarbodiimide, N-ethyl-N'-3-dimethylaminopropylcarbodiimide and a hydrochloride thereof (EDC HCl), and the like. An ester bond forming reaction is performed in the presence of dimethylaminopyridine, and an amide bond forming reaction is performed in the presence of a condensation additive such as HOBt, HOCt and the like.

As the solvent to be used for this step, the aforementioned solubilizing solvents are preferable. The amount of the solvent to be used is preferably 2-50 ml per 1 g of the compound of the present invention.

According to the length and kind of the peptide chain, moreover, toluene, cyclopentylmethylether, chloroform and the like can be selected as a solvent. Two or more kinds of these solvents may be used in a mixture.

The reaction temperature is generally −10° C. to 40° C., preferably 0° C.-30° C. The reaction time is generally 1-70 hr.

After completion of the reaction, the reaction mixture is washed with water and the layers are separated to give a solution containing the objective C-protected amino acid or C-protected peptide, which can be directly used for the next step without isolation.

The compound of the present invention wherein Y is a hydroxyl group and an amide compound represented by P$_1$-AA$_1$-NHR (e.g., Fmoc-Ala-NH$_2$, Fmoc-Gly-NH$_2$ etc.) are treated at a high temperature (preferably, 50° C.-150° C., more preferably 60° C.-120° C.) under an acid catalyst (e.g., methanesulfonic acid, trifluoromethanesulfonic acid, p-toluenesulfonic acid etc.) in a solvent that does not influence the reaction, whereby a compound protected with anchor by an amide bond can also be obtained.

Step (2) (N-Terminal Deprotecting Step)

In this step, the N-terminal protecting group is removed from the N-protected C-protected amino acid or N-protected C-protected peptide obtained in step (1) to give C-protected amino acid or C-protected peptide.

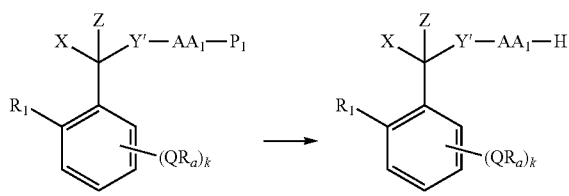

wherein each symbol is as defined above.

As the protecting group of the N-terminus, the below-mentioned amino-protecting groups generally used in the technical field of peptide chemistry and the like are usable. In the present invention, a tert-butoxycarbonyl group (hereinafter to be also referred to as Boc group), a Cbz group and/or an Fmoc group are/is preferably used.

While the deprotection conditions are appropriately selected depending on the kind of the N-terminal protecting group, deprotection conditions different from anchor removal are preferable. For example, when the N-terminal protecting group is an Fmoc group, it is treated with a base (e.g., dimethylamine, diethylamine, piperidine, morpholine, DBU, diethylenetriamine, aminomethylpiperidine, triethylenetetramine, tetraethylenepentamine etc.) (see WO2009/014177); when it is a Cbz group, catalytic reduction is performed; and when it is a Boc group, it is treated with an acid (see WO2009/014176). The reaction is performed in a solvent that does not influence the reaction (e.g., the aforementioned solubilizing solvents). After completion of the reaction, a layer-separating extraction is performed to give a solution containing the objective deprotection form, which can be directly used for the next step without isolation.

Step (3) (Peptide Chain Elongating Step)

In this step, the N-terminus of the C-protected amino acid or C-protected peptide obtained in step (2) is condensed with N-protected amino acid or N-protected peptide to give N-protected C-protected peptide, which can be performed according to, for example, step (iv).

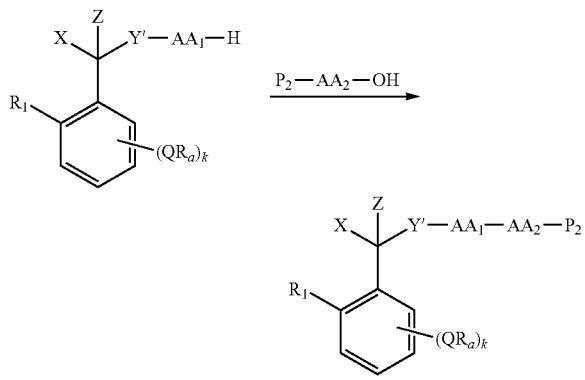

wherein $P_2$ is an N-terminal amino-protecting group, $AA_2$ is a group derived from amino acid, and other symbol is as defined above.

This step is performed by using the condensing agent, condensation additive and the like described in the aforementioned step (1) and under peptide synthesis conditions generally used in the field of peptide chemistry.

After completion of the reaction, the reaction mixture is washed with water and/or hydrophilic organic solvent (acetonitrile, DMF etc.) and the layers are separated to give a solution containing N-protected C-protected peptide, which can be directly used for the next step without isolation.

Step (4) (Deprotecting Step)

In this step, the N-terminal protecting group and C-terminal anchor are removed from the N-protected C-protected peptide obtained in step (3) to give the objective peptide, which can be performed according to, for example, the deprotecting step of N-terminal protecting group in the above-mentioned step (2), and step (v).

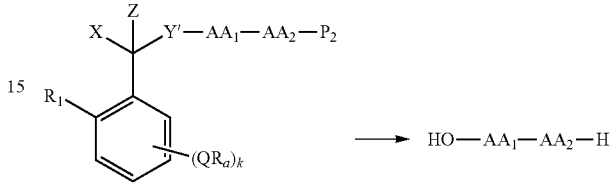

wherein each symbol is as defined above.

In the production method of the peptide of the present invention, the N-protected C-protected peptide obtained in step (3) may be subjected to one or more repetitions of steps (5), (6), and (7) or (7'), followed by step (4):

(5) a step of removing the N-terminal protecting group of the obtained N-protected C-protected peptide to give a C-protected peptide (N-terminal deprotecting step), (6) a step of condensing N-protected amino acid or N-protected peptide with the N-terminus of the obtained C-protected peptide to give an N-protected C-protected peptide (peptide chain elongating step), (7) a step of adding water to the reaction system after step (6), and separating the impurity by extraction into an aqueous layer (extraction separation step), or (7') a step of adding a hydrophilic organic solvent to the reaction system after step (6), and separating the impurity by extracting into a hydrophilic organic solvent layer (extraction separation step).

Step (5) (N-Terminal Deprotecting Step)

This step is performed in the same manner as in the above-mentioned step (2).

Step (6) (Peptide Chain Elongating Step)

This step is performed in the same manner as in the above-mentioned step (3).

Steps (7), (7') (Extraction Separation Step)

In this step, N-protected C-protected peptide obtained in step (6) is left in the organic layer by layer-separation, impurity and the like produced by condensation reaction are removed into an aqueous layer and/or a hydrophilic organic solvent (acetonitrile, DMF etc.) layer.

When the organic synthesis reaction or peptide synthesis reaction of the present invention contains multi-steps, an isolation step may be added as appropriate between the steps, and the aforementioned layer-separating step such as extraction, washing and the like may be appropriately omitted as long as the reaction in the next step is not influenced.

In each reaction, when the starting compound has a hydroxy group, an amino group, a carboxyl group or a carbonyl group (particularly when amino acid or peptide has a functional group in the side chain), a protecting group generally used in the peptide chemistry and the like may be introduced into these groups, and the objective compound can be obtained by removing the protecting group as necessary after the reaction.

Examples of the hydroxyl-protecting group include ($C_1$-$C_6$)alkyl group (e.g., methyl, ethyl, propyl, isopropyl, butyl, tert-butyl), phenyl group, trityl group, (C$_7$-C$_{10}$)aralkyl group (e.g., benzyl), formyl group, (C$_1$-C$_6$)alkyl-carbonyl group (e.g., acetyl, propionyl), benzoyl group, (C$_7$-C$_{10}$)aralkyl-carbonyl group (e.g., benzylcarbonyl), 2-tetrahydropyranyl group, 2-tetrahydrofuranyl group, silyl group (e.g., trimethylsilyl, triethylsilyl, dimethylphenylsilyl, tert-butyldimethylsilyl, tert-butyldiethylsilyl), (C$_2$-C$_6$)alkenyl group (e.g., 1-allyl), N-(acetyl)aminomethyl group (Acm) and the like. These groups are optionally substituted by 1 to 3 substituents selected from a halogen atom (e.g., fluorine, chlorine, bromine, iodine), a (C$_1$-C$_6$)alkyl group (e.g., methyl, ethyl, propyl), a (C$_1$-C$_6$)alkoxy group (e.g., methoxy, ethoxy, propoxy), a nitro group and the like.

Examples of the amino-protecting group include a formyl group, a (C$_1$-C$_6$)alkyl-carbonyl group (e.g., acetyl, propionyl), a (C$_1$-C$_6$) alkoxy-carbonyl group (e.g., methoxycarbonyl, ethoxycarbonyl, a Boc group), a benzoyl group, a (C$_7$-C$_{10}$)aralkyl-carbonyl group (e.g., benzylcarbonyl), a (C$_7$-C$_{14}$)aralkyloxy-carbonyl group (e.g., a CBz group, a chlorobenzyloxycarbonyl group, a bromobenzyloxycarbonyl group, a Fmoc group), a trityl group, a phthaloyl group, a N,N-dimethylaminomethylene group, a silyl group (e.g., trimethylsilyl, triethylsilyl, dimethylphenylsilyl, tert-butyldimethylsilyl, tert-butyldiethylsilyl), a (C$_2$-C$_6$)alkenyl group (e.g., 1-allyl) and the like. These groups are optionally substituted by 1 to 3 substituents selected from a halogen atom (e.g., fluorine, chlorine, bromine, iodine), a (C$_1$-C$_6$) alkoxy group (e.g., methoxy, ethoxy, propoxy), a nitro group and the like.

Examples of the carboxyl-protecting group include a (C$_1$-C$_6$)alkyl group (e.g., methyl, ethyl, propyl, isopropyl, butyl, tert-butyl), a (C$_7$-C$_{10}$)aralkyl group (e.g., benzyl, bromobenzyl, chlorobenzyl, nitrobenzyl), a phenyl group, a trityl group, a silyl group (e.g., trimethylsilyl, triethylsilyl, dimethylphenylsilyl, tert-butyldimethylsilyl, tert-butyldiethylsilyl, tert-butyldiphenylsilyl), a (C$_2$-C$_6$)alkenyl group (e.g., 1-allyl) and the like. These groups are optionally substituted by 1 to 3 substituents selected from a halogen atom (e.g., fluorine, chlorine, bromine, iodine), a (C$_1$-C$_6$) alkoxy group (e.g., methoxy, ethoxy, propoxy), a nitro group and the like.

Examples of the carbonyl-protecting group include cyclic acetal (e.g., 1,3-dioxane), acyclic acetal (e.g., di-(C$_1$-C$_6$) alkylacetal) and the like.

These protecting groups can be removed by a method known per se, for example, the method described in Protective Groups in Organic Synthesis, John Wiley and Sons (1980) and the like. For example, a method using acid, base, ultraviolet rays, hydrazine, phenylhydrazine, sodium N-methyldithiocarbamate, tetrabutylammonium fluoride, palladium acetate, trialkylsilylhalide (e.g., trimethylsilyliodide, trimethylsilylbromide and the like) and the like, a reduction method and the like are used.

[Kit for Production of Peptide]

The present invention also provides a kit for production of peptide, which contains the compound of the present invention as an essential constituent component. The kit may contain, besides the compound of the present invention, other components necessary for production of peptide, for example, various solvents used for the reaction, amino acid (or peptide) to be the starting material and the like. When desired, a manual of production of peptide using the compound of the present invention can also be attached.

EXAMPLES

Other features of the invention will become apparent in the course of the following descriptions of exemplary embodiments which are given for illustration of the invention and are not intended to be limiting thereof. The reagents, apparatuses and materials used in the present invention are commercially available unless otherwise specified. In the present specification, when amino acid and the like are indicated by abbreviation, each indication is based on the abbreviation of the IUPAC-IUB Commission on Biochemical Nomenclature or conventional abbreviations in the art.

The yield in the following Reference Examples and Examples is in mol/mol %. Unless particularly indicated, "%" in the present specification means "wt %". The ratio of solvents in the following Reference Examples and Examples is volume ratio. $^1$H-NMR spectrum was measured using tetramethylsilane as an internal standard, and CDCl$_3$ as a measuring solvent. NMR spectrum was measured using Bruker AVANCE AV300 (300 MHz) nuclear magnetic resonance apparatus.

For electrospray ionization liquid chromatography/mass spectrometry (hereinafter to be abbreviated as LC/MS), LC-MSD (liquid chromatography) system 1100 Series (Agilent Technologies) was used and flow injection analysis (FIA) was performed (solvent: 0.05% TFA THF water, ionization mode: ESI, ion mode: positive, mass spectrometry part: quadrupole, fragmenter voltage: 100V).

Reference Example 1

Synthesis of 2,3-Dihydrophytol

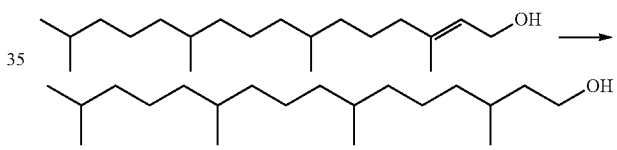

Phytol (10.00 g, 33.7 mmol) was dissolved in methanol, Pt/C (2%, 1.00 g) was suspended therein and the suspension was stirred overnight under a hydrogen atmosphere. After completion of the reaction, the suspension was filtered to remove Pt/C, and the filtrate was concentrated to give 2,3-dihydrophytol. This was used for the next reaction without purification.

$^1$H-NMR (300 MHz): δ0.80-0.93 (15H, m, Ne), 0.98-1.70 (24H, br, m, Me$_2$C$\underline{H}$—[C$_3$$\underline{H}_6$—C$\underline{H}$Me]$_3$-CH$_2$CH$_2$—OH), 3.62-3.75 (2H, —C$\underline{H}_2$—OH).

Reference Example 2

Synthesis of 2,3-Dihydrophytyl Bromide

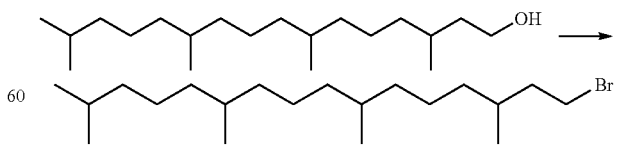

2,3-Dihydrophytol (33.7 mmol) was suspended in 48% hydrobromic acid (100 ml), concentrated sulfuric acid (0.17 ml) was added dropwise and the mixture was stirred at 100° C. overnight. The reaction mixture was cooled to room temperature, extracted with hexane (200 ml), and washed twice with 5% aqueous sodium hydrogen carbonate solution (70 ml) and once with 20% brine (70 ml). The organic layer was dried over sodium sulfate, and the solvent of the filtrate was evaporated. The obtained residue was purified by silica gel column chromatography (short column, hexane alone) to give 2,3-dihydrophytyl bromide ("2,3-dihydrophytyl group" is sometimes to be referred to as "Phy" hereunder) (10.41 g, 28.8 mmol, 85% vs. phytol).

$^1$H-NMR (300 MHz): δ0.79-0.92 (15H, m, Me), 0.95-1.95 (24H, br, m, Me$_2$C$\underline{H}$—[C$_3$H$_6$—C$\underline{H}$Me]$_3$-C$\underline{H}_2$CH$_2$—Br), 3.35-3.52 (2H, —C$\underline{H}_2$—Br).

Reference Example 3

Synthesis of 3,7,11-trimethyldodecan-1-ol

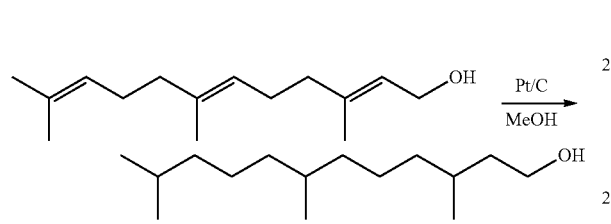

Farnesol (3.00 g, 13.5 mmol) was dissolved in methanol (30 ml), Pt/C (2%, 0.30 g) was suspended therein and the suspension was stirred overnight under a hydrogen atmosphere. After completion of the reaction, Pt/C was removed by filtration, and the filtrate was concentrated to give 3,7,11-trimethyldodecan-1-ol. This was used for the next reaction without purification.

$^1$H-NMR (300 MHz): δ1.09-1.43 (m, 24H), 1.48-1.66 (m, 5H), 3.63-3.70 (m, 2H).

Reference Example 4

Synthesis of 1-bromo-3,7,11-trimethyldodecane

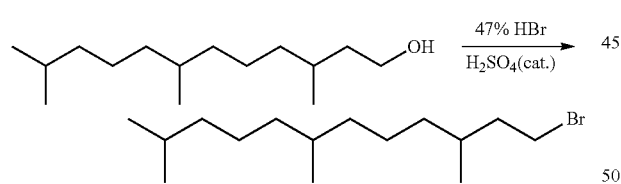

3,7,11-Trimethyldodecan-1-ol obtained in Reference Example 3 was suspended in 48% hydrobromic acid (31 ml), concentrated sulfuric acid (57 μl) was added dropwise and the mixture was stirred at 120° C. overnight. The reaction mixture was cooled to room temperature, extracted with hexane (45 ml), and washed twice with 5% aqueous sodium hydrogen carbonate solution (20 ml) and once with 20% brine (20 ml). The organic layer was dried over sodium sulfate, and the solvent of the filtrate was evaporated. The obtained residue was purified by silica gel column chromatography (short column, hexane alone) to give 1-bromo-3,7,11-trimethyldodecane (2.98 g, 10.2 mmol, 76% vs. Farnesol).

$^1$H-NMR (300 MHz): δ1.12-1.43 (m, 24H), 1.48-1.70 (m, 4H), 1.84-1.90 (m, 1H), 3.36-3.49 (m, 2H).

Reference Example 5

Conversion of GI-1000 (Manufactured by Nippon Soda Co., Ltd.) (Terminal Diol Product; Number Average Molecular Weight: About 1500; n=about 23) to Dibromide Product (GI-1000(Br))

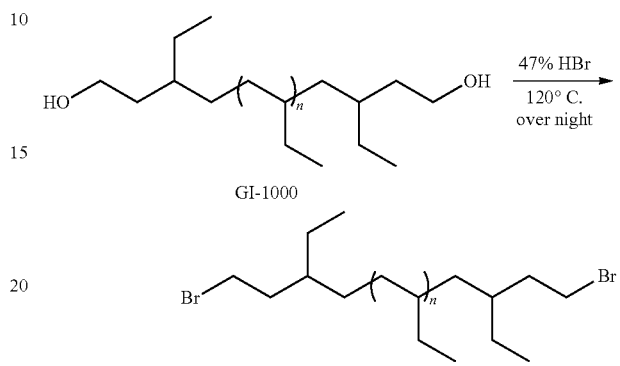

GI-1000 (manufactured by Nippon Soda Co., Ltd.) (5.02 g) was dissolved in heptane (50 ml), and the mixture was washed twice with 80% aqueous acetonitrile solution (25 ml). The heptane layer was concentrated and the obtained residue was suspended in 48% hydrobromic acid (50 ml). Concentrated sulfuric acid (100 μl) was added dropwise and the mixture was stirred at 120° C. overnight. The reaction mixture was cooled to room temperature, extracted with heptane (100 ml), and washed twice with 5% aqueous sodium hydrogen carbonate solution (25 ml), once with 20% brine (25 ml) and twice with 90% aqueous acetonitrile solution (40 ml). The solvent of the filtrate was evaporated. The obtained residue was purified by silica gel column chromatography (short column, hexane alone) to give GI-1000 dibromide (GI-1000(Br)) (2.63 g).

$^1$H-NMR (300 MHz): δ0.90-1.06 (m), 1.83-1.86 (m, 4H), 3.38-3.44 (m, 4H).

Reference Example 6

Conversion of GI-2000 (Manufactured by Nippon Soda Co., Ltd.) (Terminal Diol Product; Number Average Molecular Weight: About 2100; n=about 34) to Dibromide Product (GI-2000(Br))

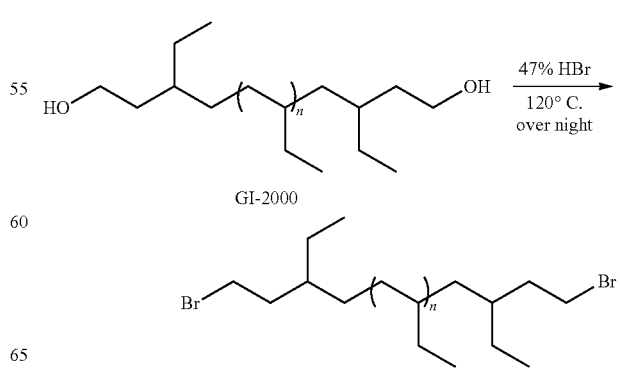

GI-2000 (manufactured by Nippon Soda Co., Ltd.) (5.33 g) was dissolved in heptane (50 ml), and the mixture was washed twice with 80% aqueous acetonitrile solution (25 ml). The heptane layer was concentrated and the obtained residue was suspended in 48% hydrobromic acid (50 ml). Concentrated sulfuric acid (100 μl) was added dropwise and the mixture was stirred at 120° C. overnight. The reaction mixture was cooled to room temperature, extracted with heptane (100 ml), and washed twice with 5% aqueous sodium hydrogen carbonate solution (25 ml), once with 20% brine (25 ml), and twice with 90% aqueous acetonitrile solution (40 ml). The solvent of the filtrate was evaporated. The obtained residue was purified by silica gel column chromatography (short column, hexane alone) to give GI-2000 dibromide (GI-2000(Br)) (2.83 g).

$^1$H-NMR (300 MHz): δ0.91-1.54 (m), 1.81-1.88 (m, 4H), 3.38-3.42 (m, 4H).

Reference Example 7

Conversion of TERGITOL (Registered Trade Mark)-TMN6 (Manufactured by Sigma-Aldrich Corporation) (Commercially Available Product (Number Average Molecular Weight: 543; n=about 5) was Pre-Treated as Shown Below (n: about 7) and Used) to Bromide Product (TERGITOL(Br))

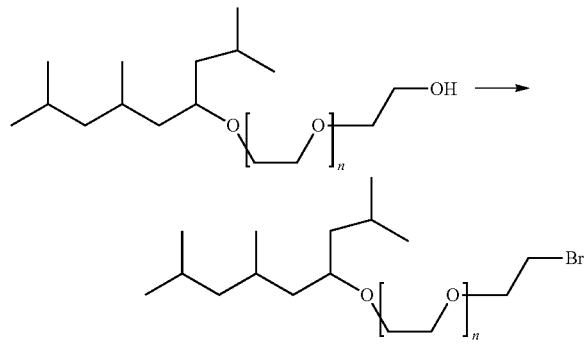

TERGITOL-TMN6 (7.42 g) was dissolved in chloroform (70 ml), and washed with water (35 ml). The extracted organic layer was dried over sodium sulfate, concentrated to dryness and dissolved in chloroform (70 ml). PBr$_3$ (1148 μl, 12.1 mmol, 1.0 eq) and pyridine (1074 μl, 12.1 mmol, 1.0 eq) were added dropwise under ice-cooling, and the mixture was stirred at room temperature for 4 hr. The solvent was removed, the residue was dissolved in ethyl acetate (100 ml), and the mixture was washed three times with 0.5N hydrochloric acid (50 ml), three times with 5% aqueous sodium hydrogen carbonate solution (50 ml), and once with 20% brine (50 ml). The solvent was removed, and the residue was purified by silica gel column chromatography (ethyl acetate-*ethyl acetate:methanol=1:1) The solvent was removed, and the residue was dissolved in ethyl acetate (100 ml), and silica gel was filtered off to give a Br substitution product (5.21 g) of TERGITOL-TMN6.

$^1$H-NMR (300 MHz): δ0.80-0.90 (m, 15H, CH$_3$), 1.00-1.60 (m, 11H, CH, CH$_2$), 3.37-3.47 (m, 3H, CH—O, CH$_2$—Br), 3.50-3.68 (m, (OCH$_2$CH$_2$)$_n$), 3.79-3.83. (t, 2H, O CH$_2$CH$_2$—Br).

$^{13}$C-NMR: δ20.42-27.39 (CH$_3$, CH), 30.81 (CH$_2$—Br), 42.78-47.67 (CH$_2$), 68.04 (OCH$_2$), 70.79-71.55 (OCH$_2$CH$_2$O).

Example 1

Synthesis of 2,4-(2',3'-dihydrophytyloxy)benzyl alcohol

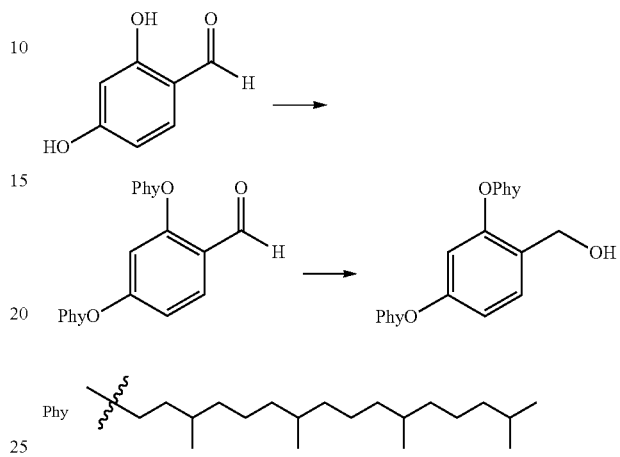

2,3-Dihydrophytyl bromide (4.50 g, 12.5 mmol), 2,4-dihydroxybenzaldehyde (851 mg, 6.16 mmol) and potassium carbonate (2.58 g, 18.7 mmol) were suspended in DMF (45 ml), and the suspension was stirred overnight at 90° C. The reaction mixture was cooled to room temperature, extracted with ethyl acetate (150 ml), and washed three times with 1N hydrochloric acid (50 ml), three times with 5% aqueous sodium hydrogen carbonate solution (50 ml) and once with 20% brine (50 ml). The organic layer was dried over sodium sulfate, and the solvent of the filtrate was evaporated. The obtained residue was purified by silica gel column chromatography (short column, hexane:ethyl acetate=20:1) to give 2,4-(2',3'-dihydrophytyloxy)benzaldehyde (3.65 g, 5.22 mmol, 85% vs. 2,4-dihydroxybenzaldehyde).

The aforementioned 2,4-(2',3'-dihydrophytyloxy)benzaldehyde (3.65 g, 5.22 mmol) was dissolved in THF-methanol mixed solution (40+2 ml), sodium borohydride (263 mg, 90%, 6.26 mmol) was added at 0° C., and the mixture was stirred at room temperature for 1 hr. The reaction mixture was cooled to 0° C. and the reaction was quenched with 1N hydrochloric acid (5 ml). Ethyl acetate (100 ml) was added, and the mixture was washed twice with 1N hydrochloric acid (30 ml), once with 5% aqueous sodium hydrogen carbonate solution (30 ml), and once with 20% brine (30 ml). The organic layer was dried over sodium sulfate, and the solvent of the filtrate was evaporated. The obtained residue was purified by silica gel column chromatography (short column, hexane:ethyl acetate=10:1) to give 2,4-(2', 3'-dihydrophytyloxy)benzyl alcohol (3.29 g, 4.69 mmol, 90%).

$^1$H-NMR (300 MHz): δ0.81-0.90 (24H, m, Me(Phytyl)), 0.94 (6H, dd, J=2.1, 6.3 Hz, Me(Phytyl)), 1.00-1.95 (48H, br, m, Me$_2$CH—[C$_3$H$_6$—CHMe]$_3$-CH$_2$CH$_2$—O—Ar), 2.23 (1H, t, J=6.6 Hz, OH), 3.93-4.07 (4H, m, —CH$_2$—O—Ar), 4.61 (2H, d, J=6.6 Hz, Ar—CH$_2$—OH), 6.43 (1H, dd, J=2.1, 8.1 Hz, C5-H), 6.46 (1H, d, J=2.1 Hz, C3-H), 7.13 (1H, d, J=8.1 Hz, C6-H).

Example 2

Synthesis of 2-chloro-5-(2',3'-dihydrophytyloxy)benzhydrol

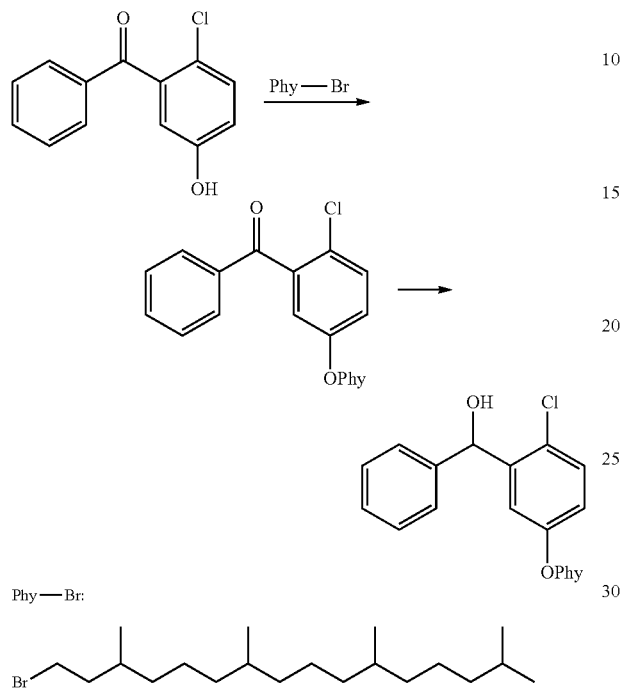

To dihydrophytyl bromide (1.02 g, 2.82 mmol) were added DMF (15 ml), 2-chloro-5-hydroxybenzophenone (0.99 g, 4.23 mmol) and $K_2CO_3$ (0.78 g, 5.64 mmol), and the mixture was stirred at 90° C. for 3 hr. The reaction mixture was cooled to room temperature, ethyl acetate (25 ml) and 1N hydrochloric acid (25 ml) were added and the mixture was stirred to allow layer-separation. The aqueous layer was separated and discarded. The organic layer was washed twice with purified water (25 ml), and the organic layer was evaporated under reduced pressure to give 2-chloro-5-(2',3'-dihydrophytyloxy)benzophenone.

$^1$H-NMR (300 MHz): δ0.75-0.90 (15H, m, M̲e̲), 0.95-1.70 (24H, br, $Me_2CH̲$—$[C_3H̲_6$—$CH̲Me]_3$-C H̲$_2CH_2$—O—Ar), 3.82-3.92 (2H, br, —O—CH̲$_2$—$C_{19}H_{39}$), 6.89 (1H, d, J=8.3 Hz, C3-H̲), 7.35-7.80 (7H, m, C4, 6-H̲, Ph-H̲).

To the aforementioned 2-chloro-5-(2',3'-dihydrophytyloxy)benzophenone were added chloroform (20 ml), methanol (2 ml) and sodium borohydride (440 mg, 11.6 mmol), and the mixture was stirred at 50° C. overnight. The reaction mixture was cooled to room temperature, 1N hydrochloric acid (15 ml) was added dropwise in an ice bath to decompose unreacted sodium borohydride. The aqueous layer was discarded, and the organic layer was washed twice with purified water (10 ml). The organic layer was evaporated under reduced pressure, and moisture was azeotropically distilled with acetonitrile to give 2-chloro-5-(2',3'-dihydrophytyloxy)benzhydrol.

$^1$H-NMR (300 MHz): δ0.82-0.90 (15H, m, M̲e̲), 1.00-1.90 (24H, br, $Me_2CH̲$—$[C_3H̲_6$—$CH̲Me]_3$-C H̲$_2CH_2$—O—Ar), 3.88-4.00 (2H, br, —O—CH̲$_2$—$C_{19}H_{39}$), 5.98 (1H, s, Ar—CH̲OH-Ph), 6.75-6.90 (1H, m, C3-H̲), 7.10-7.45 (7H, m, C4, 6-H̲, Ph-H̲).

Example 3

Synthesis of 1-[(2-chloro-5-(2',3'-dihydrophytyloxy)phenyl)]-1-phenylmethanamine

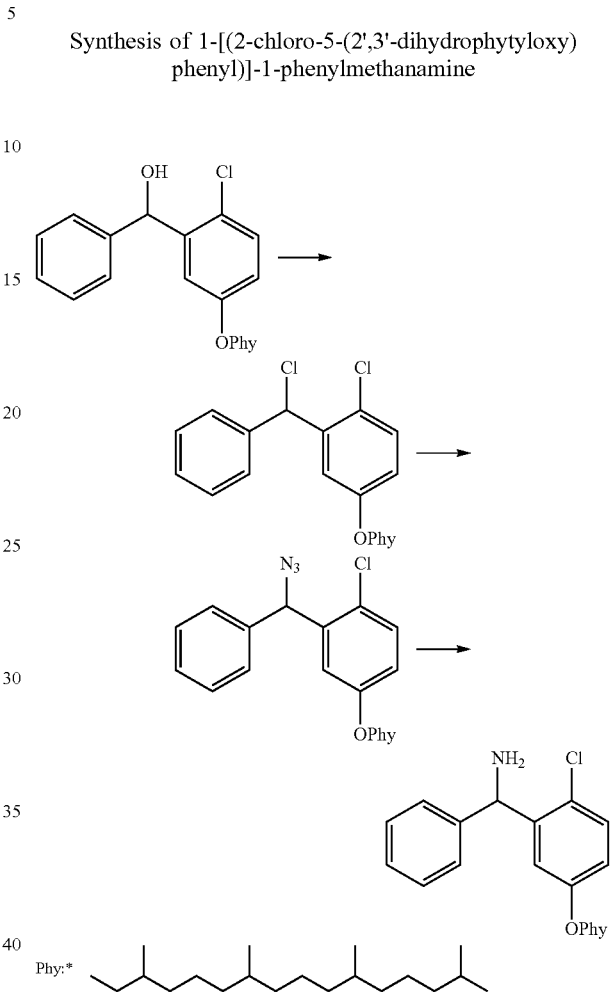

To 2-chloro-5-(2',3'-dihydrophytyloxy)benzhydrol obtained in Example 2 were added chloroform (20 ml), DMF (43 μl, 559 mol) and thionyl chloride (1.03 ml, 14.1 mmol), and the mixture was stirred at 50° C. for 4 hr. The reaction mixture was cooled to room temperature. The solvent was evaporated under reduced pressure, and the remaining thionyl chloride was azeotropically distilled with toluene to give 1-chloro-1-[(2-chloro-5-(2',3'-dihydrophytyloxy)phenyl)phenylmethane.

$^1$H-NMR (300 MHz): δ0.80-0.90 (15H, m, M̲e̲), 1.00-1.90 (24H, br, $Me_2CH̲$—$[C_3H̲_6$—$CH̲Me]_3$-C H̲$_2CH_2$—O—Ar), 3.88-4.05 (2H, m, —O—CH̲$_2$—$C_{19}H_{39}$), 6.48 (1H, d, J=1.6 Hz, Ar—CH̲Cl-Ph), 6.77 (1H, d, J=8.7 Hz, C3-H̲), 7.10-7.55 (7H, m, C4, 6-H̲, Ph-H̲).

To the aforementioned 1-chloro-1-[(2-chloro-5-(2',3'-dihydrophytyloxy)phenyl)phenylmethane were added DMF (15 ml) and sodium azide (786 mg, 12.1 mmol), and the mixture was stirred at 80° C. overnight. The reaction mixture was cooled to room temperature, ethyl acetate (20 ml) and hexane (20 ml) were added, and the mixture was washed once with purified water (30 ml), and twice with purified water (15 ml). The organic layer was evaporated under reduced pressure to give 1-azido-1-[(2-chloro-5-(2',3'-dihydrophytyloxy)phenyl)phenylmethane.

$^1$H-NMR (300 MHz): δ0.85-0.95 (15H, m, Me), 0.95-1.85 (24H, br, Me$_2$CH—[C$_3$H$_6$—CHMe]$_3$-CH$_2$CH$_2$—O—Ar), 3.75-4.02 (2H, m, —O—CH$_2$—C$_{19}$H$_{39}$), 5.90-6.10 (1H, m, Ar—CHN$_3$-Ph), 6.79 (1H, d, J=9.0 Hz, C3-H), 7.10-7.50 (7H, m, C4, 6-H, Ph-H).

To the aforementioned 1-azido-1-[(2-chloro-5-(2',3'-dihydrophytyloxy)phenyl)phenylmethane were added THF (20 ml), purified water (2 ml) and triphenylphosphine (813 mg, 3.10 mmol), and the mixture was stirred at 50° C. for 2 hr. The reaction mixture was cooled to room temperature, THF was evaporated, and liquid-separated three times with heptane (30 ml)-50% aqueous acetonitrile solution (15 ml) and the heptane layer was evaporated under reduced pressure. The residue was purified by silica gel column chromatography (hexane:ethyl acetate=100:0→5:1) to give 1-[(2-chloro-5-(2',3'-dihydrophytyloxy)phenyl)]-1-phenylmethanamine as an oil (1.35 g, 2.63 mmol, yield 93% vs. 2,3-dihydrophytyl bromide).

$^1$H-NMR (300 MHz): δ0.85-0.95 (15H, m, Me), 0.95-1.85 (24H, br, Me$_2$CH—[C$_3$H$_6$—CHMe]$_3$-CH$_2$CH$_2$—O—Ar), 3.85-4.00 (2H, br, —O—CH$_2$—C$_{19}$H$_{39}$), 5.43 (1H, s, Ar—CHNH$_2$-Ph), 6.75 (1H, d, J=8.7 Hz, C3-H), 7.10-7.50 (7H, m, C4, 6-H, Ph-H).

Example 4

Synthesis of (4',4'-bisdihydrophytyloxy)benzhydrol

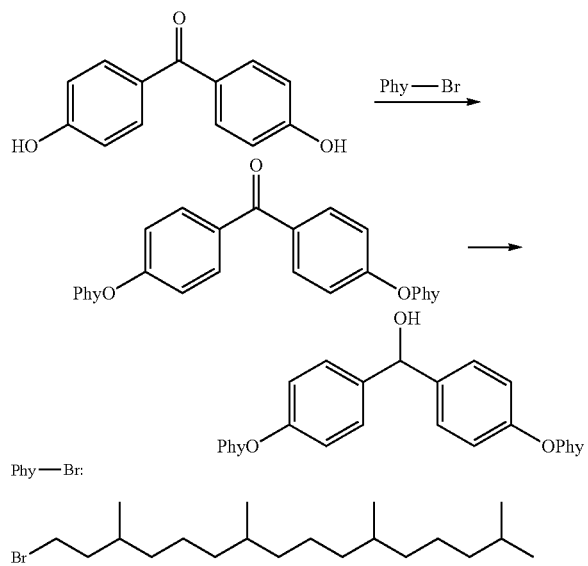

To dihydrophytyl bromide (14.3 g, 39.6 mmol) were added DMF (120 ml), 4,4-bishydroxybenzophenone (4.04 g, 18.9 mmol) and potassium carbonate (7.82 g, 56.6 mmol), and the mixture was stirred at 80° C. for 5 hr. The reaction mixture was cooled to room temperature, ethyl acetate (300 ml) and 1N hydrochloric acid (100 ml) were added and the mixture was stirred to allow layer-separation. The aqueous layer was separated and discarded. The organic layer was washed twice with purified water (100 ml), and the organic layer was evaporated under reduced pressure to give 4,4-bisdihydrophytyloxybenzophenone oil. This was dissolved in chloroform (60 ml) and methanol (10 ml), boron hydrogen sodium (4.49 g, 119 mmol) was added, and the mixture was stirred at 60° C. for 3 hr. To the reaction mixture was added 1M hydrochloric acid (80 ml), and the mixture was concentrated. Ethyl acetate (100 ml) was added, and the mixture was washed successively with 1M hydrochloric acid and water. The organic layer was concentrated to give (4',4'-bisdihydrophytyloxy)benzhydrol oil.

$^1$H-NMR (300 MHz): δ0.86-0.90 (24H, m, Me), 1.10-1.40 (48H, br, Me$_2$CH—[C$_3$H$_6$—CHMe]$_3$-CH$_2$CH$_2$—O—Ar), 2.03 (1H, s, OH), 3.90-3.94 (4H, m, —O—CH$_2$—C$_{19}$H$_{39}$), 5.76 (1H, s, Ar—CHN$_3$-Ph), 6.85 (4H, m, C3-H), 7.20-7.26 (4H, m, C4, 6-H, Ph-H).

Example 5

Synthesis of 3,4,5-tri(2',3'-dihydrophytyloxy)benzyl alcohol

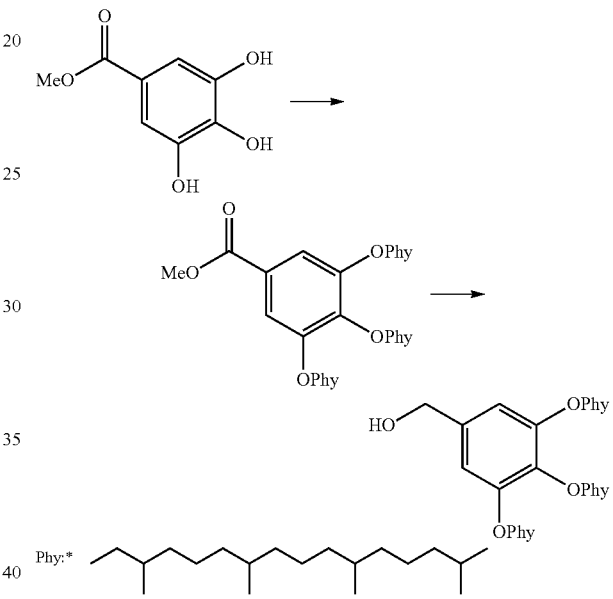

2,3-Dihydrophytyl bromide (40.6 g, 112 mmol), methyl gallate (5.90 g, 32.0 mmol) and potassium carbonate (22.14 g, 160 mmol) were suspended in DMF (400 ml), and the mixture was stirred at 110° C. overnight. The reaction mixture was extracted with hexane (800 ml), washed with 1N hydrochloric acid (400 ml), 5% aqueous sodium hydrogen carbonate solution (400 ml) and 20% brine (400 ml), dried over sodium sulfate and the solvent of the filtrate was evaporated to give methyl 3,4,5-tri(2',3'-dihydrophytyloxy)benzoate (29.3 g, yield 93%).

The aforementioned methyl 3,4,5-tri(2',3'-dihydrophytyloxy)benzoate (29.3 g, 30.0 mmol) was dissolved in THF (400 ml), and diisobutylaluminum hydride (DIBAL)(1.0 mol/l toluene solution, 96 ml, 96 mmol) was added dropwise over 30 min under a nitrogen atmosphere at 0° C. After stirring at room temperature overnight, 0.2N hydrochloric acid (50 ml) was added dropwise at 0° C. to quench the reaction. The solvent was evaporated to about half, and the residue was dissolved in ethyl acetate (600 ml). The mixture was washed three times with 1N hydrochloric acid (300 ml), once with 5% aqueous sodium hydrogen carbonate solution (300 ml), and once with 20% brine (300 ml), and dried over sodium sulfate. The solvent of the filtrate was evaporated to give 3,4,5-tri(2',3'-dihydrophytyloxy)benzyl alcohol (26.8 g, yield 94%).

$^1$H-NMR (300 MHz): δ0.85 (36H, t, J=6.3 Hz, Me), 0.94 (9H, t, J=6.3 Hz, Me), 1.00-2.00 (72H, br, m, Me$_2$CH—[C$_3$H$_6$—CHMe]$_3$-CH$_2$CH$_2$—O—Ar), 3.93-4.07 (6H, m, —CH$_2$—O—Ar), 4.60 (2H, s, —O—CH$_2$—OH), 6.57 (2H, s, C2, 6-H).

Example 6

Synthesis of 2-(3',4',5'-tri(2",3"-dihydrophytyloxy)benzyloxy)-4-methoxybenzylalcohol

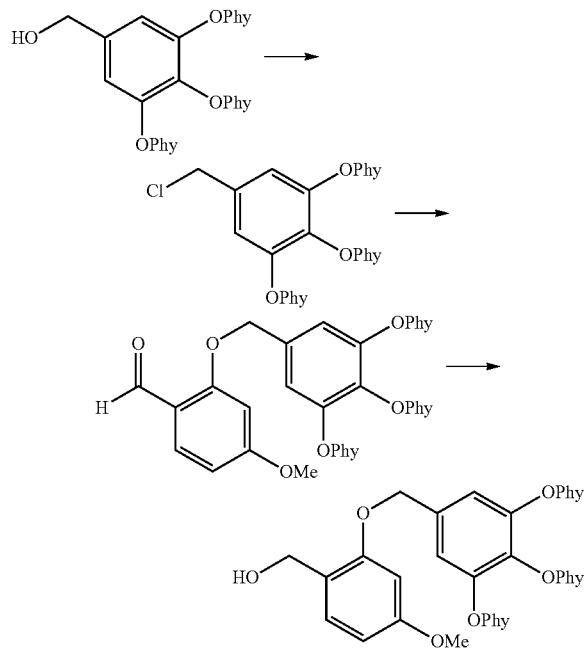

3,4,5-Tri(2',3'-dihydrophytyloxy)benzyl alcohol (5.00 g, 4.87 mmol) was dissolved in chloroform (20 ml), thionyl chloride (1.16 g, 9.74 mmol) was added at 0° C., and the mixture was stirred at room temperature for 1 hr. The solvent was removed to give 3,4,5-tri(2',3'-dihydrophytyloxy)benzylchloride (4.88 g, 4.82 mmol, yield 96%).

$^1$H-NMR (300 MHz): δ0.85 (36H, t, J=6.3 Hz, Me), 0.94 (9H, t, J=6.3 Hz, Me), 1.00-2.00 (72H, br, Me$_2$CH—[C$_3$H$_6$—CHMe]$_3$-CH$_2$CH$_2$—O—), 3.93-4.07 (6H, m, CH$_2$—O—), 4.40 (2H, s, CH$_2$—Cl), 6.57 (2H, s, C2, 6-H).

The aforementioned 3,4,5-tri(2',3'-dihydrophytyloxy)benzylchloride (4.88 g, 4.82 mmol), potassium carbonate (1.68 g, 12.2 mmol, 2.5 eq) and 2-hydroxy-4-methoxybenzaldehyde (0.82 g, 5.36 mmol, 1.1 eq) were suspended in DMF (50 ml), and the mixture was stirred at 80° C. overnight. The reaction mixture was extracted with hexane (500 ml), and the extract was washed three times with 1N hydrochloric acid (250 ml), three times with 5% aqueous sodium hydrogen carbonate solution (250 ml), and once with 20% brine (250 ml). The solvent was removed, and the residue was purified by silica gel column chromatography (ethyl acetate:hexane=1:12) to give 2-(3',4',5'-tri(2",3"-dihydrophytyloxy)benzyloxy)-4-methoxybenzaldehyde (5.53 g, 4.77 mmol, yield 99%).

$^1$H-NMR (300 MHz): δ0.85 (36H, t, J=6.3 Hz, Me), 0.94 (9H, t, J=6.3 Hz, Me), 1.00-2.00 (72H, br, Me$_2$CH—[C$_3$H$_6$—CHMe]$_3$-CH$_2$CH$_2$—O—), 3.85 (3H, s, OMe), 3.93-4.13 (6H, m, CH$_2$—O—), 5.05 (2H, s, CH$_2$—CHO), 6.51 (1H, s, C3-H), 6.56 (1H, d, J=9 Hz, C6-H), 6.63 (2H, s, C2',6'-H), 7.83-7.86 (1H, d, J=9 Hz, C6-H), 10.20 (1H, s, CHO).

2-(3',4',5'-Tri(2",3"-dihydrophytyloxy)benzyloxy)-4-methoxybenzaldehyde (32.0 mmol) was dissolved in THF-methanol (400 ml+20 ml), and sodium borohydride (1.45 g, 38 mmol) was added at 0° C. After stirring at room temperature for 5.5 hr, 0.2N hydrochloric acid (20 ml) was added at 0° C. to quench the reaction. The solvent was evaporated to about half, and the residue was dissolved in ethyl acetate (600 ml), and the mixture was washed twice with 0.1N hydrochloric acid (300 ml), once with 5% aqueous sodium hydrogen carbonate solution (300 ml), and once with 20% brine (300 ml). The solvent was evaporated, and the residue was purified by silica gel column chromatography (chloroform→hexane:ethyl acetate=7:1) to give 2-(3',4',5'-tri(2",3"-dihydrophytyloxy)benzyloxy)-4-methoxybenzylalcohol (30.41 g, 26.8 mmol, yield 97%).

$^1$H-NMR (300 MHz): δ0.85 (45H, t, J=6.3 Hz, Me(Phytol)), 1.00-1.95 (72H, br, C3',4',5'-O—CH$_2$CH$_2$CHMe-[C$_3$H$_6$CHMe]$_3$-Me), 2.18 (1H, br, OH), 3.80 (3H, s, C4-OMe), 3.90-4.08 (6H, m, C3',4',5'-O—CH$_2$—C19H$_{39}$), 4.65 (2H, d, J=3.6 Hz, Ar—CH$_2$—OH), 4.98 (2H, s, Ar—O—CH$_2$—Ar), 6.48 (1H, dd, J=2.1, 8.1 Hz, C5-H), 6.54 (1H, d, J=2.1 Hz, C3-H), 6.61 (2H, s, C2',6'-H), 7.19 (1H, d, J=8.1 Hz, C6-H).

Example 7

Synthesis of 3,4,5-tri(2',3'-dihydrophytyloxy)benzylamine

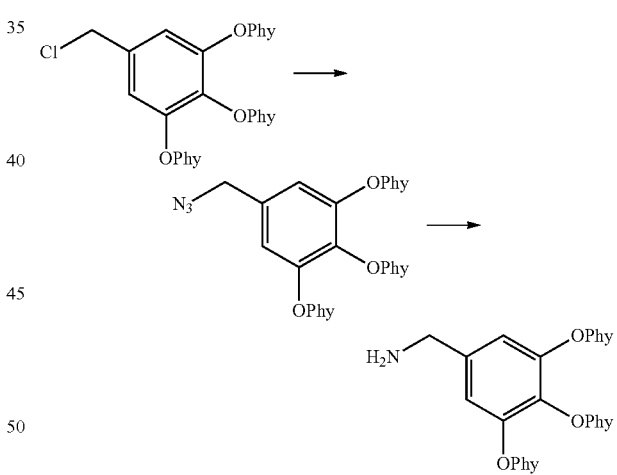

3,4,5-Tri(2',3'-dihydrophytyloxy)benzylchloride (6.46 g, 6.63 mmol) was dissolved in DMF-chloroform (60+20 ml), sodium azide (861 mg, 13.2 mmol) was added and the mixture was stirred at 70° C. for 2 hr. The reaction mixture was cooled to room temperature, ethyl acetate (160 ml) was added, and the mixture was washed twice with water (80 ml) and three times with 20% brine (50 ml), and dried over sodium sulfate. The solvent of the filtrate was evaporated to give 3,4,5-tri(2',3'-dihydrophytyloxy)benzylazide oil, which was directly used for the next step.

The aforementioned 4-(2',3'-dihydrophytyloxy)benzylazide oil was dissolved in THF (80 ml), water (1.19 ml, 66.1 mmol) and triphenylphosphine (1.91 g, 7.28 mmol) were added and the mixture was stirred at 70° C. for 1 hr. After cooling to room temperature, the solvent was evaporated, and the residue was dissolved in heptane (160 ml). The mixture was washed three times with 50% aqueous acetonitrile solution (50 ml) and twice with 20% brine (50 ml), and dried over sodium sulfate. The solvent of the filtrate was evaporated. The obtained residue was purified by silica gel column chromatography (hexane:ethyl acetate=5:1→chloroform:methanol:ammonia water=100:10:1) to give 3,4,5-tri(2',3'-dihydrophytyloxy)benzylamine (5.31 g, 5.32 mmol, yield 80% vs. chloride product).

$^1$H-NMR (300 MHz): δ0.85 (36H, t, J=6.3 Hz, Me), 0.93 (9H, t, J=6.3 Hz, Me), 1.00-2.00 (72H, br, m, Me$_2$CH—[C$_3$H$_6$—CHMe]$_3$-CH$_2$CH$_2$—O—Ar), 3.79 (2H, s, benzyl-H), 3.85-4.10 (6H, m, —CH$_2$—O—Ar), 6.52 (2H, s, C2, 6-H).

Example 8

Synthesis of 3,5-di(2',3'-dihydrophytyloxy)benzyl alcohol

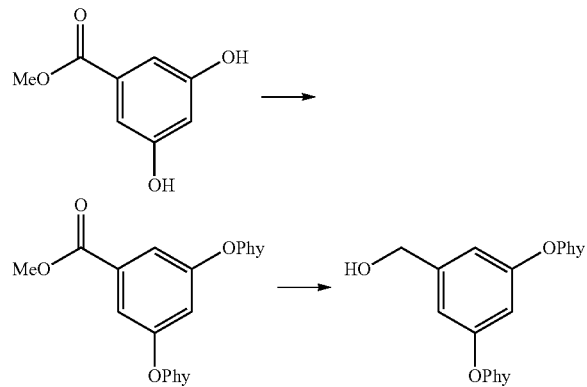

2,3-Dihydrophytyl bromide (895 mg, 2.48 mmol), methyl 3,5-dihydroxybenzoate (204 mg, 1.21 mmol), potassium carbonate (513 mg, 3.71 mmol) were suspended in DMF (10 ml), and the suspension was stirred at 100° C. for 7 hr. The reaction mixture was extracted with ethyl acetate (30 ml), and the extract was washed three times with 1N hydrochloric acid (10 ml) and 20% brine (10 ml), and dried over sodium sulfate. The solvent of the filtrate was evaporated to give methyl 3,4,5-tri(2',3'-dihydrophytyloxy)benzoate (0.78 g, yield 92%).

The aforementioned methyl 3,4,5-di(2',3'-dihydrophytyloxy)benzoate (0.70 g, 1.00 mmol) was dissolved in THF (10 ml), and lithium aluminum hydride (2.0 mol/l THF solution, 1.2 ml, 2.4 mmol) was added dropwise under a nitrogen atmosphere at 0° C. After stirring at room temperature for 5 hr, water was added dropwise at 0° C. to quench the reaction. The solution was dissolved in ethyl acetate (30 ml), and the mixture was washed three times with 1N hydrochloric acid (10 ml), and once with 20% brine (20 ml), and dried over sodium sulfate. The solvent of the filtrate was evaporated. The obtained residue was purified by silica gel column chromatography (hexane alone→hexane:ethyl acetate=5:1) to give 3,4,5-di(2',3'-dihydrophytyloxy)benzyl alcohol (0.61 g, yield 90%).

$^1$H-NMR (300 MHz): δ0.80-0.90 (24H, m, Me), 0.93 (6H, d, J=6.3 Hz, Me), 1.00-1.90 (48H, br, m, Me$_2$CH—[C$_3$H$_6$—CHMe]$_3$-CH$_2$CH$_2$—O—Ar), 3.92-4.02 (4H, m, C$_{19}$H$_{39}$—CH$_2$—O—Ar), 4.62 (2H, s, Ar—CH$_2$—OH), 6.38 (1H, t, J=2.1 Hz, C4-H), 6.50 (2H, d, J=2.0 Hz, C2, 6-H).

Example 9

Synthesis of 4-(2',3'-dihydrophytyloxy)benzyl alcohol

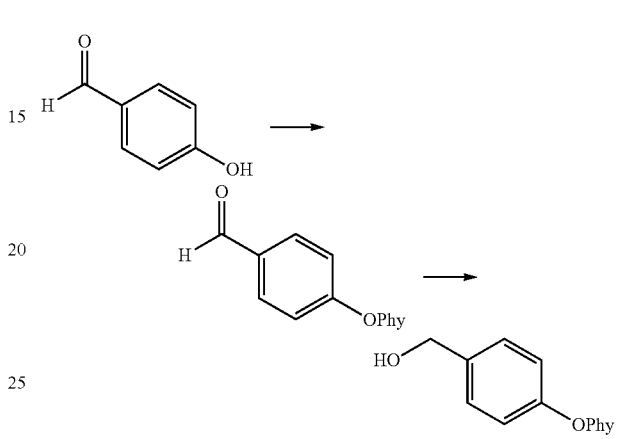

2,3-Dihydrophytyl bromide (600 mg, 1.66 mmol), 4-hydroxybenzaldehyde (223 mg, 1.83 mmol) and potassium carbonate (344 mg, 2.49 mmol) were suspended in DMF (6 ml), and the suspension was stirred at 60° C. for 3 days. The reaction mixture was cooled to room temperature, and extracted with ethyl acetate (30 ml). The extract was washed three times with 1N hydrochloric acid (6 ml), three times with 5% aqueous sodium hydrogen carbonate solution (6 ml), and once with 20% brine (6 ml), and dried over sodium sulfate. The solvent of the filtrate was evaporated. The obtained residue was purified by silica gel column chromatography (hexane:ethyl acetate=15:1→5:1) to give 4-(2',3'-dihydrophytyloxy)benzaldehyde (640 mg, yield 100% vs. 2,3-dihydrophytyl bromide).

$^1$H-NMR (300 MHz): δ0.82-0.89 (12H, m, Me), 0.95 (3H, d, J=6.4 Hz, Me), 1.00-1.95 (24H, m, Me$_2$CH—[C$_3$H$_6$—CHMe]$_3$-CH$_2$CH$_2$—O—Ar), 4.03-4.13 (2H, m, —O—CH$_2$—C$_{19}$H$_{39}$), 4.62 (2H, s, Ar—CH$_2$—OH), 6.99 (2H, m, C3, 5-H), 7.83 (2H, m, C2, 6-H), 9.88 (1H, s, CHO).

The aforementioned 4-(2',3'-dihydrophytyloxy)benzaldehyde (640 mg, 1.66 mmol) was dissolved in THF-methanol mixed solution (7+0.3 ml), sodium borohydride (110 mg, 90%, 2.62 mmol) was added at 0° C., and the mixture was stirred at room temperature for 30 min. The reaction mixture was cooled to 0° C., and the reaction was quenched with 1N hydrochloric acid. Ethyl acetate (30 ml) was added and the mixture was washed three times with 1N hydrochloric acid (5 ml), three times with 5% aqueous sodium hydrogen carbonate solution (5 ml), and once with 20% brine (5 ml), and dried over sodium sulfate. The solvent of the filtrate was evaporated to give 4-(2',3'-dihydrophytyloxy)benzyl alcohol (619 mg, 1.53 mmol, yield 92% vs. 2,3-dihydrophytyl bromide).

$^1$H-NMR (300 MHz): δ0.81-0.90 (12H, m, Me), 0.94 (3H, d, J=6.4 Hz, Me), 1.00-1.90 (24H, m, Me$_2$CH—[C$_3$H$_6$—CHMe]$_3$-CH$_2$CH$_2$—O—Ar), 3.94-4.05 (2H, m, —O—CH$_2$—C$_{19}$H$_{39}$), 6.89 (2H, m, C3, 5-H), 7.28 (2H, m, C2, 6-H).

Example 10

Synthesis of 4-(2',3'-dihydrophytyloxy)benzylamine

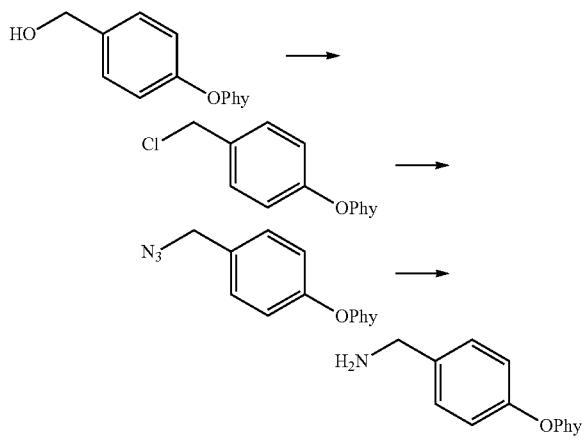

4-(2',3'-Dihydrophytyloxy)benzyl alcohol (619 mg, 1.53 mmol) was dissolved in chloroform (6 ml), thionyl chloride (167 μl, 2.29 mmol) was added and the mixture was stirred for 5 hr. After completion of the reaction, the solvent was evaporated to give 4-(2',3'-dihydrophytyloxy)-benzyl chloride oil, which was directly used for the next step.

The aforementioned 4-(2',3'-dihydrophytyloxy)benzyl chloride (1.53 mmol) was dissolved in DMF-CHCl$_3$ mixed solvent (6+3 ml), sodium azide (298 mg, 4.58 mmol) was added and the mixture was stirred at 70° C. overnight. The reaction mixture was cooled to room temperature, ethyl acetate (20 ml) was added, and the mixture was washed 5 times with water (10 ml) and dried over sodium sulfate. The solvent of the filtrate was evaporated to give 4-(2',3'-dihydrophytyloxy)benzyl azide (632 mg, yield 96% vs. 4-(2',3'-dihydrophytyloxy)benzyl alcohol).

$^1$H-NMR (300 MHz): δ0.81-0.90 (12H, m, Me), 0.94 (3H, d, J=6.4 Hz, Me), 1.00-1.90 (24H, m, Me$_2$CH—[C$_3$H$_6$—C HMe]$_3$-CH$_2$CH$_2$—O—Ar), 3.94-4.04 (2H, m, —O—C H$_2$—C$_{19}$H$_{39}$), 4.26 (2H, s, Ar—CH$_2$—N$_3$), 6.90 (2H, d, J=8.6 Hz, C3, 5-H), 7.23 (2H, d, J=8.6 Hz, C2, 6-H).

The aforementioned 4-(2',3'-dihydrophytyloxy)benzyl azide (632 mg, 1.47 mmol) was dissolved in THF (6 ml), water (265 μl, 14.7 mmol) and triphenylphosphine (424 mg, 1.62 mmol) were added and the mixture was stirred at 70° C. overnight. After cooling to room temperature, the solvent was evaporated, and the residue was dissolved in hexane (10 ml), and the mixture was washed 3 times with 50% aqueous acetonitrile solution (5 ml). The solvent was evaporated. The obtained residue was purified by silica gel column chromatography (hexane:ethyl acetate=5:1→chloroform:methanol: ammonia water=50:5:1) to give 4-(2',3'-dihydrophytyloxy) benzylamine (555 mg, 1.37 mmol, yield 94%).

$^1$H-NMR (300 MHz): δ0.86 (12H, t, J=6.0 Hz, Me), 0.94 (3H, d, J=6.6 Hz, Me), 1.00-1.90 (24H, m, Me$_2$CH—[C$_3$ H$_6$—CHMe]$_3$-CH$_2$CH$_2$—O—Ar), 3.80 (2H, s, Ar—C H$_2$—NH$_2$), 3.92-4.04 (2H, m, —O—CH$_2$—C$_{19}$H$_{39}$), 6.87 (2H, d, J=8.6 Hz, C3, 5-H), 7.21 (2H, d, J=8.6 Hz, C2, 6-H).

Example 11

Synthesis of 2-methoxy-4-(2',3'-dihydrophytyloxy)benzylamine

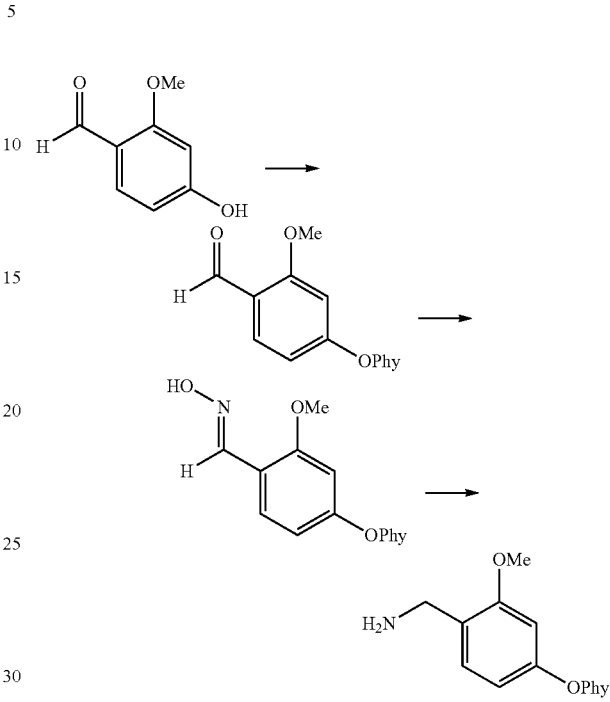

2,3-Dihydrophytyl bromide (2.00 g, 5.53 mmol), 2-methoxy-4-hydroxybenzaldehyde (884 mg, 5.81 mmol) and potassium carbonate (1.15 g, 8.32 mmol) were suspended in DMF (20 ml), and the suspension was stirred at 80° C. overnight. The reaction mixture was cooled to room temperature, and extracted with ethyl acetate (50 ml). The extract was washed three times with 1N hydrochloric acid (20 ml), three times with 5% aqueous sodium hydrogen carbonate solution (20 ml), and once with 20% brine (20 ml), and dried over sodium sulfate. The solvent of the filtrate was evaporated. The obtained residue was purified by silica gel column chromatography (hexane:ethyl acetate=20:1) to give 2-methoxy-4-(2',3'-dihydrophytyloxy)benzaldehyde oil, which was used for the next step.

The aforementioned 2-methoxy-4-(2',3'-dihydrophytyloxy)benzaldehyde, hydroxylamine hydrochloride (1.15 g, 16.5 mmol) were suspended in dichloromethane (25 ml), triethylamine (3.84 ml, 27.7 mmol) was added at 0° C. and the suspension was stirred at room temperature for 3 hr. To the reaction mixture was added chloroform (30 ml) and the mixture was washed three times with 1N hydrochloric acid (15 ml), three times with 5% aqueous sodium hydrogen carbonate solution (15 ml), and once with 20% brine (15 ml), and the solvent was evaporated to give 2-methoxy-4-(2',3'-dihydrophytyloxy)benzaldoxime. After confirmation of the structure by NMR, it was used for the next step.

$^1$H-NMR (300 MHz): δ0.82-0.92 (12H, m, Me), 0.95 (3H, d, J=6.4 Hz, Me), 1.00-1.95 (24H, m, Me$_2$CH—[C$_3$H$_6$—C HMe]$_3$-CH$_2$CH$_2$—O—Ar), 3.83 (3H, s, OMe), 3.97-4.10 (2H, m, —O—CH$_2$—C$_{19}$H$_{39}$), 6.44 (1H, d, J=2.2 Hz, C3-H), 6.49 (1H, dd, J=2.2, 8.6 Hz, C5-H), 7.15 (1H, s, —CHNOH), 7.62 (1H, d, J=8.6 Hz, C6-H), 8.41 (1H, s, —C HNOH).

The aforementioned 2-methoxy-4-(2',3'-dihydrophytyloxy)benzaldoxime was dissolved in methanol-THF mixed solvent (20+10 ml), 10% palladium-carbon (K) (200 mg) was added and the mixture was stirred under a hydrogen atmosphere at room temperature overnight. The solvent of the filtrate was evaporated. The obtained residue was purified by silica gel column chromatography (chloroform: methanol:ammonia water=100:10:1) to give 2-methoxy-4-(2',3'-dihydrophytyloxy)benzylamine (1.87 g, 4.31 mmol, yield 78% vs. 2,3-dihydrophytyl bromide).

$^1$H-NMR (300 MHz): δ0.80-0.90 (12H, m, Me), 0.94 (3H, d, J=6.4 Hz, Me), 1.00-1.90 (24H, m, Me$_2$C$\underline{H}$—[C$_3$$\underline{H_6}$—CHMe]$_3$-C$\underline{H_2}$CH$_2$—O—Ar), 3.74 (2H, s, Ar—C$\underline{H_2}$—NH$_2$), 3.82 (3H, s, OMe), 3.90-4.05 (2H, m, —O—C$\underline{H_2}$—C$_{19}$H$_{39}$), 6.42 (1H, dd, J=2.3, 8.1 Hz, C5-$\underline{H}$), 6.46 (1H, d, J=2.1 Hz, C3-$\underline{H}$), 7.09 (1H, d, J=8.1 Hz, C6-$\underline{H}$).

Example 12

Synthesis of 4-(2',3'-dihydrophytyloxy)-2-methyl-benzyl alcohol

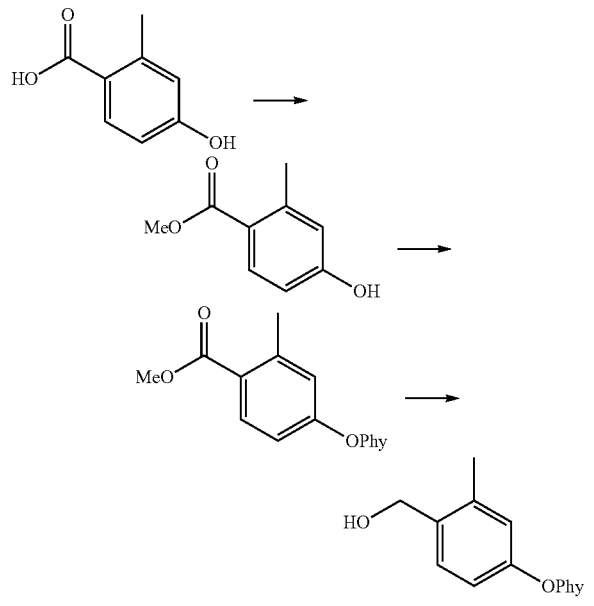

To methanol (10 ml) was added dropwise thionyl chloride (1.92 ml, 26.3 mmol) at 0° C., 4-hydroxy-2-methylbenzoic acid (2.00 g, 13.1 mmol) was added, and the mixture was stirred at 60° C. overnight. After completion of the reaction, the solvent was evaporated, and the residue was dissolved in ethyl acetate (20 ml). The mixture was washed twice with 5% aqueous sodium hydrogen carbonate solution (10 ml), once with 1N hydrochloric acid (10 ml), and once with water (10 ml), and the solvent was evaporated to give methyl 4-hydroxy-2-methylbenzoate (2.24 g, yield 100%).

$^1$H-NMR (300 MHz): δ2.57 (3H, s, C2-Me), 3.86 (3H, s, —COOMe), 5.68 (1H, s, br, —OH), 6.66-6.72 (2H, m, C3, 5-$\underline{H}$), 7.89 (1H, dd, J=2.4, 6.9 Hz, C6-$\underline{H}$).

The aforementioned methyl 4-hydroxy-2-methylbenzoate (269 mg, 1.62 mmol), 2,3-dihydrophytyl bromide (389 mg, 1.08 mmol) and potassium carbonate (297 mg, 2.15 mmol) were suspended in DMF (5 ml), and the suspension was stirred at 90° C. for 5 hr. The reaction mixture was cooled to room temperature, extracted with hexane-ethyl acetate (10+10 ml), and washed once with 1N hydrochloric acid (15 ml) and twice with water (10 ml). The solvent was evaporated to give methyl 4-(2',3'-dihydrophytyloxy)-2-methyl-benzoate. After confirmation of the structure by NMR, it was used for the next step.

$^1$H-NMR (300 MHz): δ0.85 (12H, t, J=6.6 Hz, Me), 0.94 (3H, d, J=6.6 Hz, Me), 1.00-1.90 (24H, m, Me$_2$C$\underline{H}$—[C$_3$$\underline{H_6}$—CHMe]$_3$-C$\underline{H_2}$CH$_2$—O—Ar), 2.59 (3H, s, C2-Me), 3.85 (3H, s, —COOMe), 4.02 (2H, dt, J=3.0, 6.7 Hz, O—C$\underline{H_2}$—C$_{19}$H$_{39}$), 6.65-6.76 (2H, m, C3, 5-$\underline{H}$), 7.85-7.96 (1H, m, C6-$\underline{H}$).

The aforementioned methyl 4-(2',3'-dihydrophytyloxy)-2-methylbenzoate (1.08 mmol) was dissolved in THF (6 ml), DIBAL (1.0M, 4.9 ml, 4.9 mmol) was added, and the suspension was stirred at room temperature for 100 min. The reaction mixture was cooled to 0° C., and the reaction was quenched with 1N hydrochloric acid (15 ml). Hexane (10 ml) and ethyl acetate (10 ml) were added to allow liquid-separation, and the mixture was washed once with 0.5N hydrochloric acid (10 ml) and once with water (10 ml), and the solvent was evaporated to give 4-(2',3'-dihydrophytyloxy)-2-methylbenzyl alcohol.

$^1$H-NMR (300 MHz): δ0.86 (12H, t, J=6.3 Hz, Me), 0.94 (3H, d, J=6.4 Hz, Me), 1.00-1.90 (24H, m, Me$_2$C$\underline{H}$—[C$_3$$\underline{H_6}$—CHMe]$_3$-C$\underline{H_2}$CH$_2$—O—Ar), 2.36 (3H, s, C2-Me), 3.98 (2H, dt, J=3.0, 6.7 Hz, O—C$\underline{H_2}$—C$_{19}$H$_{39}$), 4.63 (2H, d, J=4.7 Hz, Ar—C$\underline{H_2}$—OH), 6.60-6.77 (2H, m, C3, 5-$\underline{H}$), 7.15-7.25 (1H, m, C6-$\underline{H}$).

Example 13

Synthesis of 4-(2',3'-dihydrophytyloxy)-2-methyl-benzylamine

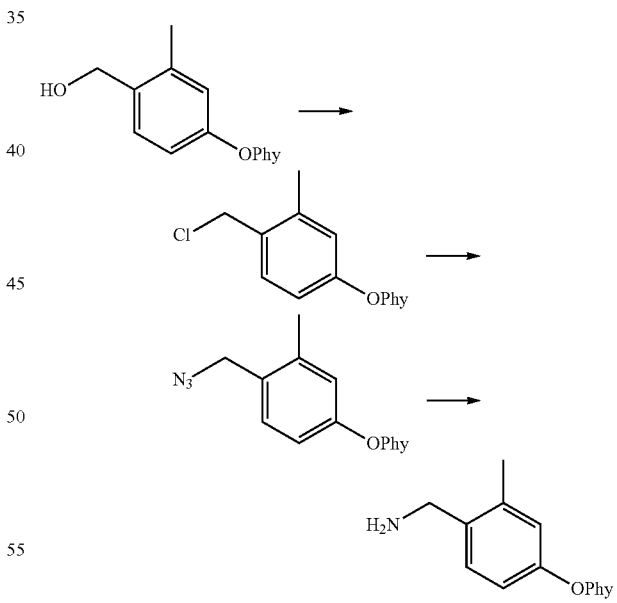

4-(2',3'-Dihydrophytyloxy)-2-methyl-benzyl alcohol (1.08 mmol) was dissolved in chloroform (8 ml), thionyl chloride (393 μl, 5.38 mmol) was added and the mixture was stirred at 50° C. for 4.5 hr. After completion of the reaction, the solvent was evaporated to give 4-(2',3'-dihydrophytyloxy)-2-methylbenzyl chloride. After confirmation of the structure by NMR, it was used for the next step.

$^1$H-NMR (300 MHz): δ0.86 (12H, t, J=6.3 Hz, Me), 0.93 (3H, d, J=6.3 Hz, Me), 1.00-1.90 (24H, m, Me$_2$C$\underline{H}$—[C$_3$ H₆—CHMe]₃-CH₂CH₂—O—Ar), 2.40 (3H, s, C2-Me), 3.97 (2H, dt, J=2.7, 6.7 Hz, O—CH₂—C₁₉H₃₉), 4.59 (2H, s, Ar—CH₂—Cl), 6.69 (1H, dd, J=2.4, 8.3 Hz, C5-H), 6.74 (1H, d, J=2.3 Hz, C3-H), 7.21 (1H, d, J=8.3 Hz, C6-H).

The aforementioned 4-(2',3'-dihydrophytyloxy)-2-methylbenzyl chloride (1.08 mmol) was dissolved in DMF (6 ml), sodium azide (350 mg, 5.38 mmol) was added and the mixture was stirred at 70° C. overnight. The reaction mixture was cooled to room temperature, hexane (10 ml) and ethyl acetate (5 ml) were added, and the mixture was washed 3 times with water (10 ml). The solvent of the filtrate was evaporated to give 4-(2',3'-dihydrophytyloxy)-2-methylbenzyl azide. After confirmation of the structure by NMR, it was used for the next step.

¹H-NMR (300 MHz): δ0.86 (12H, t, J=6.3 Hz, Me), 0.94 (3H, d, J=6.3 Hz, Me), 1.00-1.90 (24H, m, Me₂CH—[C₃H₆—CHMe]₃-CH₂CH₂—O—Ar), 2.34 (3H, s, C2-Me), 3.98 (2H, dt, J=3.0, 6.6 Hz, O—CH₂—C₁₉H₃₉), 4.28 (2H, s, Ar—CH₂—N₃), 6.71 (1H, dd, J=2.6, 8.2 Hz, C5-H), 6.77 (1H, d, J=2.3 Hz, C3-H), 7.15 (1H, d, J=8.3 Hz, C6-H).

The aforementioned 4-(2',3'-dihydrophytyloxy)-2-methylbenzyl azide (1.08 mmol) was dissolved in THF (10 ml), water (2 ml) and triphenylphosphine (565 mg, 2.15 mmol) were added and the mixture was stirred at 60° C. for 3 hr. After cooling to room temperature, the solvent was evaporated, and the residue was dissolved in heptane (10 ml), and washed 3 times with 50% aqueous acetonitrile solution (10 ml). The solvent was evaporated and the obtained residue was purified by silica gel column chromatography (hexane:ethyl acetate=5:1→chloroform:methanol:ammonia water=50:5:1) to give 4-(2',3'-dihydrophytyloxy)-2-methylbenzylamine (281 mg, 0.67 mmol, yield 62% vs. 2,3-dihydrophytyl bromide).

¹H-NMR (300 MHz): δ0.86 (12H, t, J=6.3 Hz, Me), 0.93 (3H, d, J=6.6 Hz, Me), 1.00-1.90 (24H, m, Me₂CH—[C₃H₆—CHMe]₃-CH₂CH₂—O—Ar), 2.32 (3H, s, C2-Me), 3.79 (2H, s, Ar—CH₂—NH₂), 3.97 (2H, dt, J=3.0, 6.7 Hz, O—CH₂—C₁₉H₃₉), 6.71 (1H, dd, J=2.6, 8.2 Hz, C5-H), 6.68-6.75 (2H, br, C3, 5-H), 7.17 (H, d, J=8.7 Hz, C6-H).

Example 14

Synthesis of 2,2,4,8,10,10-hexamethyl-5-dodecanoic acid (4-hydroxymethyl)phenylamide

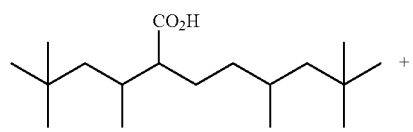

+

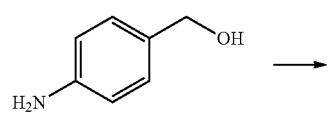

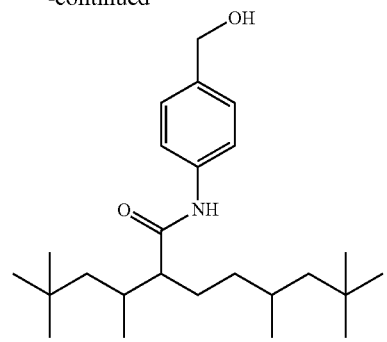

2,2,4,8,10,10-Hexamethyl-5-dodecanoic acid (2.81 g, 9.88 mmol), 4-aminobenzyl alcohol (1.00 g, 8.12 mmol) and 3,4-dihydro-3-hydroxy-4-oxo-1,2,3-benzotriazine (HOOBt) (133 mg, 0.812 mmol) were suspended in chloroform (10 ml), EDC HCl (2.05 g, 10.7 mmol) was added at 0° C., and the suspension was stirred at room temperature overnight. The solvent was removed, and the residue was purified by silica gel column chromatography (hexane:ethyl acetate=2:1) to give 2,2,4,8,10,10-hexamethyl-5-dodecanoic acid (4-hydroxymethyl)phenylamide (2.69 g, 6.67 mmol, yield 82%).

¹H-NMR (300 MHz): δ0.92-0.99 (m, 24H), 1.01-1.09 (m, 6H), 1.19-1.23 (m, 4H), 4.58 (s, 2H), 7.21 (d, 2H, J=6 Hz), 7.43 (d, 2H, J=9 Hz), 7.53-7.66 (b, 1H).

Example 15

Synthesis of 4-(3',7',11'-trimethyldodecyloxy)benzyl alcohol

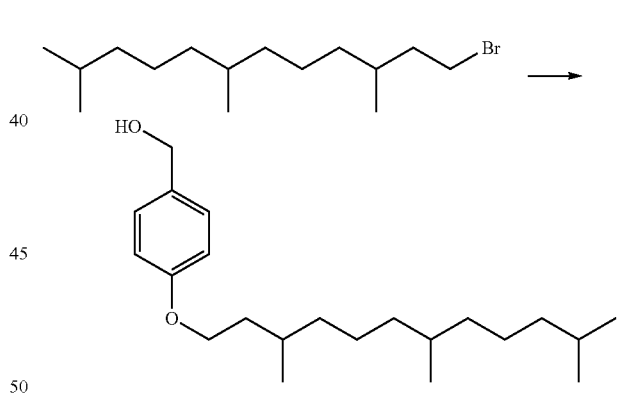

1-Bromo-3,7,11-trimethyldodecane (1.00 g, 3.43 mmol) obtained in Reference Example 4 was dissolved in DMF (5 ml), 4-hydroxybenzyl alcohol (0.85 g, 6.85 mmol) and potassium carbonate (1.42 g, 10.3 mmol) were added and the mixture was stirred at 120° C. overnight. The reaction mixture was cooled to room temperature, extracted with chloroform (50 ml), and the extract was washed three times with 1N hydrochloric acid (30 ml), once with 5% aqueous sodium hydrogen carbonate solution (30 ml), and once with purified water (30 ml). The solvent of the organic layer was evaporated to give 4-(3',7',11'-trimethyldodecyloxy)benzyl alcohol (1.09 g, 3.26 mmol, yield 95% vs. 1-bromo-3,7,11-trimethyldodecane).

¹H-NMR (300 MHz): δ0.81-0.89 (m, 12H), 1.08-1.37 (m, 12H), 1.48-1.83 (m, 5H), 3.96-4.02 (m, 2H), 4.62 (s, 2H), 6.89 (d, 2H, J=9 Hz), 7.29 (d, 2H, J=9 Hz).

Example 16

Synthesis of 2-(3',7',11'-trimethyldodecyloxy)-9-phenylfluoren-9-ol

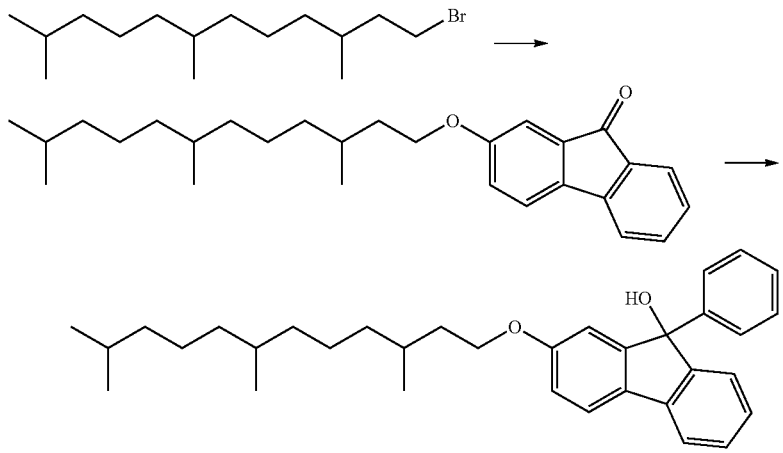

1-Bromo-3,7,11-trimethyldodecane (780 mg, 2.68 mmol) obtained in Reference Example 4 was dissolved in DMF (5 ml), 2-hydroxy-9-fluorenone (1.05 g, 5.35 mmol) and potassium carbonate (1.06 g, 7.67 mmol) were added and the mixture was stirred at 100° C. for 5 hr. The reaction mixture was cooled to room temperature, extracted with heptane (30 ml) and washed three times with 1N hydrochloric acid (15 ml), once with 5% aqueous sodium hydrogen carbonate solution (15 ml), and 3 times with methanol (15 ml). The solvent of the organic layer was evaporated to give 2-(3',7',11'-trimethyldodecyloxy)-9-fluorenone (650 mg, 1.60 mmol, yield 60% vs. 1-bromo-3,7,11-trimethyldodecane).

$^1$H-NMR (300 MHz): δ0.84-0.96 (m, 12H), 1.08-1.30 (m, 12H), 1.50-1.70 (m, 5H), 4.04-4.07 (m, 2H), 6.98 (d, H, J=9 Hz), 7.17-7.22 (m, 1H), 7.28-7.30 (m, 1H), 7.38-7.44 (m, 3H), 7.60 (d, 1H, J=9 Hz).

Under a nitrogen atmosphere, magnesium (280 mg, 11.5 mmol) was suspended in dehydrated THF (2 ml), iodine (45 mg, 0.18 mmol) was added, bromobenzene (390 μl, 3.70 mmol) was slowly added dropwise, and the suspension was stirred at 40° C. for 4 hr. To the reaction mixture was added the aforementioned 2-(3',7',11'-trimethyldodecyloxy)-9-fluorenone (300 mg, 0.74 mmol), and the mixture was stirred at 50° C. overnight. The reaction mixture was cooled to room temperature, and the reaction was quenched with 1N hydrochloric acid (30 ml). The mixture was extracted with chloroform (40 ml), and the extract was washed three times with 1N hydrochloric acid (20 ml), three times with 5% aqueous sodium hydrogen carbonate solution (20 ml), and once with 20% brine (20 ml). The solvent of the organic layer was evaporated, and the obtained residue was purified and separated by silica gel column chromatography (hexane: ethyl acetate=10:1) to give 2-(3',7',11'-trimethyldodecyloxy)-9-phenylfluoren-9-ol (181 mg, 0.37 mmol, yield 51%).

$^1$H-NMR (300 MHz): δ0.86-0.92 (m, 12H), 1.04-1.25 (m, 12H), 1.50-1.59 (m, 5H), 2.49 (s, 1H), 3.92-3.96 (m, 2H), 6.80-6.91 (m, 3H), 7.16-40 (m, 7H), 7.52-7.63 (m, 2H).

Example 17

Synthesis of 2-(3',7',11'-trimethyldodecyloxy)-9-bromo-9-phenylfluorene

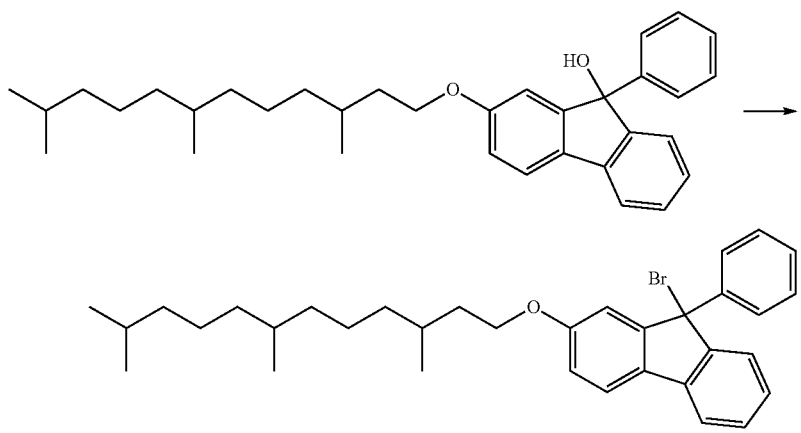

The aforementioned 2-(3',7',11'-trimethyldodecyloxy)-9-phenylfluoren-9-ol (181 mg, 0.37 mmol) was dissolved in chloroform (2 ml), acetyl bromide (55 μl, 0.74 mmol) was added dropwise and the mixture was stirred for 6 hr. After completion of the reaction, the solvent was evaporated, and the residue was dissolved in heptane, and washed three times with acetonitrile. The solvent of the heptane layer was evaporated to give 2-(3',7',11'-trimethyldodecyloxy)-9-bromo-9-phenylfluorene (126 mg, 0.23 mmol, yield 62%).

$^1$H-NMR (300 MHz): δ0.83-0.94 (m, 12H), 1.09-1.36 (m, 12H), 1.50-1.59 (m, 5H), 3.96-4.01 (m, 2H), 6.90-6.93 (m, 1H), 7.03 (s, 1H), 7.21-7.35 (m, 5H), 7.44-7.48 (m, 2H), 7.54-7.58 (m, 3H).

Example 18

Synthesis of di(2-hydroxymethyl-5-methoxyphenoxy) Product of GI-1000 (manufactured by Nippon Soda Co., Ltd.) (GI-1000(2-hydroxymethyl-5-methoxyphenoxy))

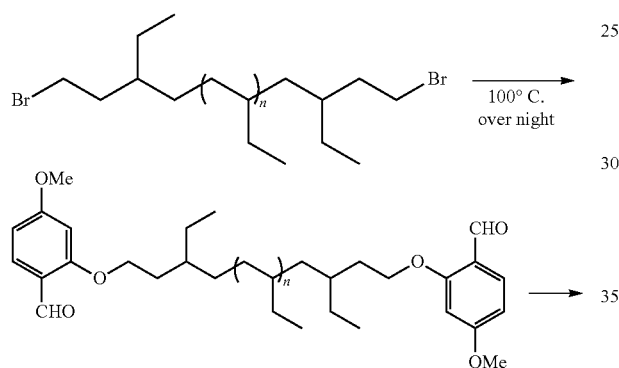

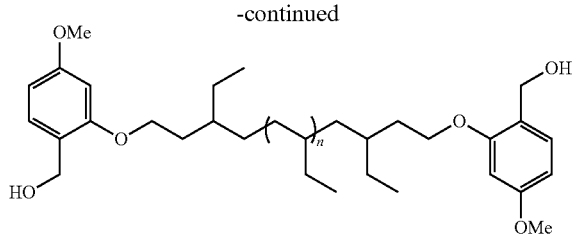

GI-1000(Br)(1.70 g) obtained in Reference Example 5 was dissolved in DMF (20 ml), 2-hydroxy-4-methoxybenzaldehyde (1.00 g, 6.57 mmol) and potassium carbonate (1.17 g, 8.47 mmol) were added and the mixture was stirred at 120° C. overnight. The reaction mixture was cooled to room temperature, extracted with ethyl acetate/hexane (1:1, 20 ml), and the extract was washed three times with 1N hydrochloric acid (10 ml), once with 5% aqueous sodium hydrogen carbonate solution (30 ml), and once with purified water (30 ml). The solvent of the organic layer was evaporated, the residue was decanted with methanol, and concentrated to give GI-1000 (2-formyl-5-methoxyphenoxy) (1.60 g).

$^1$H-NMR (300 MHz): δ0.98-1.49 (m), 1.82-1.87 (m, 4H), 3.87 (s, 6H), 4.01-4.06 (m, 4H), 6.43 (s, 2H), 6.53 (d, 2H, J=7.8 Hz), 7.82 (d, 2H, J=7.8 Hz), 10.34 (s, 2H)

The aforementioned GI-1000 (2-formyl-5-methoxyphenoxy) (1.60 g) was dissolved in chloroform (16 ml)/methanol (1.6 ml) mixed solution, sodium borohydride (0.38 g, 9.99 mmol) was added and the mixture was stirred at 60° C. for 2.5 hr. The reaction mixture was cooled to room temperature, and washed three times with 1N hydrochloric acid (16 ml), three times with 5% aqueous sodium hydrogen carbonate solution (16 ml) and once with 20% brine (16 ml). The solvent of the organic layer was evaporated, the residue was decanted with methanol, and concentrated to give GI-1000 (2-hydroxymethyl-5-methoxyphenoxy) (1.84 g).

$^1$H-NMR (300 MHz): δ1.06-1.43 (m), 1.71-1.83 (m, 4H), 3.80 (s, 6H), 3.98-4.01 (m, 4H), 4.61 (s, 2H), 6.42-6.45 (m, 4H), 7.16 (d, 2H, J=7.9 Hz).

Example 19

Synthesis of di(3-hydroxymethylphenoxy) product of GI-1000 (Manufactured by Nippon Soda Co., Ltd.) (Bzl(3-O-GI-1000)-OH)

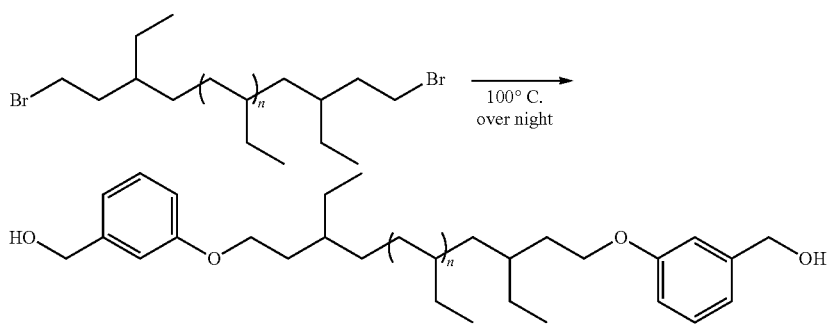

GI-1000(Br) (563 mg) obtained in Reference Example 5 was dissolved in DMF (5 ml), 3-hydroxybenzyl alcohol (280 mg, 2.26 mmol) and potassium carbonate (389 mg, 2.81 mmol) were added and the mixture was stirred at 100° C. overnight. The reaction mixture was cooled to room temperature, extracted with ethyl acetate/hexane (1:1, 25 ml), and the extract was washed three times with 1N hydrochloric acid (10 ml), once with 5% aqueous sodium hydrogen carbonate solution (10 ml), and once with methanol (10 ml). The solvent of the organic layer was evaporated to give Bzl(3-O-GI-1000)-OH (580 mg).

$^1$H-NMR (300 MHz): δ0.85-1.28 (m), 3.94-3.98 (m, 4H), 4.67 (s, 4H), 6.83 (d, 2H, J=9 Hz), 6.91-6.93 (m, 4H), 7.23-7.26 (m, 2H).

Example 20

Synthesis of di(3-hydroxymethylphenoxy) Product of GI-2000 (Manufactured by Nippon Soda Co., Ltd.) (Bzl(3-O-GI-2000)-OH)

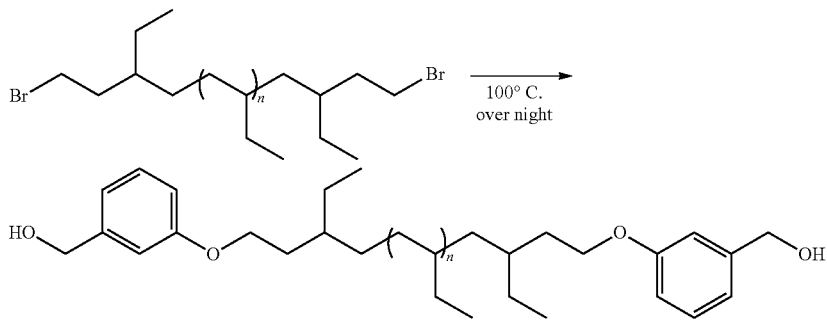

GI-2000(Br) (503 mg) obtained in Reference Example 6 was dissolved in DMF (5 ml), 3-hydroxybenzyl alcohol (125 mg, 1.00 mmol) and potassium carbonate (174 mg, 1.26 mmol) were added and the mixture was stirred at 100° C. overnight. The reaction mixture was cooled to room temperature, extracted with ethyl acetate/hexane (1:1, 25 ml), and the extract was washed three times with 1N hydrochloric acid (10 ml), once with 5% aqueous sodium hydrogen carbonate solution (10 ml), and once with methanol (10 ml). The solvent of the organic layer was evaporated to give Bzl(3-O-GI-2000)-OH (512 mg).

$^1$H-NMR (300 MHz): δ0.88-1.31 (m), 3.94-4.01 (m, 4H), 4.67 (s, 4H), 6.83 (d, 2H, J=9 Hz), 6.91-6.93 (m, 4H), 7.23-7.28 (m, 2H).

Example 21

Synthesis of TERGITOL-Adduct of 3-hydroxymethylphenol

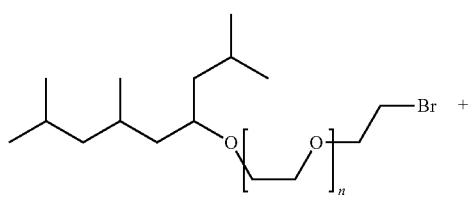

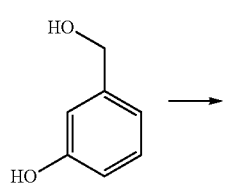

-continued

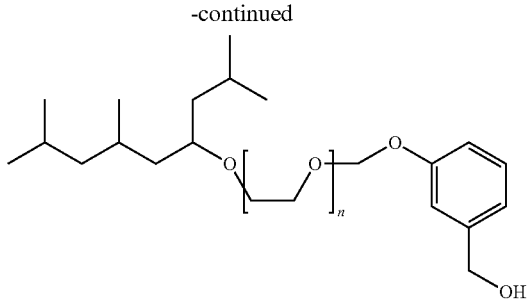

The Br product (5.21 g) of TERGITOL (registered trademark) TMN-6 obtained in Reference Example 7, potassium carbonate (2.93 g, 21.2 mmol, 2.5 eq) and 3-hydroxy-benzyl alcohol (1.16 g, 9.32 mmol, 1.1 eq) were suspended in DMF (50 ml), and the suspension was stirred at 80° C. overnight. The reaction mixture was extracted with ethyl acetate (500 ml) and the extract was washed three times with 0.5N hydrochloric acid (250 ml), three times with 5% aqueous sodium hydrogen carbonate solution (250 ml), and once with 20% brine (250 ml). The solvent was removed, and the residue was purified by silica gel column chromatography (ethyl acetate→ethyl acetate:methanol=1:1). The solvent was removed, and the residue was dissolved in ethyl acetate (100 ml) and silica gel was removed by filtration to give Bzl(3-TERGITOL)-OH (3.93 g).

$^1$H-NMR (300 MHz): δ0.80-0.90 (m, 15H, CH$_3$), 1.00-1.60 (m, 11H, CH, CH$_2$), 3.50-3.68 (m, (OCH$_2$CH$_2$)$_n$), 4.55-4.59. (s, 2H, CH$_2$—OH), 6.70-6.79 (m, 2H, C2, C4-H), 6.87 (s, 1H, C6-H), 7.08-7.13 (t, 1H, C5-H).

$^{13}$C-NMR: δ20.42-27.39 (CH$_3$, CH), 42.78-47.67 (CH$_2$), 68.04 (OCH$_2$, CH$_2$OH), 70.79-71.55 (OCH$_2$CH$_2$O), 71.07 (CH$_2$O-BzlOH), 114.21 (C4), 114.62 (C2), 118.19 (C6), 129.47 (C5), 143.19 (C1), 157.29 (C3).

Example 22

Synthesis of (4-hydroxymethyl)carboxamide Product of SAFONAMINE B-30 (Manufactured by MITSUI FINE CHEMICAL Inc. or Huntsman Corporation) (Number Average Molecular Weight: about 325; n=about 2)

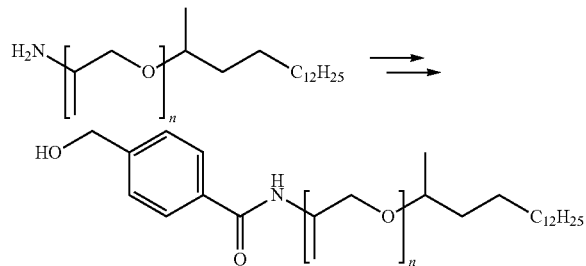

SAFONAMINE B-30 (2.0 g) was dissolved in chloroform (20 ml), and wash three times with water (10 ml). The organic layer was dried over sodium sulfate and concentrated to dryness. The residue was dissolved in chloroform (20 ml), monomethyl terephthalate (1.0 g) was added, EDC HCl (1.15 g) and HOBt (72 mg) were added and the mixture was reacted at room temperature for 3 hr, washed with aqueous sodium hydrogen carbonate solution and saturated brine, and concentrated to give an oil. To the oil were added tetrahydrofuran and 1M DIBAL toluene solution (4.2 equivalents) and the mixture was reacted under ice-cooling. 1M Hydrochloric acid was added to quench the reaction, chloroform was added, and the mixture was successively washed with 1M hydrochloric acid, aqueous sodium hydrogen carbonate solution, and saturated brine to give a benzyl alcohol product (1.30 g).

Using the compounds of Examples 1, 3, 5, 19 and 20 as protecting reagents, peptide synthesis was performed.

Example 23

Synthesis of Fmoc-Ser(tBu)-OBzl(2,4-OPhy) by Condensation of 2,4-(2',3'-dihydrophytyloxy)benzyl alcohol and Fmoc-Ser (tBu)-OH Fmoc-Ser(tBu)-OH (3.28 g, 8.56 mmol) was dissolved in isopropyl acetate (30 ml), EDC HCl (1.80 g, 9.39 mmol) was added at 0° C., and the mixture was stirred at room temperature for 30 min. A solution of 2,4-(2',3'-dihydrophytyloxy)benzyl alcohol (3.00 g, 4.28 mmol) obtained in Example 1 in isopropyl acetate (15 ml) and N,N-dimethyl-4-aminopyridine (DMAP) (105 mg, 0.86 mmol) were added and the mixture was stirred overnight. The reaction mixture was washed three times with 0.1N hydrochloric acid (15 ml), three times with 5% aqueous sodium hydrogen carbonate solution (15 ml), and once with 20% brine (15 ml) to allow conversion to a condensation product (Fmoc-Ser(tBu)-OBzl(2,4-OPhy)) in the reaction system, which was used in the subsequent reaction.

Example 24

Synthesis of H-Ser(tBu)-OBzl(2,4-OPhy) by Removal of Fmoc from Fmoc-Ser(tBu)-OBzl(2,4-OPhy)

To a solution (45 ml) of Fmoc-Ser(tBu)-OBzl(2,4-OPhy) (4.28 mmol) in isopropyl acetate was added 4-aminomethylpiperidine (1.47 g, 12.9 mmol) at 0° C., and the mixture was stirred at room temperature for 4 hr. The reaction mixture was aerated with carbon dioxide, the resulting carbonate was removed by filtration, and the filtrate was washed three times with 1M aqueous sodium phosphate solution (30 ml) adjusted to pH=5.5, once with 10% aqueous sodium carbonate solution (30 ml), and once with 20% brine (30 ml) to allow conversion to a de-Fmoc product (H-Ser(tBu)-OBzl(2,4-OPhy)) in the reaction system, which was used for the subsequent reaction.

Example 25

Synthesis of Fmoc-Lys(Boc)-Ser(tBu)-OBzl(2,4-OPhy) by Condensation of H-Ser(tBu)-OBzl(2,4-OPhy) and Fmoc-Lys(Boc)-OH In a solution of H-Ser(tBu)-OBzl(2,4-OPhy) (4.18 mmol) in isopropyl acetate (55 ml) were dissolved HOBt (57 mg, 0.42 mmol) and Fmoc-Lys(Boc)-OH (2.16 g, 4.61 mmol), EDC HCl (970 mg, 5.06 mmol) was added at 0° C., and the mixture was stirred at room temperature overnight. The reaction mixture was washed three times with 0.1N hydrochloric acid (30 ml), three times with 5% aqueous sodium hydrogen carbonate solution (30 ml), and once with 20% brine (30 ml) to allow conversion to Fmoc-Lys(Boc)-Ser(tBu)-OBzl(2,4-OPhy) in the reaction system, which was used in the subsequent reaction.

Example 26

Synthesis of H-Lys(Boc)-Ser(tBu)-OBzl(2,4-OPhy) by Removal of Fmoc from Fmoc-Lys(Boc)-Ser(tBu)-OBzl(2,4-OPhy)

To a solution (55 ml) of Fmoc-Lys(Boc)-Ser(tBu)-OBzl(2,4-OPhy) (4.18 mmol) in isopropyl acetate was added 4-aminomethylpiperidine (1.91 g, 16.7 mmol) at 0° C., and the mixture was stirred at room temperature for 4 hr. The reaction mixture was aerated with carbon dioxide, the resulting carbonate was removed by filtration, and the filtrate was washed three times with 1M aqueous sodium phosphate solution (30 ml) adjusted to pH=5.5, once with 10% aqueous sodium carbonate solution (30 ml), and once with 20% brine (30 ml) to allow conversion to H-Lys(Boc)-Ser(tBu)-OBzl(2,4-OPhy) in the reaction system, which was used for the subsequent reaction.

Example 27

Synthesis of Fmoc-Glu(OtBu)-Lys(Boc)-Ser(tBu)-OBzl(2,4-OPhy) by condensation of H-Lys(Boc)-Ser(tBu)-OBzl (2,4-OPhy) and Fmoc-Glu(OtBu)-OH In a solution (105 ml) of H-Lys(Boc)-Ser(tBu)-OBzl(2,4-OPhy) (4.18 mmol) in isopropyl acetate were dissolved HOBt (57 mg, 0.42 mmol) and Fmoc-Glu(OtBu)-OH (2.32 g, 5.23 mmol), EDC HCl (1.09 g, 5.69 mmol) was added at 0° C., and the mixture was stirred at room temperature overnight. The reaction mixture was washed three times with 0.1N hydrochloric acid (30 ml), three times with 5% aqueous sodium hydrogen carbonate solution (30 ml), and once with 20% brine (30 ml) to allow conversion to Fmoc-Glu(OtBu)-Lys(Boc)-Ser(tBu)-OBzl(2,4-OPhy) in the reaction system, which was used in the subsequent reaction.

Example 28

Synthesis of H-Glu(OtBu)-Lys(Boc)-Ser(tBu)-OBzl (2,4-OPhy) by removal of Fmoc from Fmoc-Glu (OtBu)-Lys (Boc)-Ser (tBu)-OBzl (2,4-OPhy)

To a solution (50 ml) of Fmoc-Glu(OtBu)-Lys(Boc)-Ser(tBu)-OBzl(2,4-OPhy) in isopropyl acetate was added 4-aminomethylpiperidine (1.43 g, 12.5 mmol) at 0° C., and the mixture was stirred at room temperature for 4 hr. The reaction mixture was aerated with carbon dioxide, the resulting carbonate was removed by filtration, and the filtrate was washed three times with 1M aqueous sodium phosphate solution (30 ml) adjusted to pH=6.86, once with 10% aqueous sodium carbonate solution (30 ml), and once with 20% brine (30 ml) to allow conversion to H-Glu(OtBu)-Lys(Boc)-Ser(tBu)-OBzl(2,4-OPhy) in the reaction system, which was used for the subsequent reaction.

Example 29

Synthesis of Fmoc-Ala-Glu(OtBu)-Lys(Boc)-Ser(tBu)-OBzl(2,4-OPhy) by condensation of H-Glu(OtBu)-Lys(Boc)-Ser(tBu)-OBzl (2,4-OPhy) and Fmoc-Ala-OH In a solution (105 ml) of H-Glu(OtBu)-Lys(Boc)-Ser(tBu)-OBzl(2,4-OPhy) in isopropyl acetate were dissolved HOBt (57 mg, 0.42 mmol) and Fmoc-Ala (1.52 g, 4.62 mmol), EDC HCl (970 mg, 5.06 mmol) was added at 0° C., and the mixture was stirred at room temperature overnight. The reaction mixture was washed three times with 0.1N hydrochloric acid (30 ml), three times with 5% aqueous sodium carbonate solution (30 ml), and once with 20% brine (30 ml) to allow conversion to Fmoc-Ala-Glu(OtBu)-Lys(Boc)-Ser(tBu)-OBzl(2,4-OPhy) in the reaction system, which was used in the subsequent reaction.

Example 30

Synthesis of H-Ala-Glu(OtBu)-Lys(Boc)-Ser(tBu)-OBzl(2,4-OPhy) by removal of Fmoc from Fmoc-Ala-Glu(OtBu)-Lys(Boc)-Ser(tBu)-OBzl(2,4-OPhy)

To a solution (100 ml) of Fmoc-Ala-Glu(OtBu)-Lys(Boc)-Ser(tBu)-OBzl(2,4-OPhy) in isopropyl acetate was added 4-aminomethylpiperidine (1.43 g, 12.5 mmol) at 0° C., and the mixture was stirred at room temperature for 3 hr. The reaction mixture was aerated with carbon dioxide, the resulting carbonate was removed by filtration, and the filtrate was washed three times with 1M aqueous sodium phosphate solution (20 ml) adjusted to pH=6.86, once with 10% aqueous sodium carbonate solution (20 ml), and once with 20% brine (20 ml) and concentrated to give H-Ala-Glu(OtBu)-Lys(Boc)-Ser(tBu)-OBzl(2,4-OPhy) as an oil.

Example 31

Synthesis of H-Ala-Glu-Lys-Ser-OH 2TFA salt by deprotection of H-Ala-Glu(OtBu)-Lys(Boc)-Ser(tBu)-OBzl(2,4-OPhy)

1/20 of the total weight of H-Ala-Glu(OtBu)-Lys(Boc)-Ser(tBu)-OBzl(2,4-OPhy) oil obtained in Example 30 was dissolved in chloroform (10 ml), concentrated and the residual isopropyl acetate was evaporated. Then, deprotection was performed under ice-cooling in a solution of trifluoroacetic acid (TFA):$H_2O$:triisopropylsilane (95:2.5:2.5). After completion of the reaction, the reaction mixture was concentrated. To the residue was added diethyl ether (5 ml) and the mixture was stirred. The precipitate was filtered and dried to give H-Ala-Glu-Lys-Ser-OH 2TFA salt (101 mg). This corresponds to yield 71% (vs. HOBzl(2,4-OPhy)) in the total 9 steps.

ESIMS $MH^+$ 434.0

Example 32

Synthesis of Boc-Cys(Acm)-NH-Dpm(COP) by Condensation of 1-[(2-chloro-5-(2',3'-dihydrophytyloxy)phenyl)]-1-phenylmethanamine (Hereinafter to be Abbreviated as $NH_2$-Dpm(COP)) and Boc-Cys(Acm)-OH $NH_2$-Dpm(COP) (950 mg, 1.85 mmol) obtained in Example 3 was dissolved in isopropyl acetate (20 ml), and washed with 10% aqueous sodium carbonate solution, and 20% brine. To the organic layer were added Boc-Cys(Acm)-OH (594 mg, 2.03 mmol), HOBt (27 mg, 0.20 mmol) at room temperature, and EDC HCl (428 mg, 2.24 mmol) in an ice bath, and the mixture was stirred at room temperature for 3 hr. Dimethylpropanediamine (46 µl, 0.37 mmol) was added and the mixture was stirred for 10 min. The reaction mixture was washed twice with 5% aqueous sodium hydrogen carbonate solution (20 ml), twice with 0.1N hydrochloric acid (20 ml), and once with 20% brine (20 ml). The organic layer was evaporated under reduced pressure to give Boc-Cys(Acm)-NH-Dpm(COP) as an oil.

Example 33

Synthesis of Boc-Pro-Cys(Acm)-NH-Dpm(COP) by Removal of BOC from Boc-Cys(Acm)-NH-Dpm(COP), and Subsequent Condensation with Boc-Pro-OH Boc-Cys(Acm)-NH-Dpm(COP) (1.85 mmol) obtained in Example 32 was dissolved in isopropyl acetate (20 ml), and methanesulfonic acid (600 µl, 9.2 mmol) was added dropwise in an ice bath. The mixture was warmed to room temperature and stirred for 3 hr. 10% Aqueous sodium carbonate solution (20 ml) was added in an ice bath and the mixture was stirred. The aqueous layer was separated and discarded and the organic layer was washed once with 20% brine (20 ml) to allow conversion to H-Cys(Acm)-NH-Dpm(COP) in the reaction system.

To the above-mentioned reaction mixture containing Cys(Acm)-NH-Dpm(COP) (1.55 mmol) were added at room temperature Boc-Pro-OH (367 mg, 1.70 mmol), HOBt (23 mg, 0.17 mmol), and EDC HCl (360 mg, 1.88 mol) in an ice bath. The mixture was warmed to room temperature and stirred overnight. Dimethylpropanediamine (39 µl, 0.31 mmol) was added and the mixture was stirred for 10 min. The reaction mixture was washed twice with 5% aqueous sodium hydrogen carbonate solution (20 ml), twice with 0.1N hydrochloric acid (20 ml), and once with 20% brine (20 ml). The organic layer was evaporated under reduced pressure to give Boc-Pro-Cys(Acm)-NH-Dpm(COP) as an oil.

Example 34

Synthesis of Boc-Trp(CHO)-Pro-Cys(Acm)-NH-Dpm(COP) by Removal of BOC from Boc-Pro-Cys(Acm)-NH-Dpm(COP), and Subsequent Condensation with Boc-Trp(CHO)—OH Boc-Pro-Cys(Acm)-NH-Dpm(COP) (1.55 mmol) obtained in Example 33 was dissolved in isopropyl acetate (15 ml), and methanesulfonic acid (500 µl, 7.7 mmol) was added dropwise in an ice bath. The mixture was warmed to room temperature and stirred for 3 hr. 10% Aqueous sodium carbonate solution (20 ml) and purified water (10 ml) were added in an ice bath and the mixture was stirred for a while. The aqueous layer was separated and discarded, and the organic layer was washed once with 20% brine (20 ml) to allow conversion to Pro-Cys(Acm)-NH-Dpm(COP) in the reaction system.

To the above-mentioned reaction mixture containing Pro-Cys(Acm)-NH-Dpm(COP) were added Boc-Trp(CHO)—OH (566 mg, 1.69 mmol), HOBt (23 mg, 0.17 mmol) at room temperature, and EDC HCl (360 mg, 1.88 mol) in an ice bath. The mixture was warmed to room temperature and stirred overnight.

Dimethylpropanediamine (39 µl, 0.31 mmol) was added and the mixture was stirred for 10 min. The reaction mixture was washed twice with 5% aqueous sodium hydrogen carbonate solution (20 ml), twice with 0.1N hydrochloric acid (20 ml), and once with 20% brine (20 ml). The organic layer was evaporated under reduced pressure to give Boc-Trp(CHO)-Pro-Cys(Acm)-NH-Dpm(COP) as an oil.

Example 35

Synthesis of Boc-Asp(OBzl)-Trp(CHO)-Pro-Cys(Acm)-NH-Dpm(COP) by Removal of BOC from Boc-Trp(CHO)-Pro-Cys(Acm)-NH-Dpm(COP), and Subsequent Condensation with Boc-Asp(OBzl)-OH Boc-Trp(CHO)-Pro-Cys(Acm)-NH-Dpm(COP) (1.29 mmol) obtained in Example 34 was dissolved in isopropyl acetate (20 ml), methanesulfonic acid (400 µl, 6.2 mmol) was added dropwise in an ice bath and the mixture was stirred at room temperature for 3 hr. Methanesulfonic acid (100 µl, 1.5 mmol) was added, and the mixture was further stirred for 3 hr. Methanesulfonic acid (200 µl, 3.1 mmol) was added, and the mixture was stirred for 2 hr. 10% Aqueous sodium carbonate solution (25 ml) was added in an ice bath, and the mixture was stirred. The aqueous layer was separated and discarded, and the organic layer was washed once with 20% brine (20 ml) to allow conversion to Trp(CHO)-Pro-Cys(Acm)-NH-Dpm(COP) in the reaction system.

To the above-mentioned reaction mixture containing Trp(CHO)-Pro-Cys(Acm)-NH-Dpm(COP) were added at room temperature Boc-Asp(OBzl)-OH (451 mg, 1.39 mmol), HOBt (19 mg, 0.14 mmol), and EDC HCl (297 mg, 1.55 mol) in an ice bath. The mixture was warmed to room temperature and stirred overnight. Dimethylpropanediamine (39 µl, 0.31 mmol) was added and the mixture was stirred for 10 min. The reaction mixture was washed twice with 5% aqueous sodium hydrogen carbonate solution (20 ml), twice with 0.1N hydrochloric acid (20 ml), and once with 20% brine (20 ml). The organic layer was evaporated under reduced pressure to give Boc-Asp(OBzl)-Trp(CHO)-Pro-Cys(Acm)-NH-Dpm(COP) as an oil.

Example 36

Synthesis of Boc-Gly-Asp(OBzl)-Trp(CHO)-Pro-Cys(Acm)-NH-Dpm(COP) by Removal of BOC from Boc-Asp(OBzl)-Trp(CHO)-Pro-Cys(Acm)-NH-Dpm(COP), and Subsequent Condensation with Boc-Gly-OH Boc-Asp(OBzl)-Trp(CHO)-Pro-Cys(Acm)-NH-Dpm(COP) (1.29 mmol) obtained in Example 35 was dissolved in isopropyl acetate (20 ml), methanesulfonic acid (400 µl, 6.2 mmol) was added dropwise in an ice bath and the mixture was stirred at room temperature for 3 hr. Methanesulfonic acid (300 µl, 4.6 mmol) was added, and the mixture was further stirred for 2 hr. 10% Aqueous sodium carbonate solution (25 ml) was added in an ice bath and the mixture was stirred for a while. The aqueous layer was separated and discarded, and the organic layer was washed once with 20% brine (20 ml) to allow conversion to Asp(OBzl)-Trp(CHO)-Pro-Cys(Acm)-NH-Dpm(COP) in the reaction system.

To the above-mentioned reaction mixture containing Asp(OBzl)-Trp(CHO)-Pro-Cys(Acm)-NH-Dpm(COP) were added Boc-Gly-OH (245 mg, 1.40 mmol), HOBt (19 mg, 0.14 mmol) at room temperature, and EDC HCl (297 mg, 1.55 mol) in an ice bath. The mixture was warmed to room temperature and stirred overnight. Dimethylpropanediamine (39 µl, 0.31 mmol) was added and the mixture was stirred for 10 min. The reaction mixture was washed twice with 5% aqueous sodium hydrogen carbonate solution (20 ml), twice with 0.1N hydrochloric acid (20 ml), and once with 20% brine (20 ml). The organic layer was evaporated under reduced pressure to give Boc-Gly-Asp(OBzl)-Trp(CHO)-Pro-Cys(Acm)-NH-Dpm(COP) as an oil.

Example 37

Synthesis of Boc-Leu-OBzl(3-O-GI-1000) by Condensation of Bzl-(3-O-GI-1000)-OH and Boc-Leu-OH

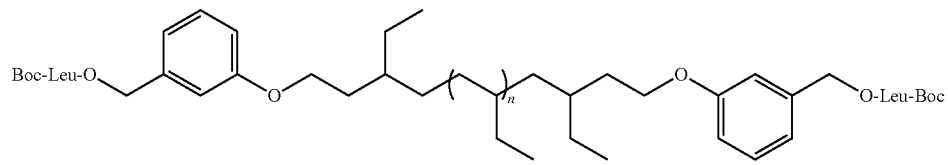

Bzl-(3-O-GI-1000)-OH (450 mg) obtained in Example 19 was dissolved in isopropyl acetate (4 ml), DMAP (13 mg, 0.11 mmol) and Boc-Leu H$_2$O (321 mg, 1.29 mmol) and EDC HCl (270 mg, 1.41 mmol) were added and the mixture was stirred at 40° C. for 6 hr. The reaction mixture was cooled to room temperature, heptane (30 ml) was added, and the mixture was washed 6 times with 90% aqueous acetonitrile solution (15 ml). The solvent of the organic layer was evaporated to give Boc-Leu-OBzl(3-O-GI-1000) (376 mg).

$^1$H-NMR (300 MHz): δ0.86-1.57 (m), 2.01-2.04 (m, 3H), 3.93-3.97 (m, 2H), 4.88 (t, 1H), 5.11 (s, 2H), 6.84-6.91 (m, 3H), 7.23-7.26 (m, 1H).

Example 38

Synthesis of Boc-Tyr(Bzl)-Leu-OBzl(3-O-GI-1000) by Removal of BOC from Boc-Leu-OBzl(3-O-GI-1000), and Subsequent Condensation with Boc-Tyr(Bzl)-OH mmol), Boc-Glu(OBzl)-OH (140 mg, 0.38 mmol) and EDC HCl (79 mg, 0.41 mmol), and the mixture was stirred at 40° C. overnight. To the reaction mixture was added DMPDA (5 μl, 0.04 mmol) to quench the reaction, and the mixture was washed three times with 1N hydrochloric acid. The organic layer was concentrated to give Boc-Glu(OBzl)-Tyr(Bzl)-Leu-OBzl(3-GI-1000) (100 mg).

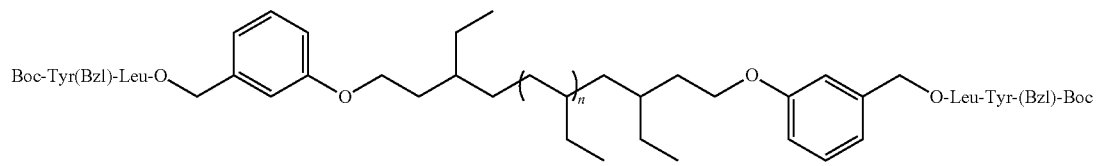

Boc-Leu-OBzl(3-O-GI-1000) (100 mg) obtained in Example 37 was dissolved in isopropyl acetate (1 ml), methanesulfonic acid (32 μl, 0.49 mmol) was added dropwise, and the mixture was stirred for 5 hr. After completion of the reaction, the mixture was washed three times with 10% aqueous sodium carbonate solution, and once with 20% brine to allow conversion to H-Leu-OBzl(3-O-GI-1000) in the reaction system.

To the above-mentioned reaction mixture containing H-Leu-OBzl(3-O-GI-1000) were added HOBt (5 mg, 0.04 mmol), Boc-Tyr(Bzl)-OH (140 mg, 0.38 mmol) and EDC HCl (79 mg, 0.41 mmol) and the mixture was stirred overnight. To the reaction mixture was added N,N-dimethyl-1,3-propanediamine (DMPDA) (5 μl, 0.04 mmol) to quench the reaction, and the mixture was washed three times with 1N hydrochloric acid. The organic layer was concentrated to give Boc-Tyr(Bzl)-Leu-OBzl(3-O-GI-1000) (120 mg).

$^1$H-NMR (300 MHz): δ0.85-1.59 (m), 2.02-2.10 (m, 3H), 2.98-3.12 (m, 2H), 3.93-3.96 (m, 2H), 4.51-4.62 (m, 1H), 4.39-5.09 (m, 5H), 6.87-6.93 (m, 5H), 7.09-7.12 (m, 3H), 7.29-7.43 (m, 5H).

Example 39

Synthesis of Boc-Glu(OBzl)-Tyr(Bzl)-Leu-OBzl(3-O-GI-1000) by Removal of BOC from Boc-Tyr(Bzl)-Leu-OBzl(3-O-GI-1000), and Subsequent Condensation with Boc-Glu(OBzl)-OH

Example 40

Synthesis of Boc-Leu-OBzl(3-O-GI-2000) by Condensation of Bzl(3-O-GI-2000)-OH and Boc-Leu-OH Bzl(3-O-GI-2000)-OH (402 mg) obtained in Example 20 was dissolved in isopropyl acetate (4 ml), DMAP (5 mg, 0.06 mmol), Boc-Leu-OH (151 mg, 0.65 mmol) and EDC HCl (128 mg, 0.70 mmol) were added and the mixture was stirred at 40° C. for 4 hr. The reaction mixture was cooled to room temperature, heptane (30 ml) was added, and the mixture was washed 6 times with 90% aqueous acetonitrile solution (15 ml). The solvent of the organic layer was evaporated to give Boc-Leu-OBzl(3-O-GI-2000) (310 mg).

$^1$H-NMR (300 MHz): δ0.88-1.51 (m), 2.01-2.04 (m, 3H), 3.93-3.99 (m, 2H), 4.88-4.90 (m, 1H), 5.13 (s, 2H), 6.84-6.91 (m, 3H), 7.23-7.24 (m, 1H).

Example 41

Synthesis of Boc-Tyr(Bzl)-Leu-OBzl(3-O-GI-2000) by Removal of BOC from Boc-Leu-OBzl(3-O-GI-2000), and Subsequent Condensation with Boc-Tyr(Bzl)-OH Boc-Leu-OBzl(3-O-GI-2000) (100 mg) obtained in Example 40 was dissolved in isopropyl acetate (1 ml), methanesulfonic acid (16 μl, 0.25 mmol) was added drop-

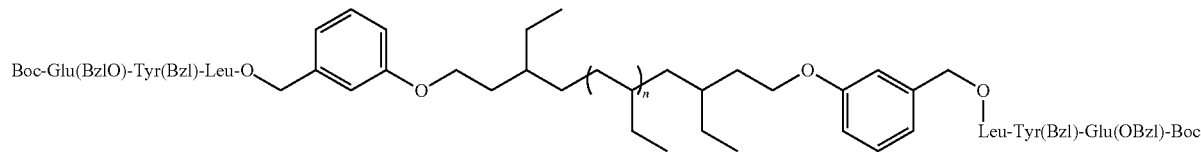

Boc-Tyr(Bzl)-Leu-OBzl(3-O-GI-1000)(100 mg) obtained in Example 38 was dissolved in isopropyl acetate (1 ml), methanesulfonic acid (32 μl, 0.49 mmol) was added dropwise, and the mixture was stirred for 6 hr. After completion of the reaction, the mixture was washed three times with 10% aqueous sodium carbonate solution, and once with 20% brine. To the organic layer were added HOBt (5 mg, 0.04 wise and the mixture was stirred for 3 hr. After completion of the reaction, the mixture was washed three times with 10% aqueous sodium carbonate solution, and once with 20% brine. To this organic layer were added HOBt (3 mg, 0.02 mmol), Boc-Tyr(Bzl)-OH (70 mg, 0.19 mmol) and EDC HCl (40 mg, 0.20 mmol), and the mixture was stirred at 40° C. overnight. To the reaction mixture was added DMPDA (5

μl, 0.04 mmol) to quench the reaction, and the mixture was washed three times with 1N hydrochloric acid. The organic layer was concentrated to give Boc-Tyr(Bzl)-Leu-OBzl(3-O-GI-2000) (120 mg).

$^1$H-NMR (300 MHz): δ0.85-1.59 (m), 2.04-2.10 (m, 3H), 2.99-3.15 (m, 2H), 3.92-3.99 (m, 2H), 4.50-4.63 (m, 1H), 4.41-5.08 (m, 5H), 6.86-6.95 (m, 5H), 7.09-7.15 (m, 3H), 7.27-7.44 (m, 5H)

Example 42

Synthesis of Boc-Glu(OBzl)-Tyr(Bzl)-Leu-OBzl(3-O-GI-2000) by Removal of BOC from Boc-Tyr(Bzl)-Leu-OBzl(3-O-GI-2000), and Subsequent Condensation with Boc-Glu(OBzl)-OH Boc-Tyr(Bzl)-Leu-OBzl(3-O-GI-2000)(100 mg) was dissolved in isopropyl acetate (1 ml), methanesulfonic acid (32 μl, 0.49 mmol) was added dropwise and the mixture was stirred for 6 hr. After completion of the reaction, the mixture was washed three times with 10% aqueous sodium carbonate solution, and once with 20% brine. To this organic layer were added HOBt (5 mg, 0.04 mmol), Boc-Glu(OBzl)-OH (140 mg, 0.38 mmol) and EDC HCl (79 mg, 0.41 mmol) and the mixture was stirred at 40° C. overnight. To the reaction mixture was added DMPDA (5 μl, 0.04 mmol) to quench the reaction, and the mixture was washed three times with 1N hydrochloric acid. The organic layer was concentrated to give Boc-Glu(OBzl)-Tyr(Bzl)-Leu-OBzl(3-O-GI-2000) (100 mg).

Example 43

Synthesis of Fmoc-Leu-OBzl(3,4,5-OPhy) by Condensation of 3,4,5-tri(2',3'-dihydrophytyloxy)benzyl alcohol and Fmoc-Leu-OH, and Subsequent Synthesis of H-Leu-OBzl(3,4,5-OPhy) by Removal of Fmoc 3,4,5-Tri(2',3'-dihydrophytyloxy)benzyl alcohol (5 g, 5.01 mmol) was dissolved in cyclopentylmethylether (CPME)(50 ml), Fmoc-Leu-OH (1.95 g, 5.52 mmol) was added. Thereto were added, in an ice bath, EDC HCl (1.16 g, 6.05 mmol) and DMAP (61 mg, 0.50 mmol), and the mixture was stirred at room temperature for 3 hr. Chloroform (50 ml) was added, and the mixture was stirred at room temperature overnight. After completion of the reaction, the solvent in the reaction mixture was evaporated under reduced pressure to 25 ml, and CPME (50 ml) was added to the residue. The solvent in the reaction mixture was evaporated under reduced pressure to 25 ml again, and CPME (25 ml) was added to the residue to adjust the amount of the solvent in the reaction mixture to 50 ml. The reaction mixture was bubbled with nitrogen for 5 min, diethylenetriamine (2.71 ml, 25.1 mmol) was added in an ice bath under a nitrogen atmosphere, and the mixture was stirred at room temperature for 5 hr. After completion of the reaction, the reaction mixture was washed twice with 10% aqueous sodium carbonate solution (50 ml) to allow liquid-separation, and 20% brine (50 ml) was added to the obtained organic layer. While stirring the organic layer and the aqueous layer (20% brine), 1N hydrochloric acid was added dropwise until the pH of the aqueous layer became 6.8, the organic layer and the aqueous layer were transferred to a separating funnel and the aqueous layer was removed. A similar operation was performed again, the organic layer was washed with stirring with the aqueous layer (20% brine, pH=6.8), and the aqueous layer was removed. The obtained organic layer was washed once with 20% brine (50 ml), once with 10% aqueous sodium carbonate solution (50 ml), and once with 20% brine (50 ml). The obtained organic layer was dried over sodium sulfate, and sodium sulfate was removed by filtration to give a solution (50 ml) of H-Leu-OBzl(3,4,5-OPhy) (5.01 mmol) in CPME.

Example 44

Synthesis of Fmoc-Tyr(tBu)-Leu-OBzl(3,4,5-OPhy) by Condensation of H-Leu-OBzl(3,4,5-OPhy) and Fmoc-Tyr(tBu)-OH, and Subsequent Synthesis of H-Tyr(tBu)-Leu-OBzl(3,4,5-OPhy) by Removal of Fmoc To a solution (50 ml) of H-Leu-OBzl(3,4,5-OPhy) (5.01 mmol) in CPME were added HOBt (68 mg, 0.50 mmol) and Emoc-Tyr(tBu)-OH (2.53 g, 5.52 mmol). Thereto was added EDC HCl (1.16 g, 6.05 mmol) in an ice bath, and the mixture was stirred at room temperature overnight. After completion of the reaction, the solvent in the reaction mixture was evaporated under reduced pressure to 25 ml, and CPME (50 ml) was added to the residue. The solvent in the reaction mixture was evaporated under reduced pressure to 25 ml again, and CPME (25 ml) was added to the residue to adjust the amount of the solvent in the reaction mixture to 50 ml. The reaction mixture was bubbled with nitrogen for 5 min, diethylenetriamine (2.71 ml, 25.1 mmol) was added in an ice bath under a nitrogen atmosphere, and the mixture was stirred at room temperature for 1.5 hr. After completion of the reaction, the reaction mixture was washed twice with 10% aqueous sodium carbonate solution (50 ml), and 20% brine (50 ml) was added to the obtained organic layer. While stirring the organic layer and the aqueous layer (20% brine), 1N hydrochloric acid was added dropwise until the pH of the aqueous layer became 6.8, the organic layer and the aqueous layer were transferred to a separating funnel and the aqueous layer was removed. A similar operation was performed again, the organic layer was washed with stirring with the aqueous layer (20% brine, pH=6.7), and the aqueous layer was removed. The obtained organic layer was washed once with 20% brine (50 ml), once with 10% aqueous sodium carbonate solution (50 ml), and once with 20% brine (50 ml). The obtained organic layer was dried over sodium sulfate, and sodium sulfate was removed by filtration to give a solution (50 ml) of H-Tyr(tBu)-Leu-OBzl(3,4,5-OPhy) (5.01 mmol) in CPME.

Example 45

Synthesis of Fmoc-Glu(OtBu)-Tyr(tBu)-Leu-OBzl(3,4,5-OPhy) by Condensation of H-Tyr(tBu)-Leu-OBzl(3,4,5-OPhy) and Fmoc-Glu(OtBu)-OH, and Subsequent Synthesis of H-Glu(OtBu)-Tyr(tBu)-Leu-OBzl(3,4,5-OPhy) by Removal of Fmoc To a solution (50 ml) of H-Tyr(tBu)-Leu-OBzl(3,4,5-OPhy) (5.01 mmol) in CPME were added HOBt (68 mg, 0.50 mmol) and Fmoc-Glu(OtBu)-OH (2.35 g, 5.52 mmol). Thereto was added EDC HCl (1.16 g, 6.05 mmol) in an ice bath, and the mixture was stirred at room temperature overnight. After completion of the reaction, the solvent in the reaction mixture was evaporated under reduced pressure to 25 ml, and CPME (50 ml) was added to the residue. The solvent in the reaction mixture was evaporated under reduced pressure to 25 ml again, and CPME (25 ml) was added to the residue to adjust the amount of the solvent in the reaction mixture to 50 ml. A small amount of the reaction mixture was added to trifluoroacetic acid (TFA)/H$_2$O/triisopropylsilane solution for deprotection and analyzed by LC/MS, whereby ESIMS MH$^+$ 646.2 of Fmoc-Glu-Tyr-Leu-OH was confirmed.

The aforementioned reaction mixture was bubbled with nitrogen for 5 min, diethylenetriamine (2.71 ml, 25.1 mmol) was added in an ice bath under a nitrogen atmosphere, and the mixture was stirred at room temperature for 2 hr. After completion of the reaction, the reaction mixture was washed twice with 10% aqueous sodium carbonate solution (50 ml), and 20% brine (50 ml) was added to the obtained organic layer. While stirring the organic layer and the aqueous layer (20% brine), 1N hydrochloric acid was added dropwise until the pH of the aqueous layer became 6.8, the organic layer and the aqueous layer were transferred to a separating funnel and the aqueous layer was removed. A similar operation was performed again, the organic layer was washed with stirring with the aqueous layer (20% brine, pH=6.0), and the aqueous layer was removed. The obtained organic layer was washed once with 10% aqueous sodium carbonate solution (50 ml), and once with 20% brine (50 ml). The obtained organic layer was dried over sodium sulfate, sodium sulfate was removed by filtration and the solvent of the organic layer was evaporated under reduced pressure to give a solution (50 ml) of H-Glu(OtBu)-Tyr(tBu)-Leu-OBzl(3,4,5-OPhy) (5.01 mmol) in CPME.

Example 46

Synthesis of Fmoc-Glu(OtBu)-Glu(OtBu)-Tyr(tBu)-Leu-OBzl(3,4,5-OPhy) by Condensation of H-Glu(OtBu)-Tyr(tBu)-Leu-OBzl(3,4,5-OPhy) and Fmoc-Glu(OtBu)-OH, and Subsequent Synthesis of H-Glu(OtBu)-Glu(OtBu)-Tyr(tBu)-Leu-OBzl(3,4,5-OPhy) by Removal of Fmoc To a solution (50 ml) of H-Glu(OtBu)-Tyr(tBu)-Leu-OBzl(3,4,5-OPhy) (5.01 mmol) in CPME were added HOBt (68 mg, 0.50 mmol) and Fmoc-Glu(OtBu)-OH (2.35 g, 5.52 mmol). Thereto was added EDC HCl (1.16 g, 6.05 mmol) in an ice bath, and the mixture was stirred at room temperature overnight. After completion of the reaction, the solvent in the reaction mixture was evaporated under reduced pressure to 35 ml, and CPME (50 ml) was added to the residue. The solvent in the reaction mixture was evaporated under reduced pressure to 30 ml again, and CPME (25 ml) was added to the residue to adjust the amount of the solvent in the reaction mixture to 55 ml. A small amount of the reaction mixture was taken, deprotected and analyzed, whereby ESIMS MH$^+$ 775.2 of Fmoc-Glu-Glu-Tyr-Leu-OH was confirmed.

The aforementioned reaction mixture was bubbled with nitrogen for 5 min, diethylenetriamine (2.71 ml, 25.1 mmol) was added in an ice bath under a nitrogen atmosphere, and the mixture was stirred at room temperature for 1.5 hr. After completion of the reaction, the reaction mixture was washed twice with 10% aqueous sodium carbonate solution (50 ml), and 20% brine (50 ml) was added to the obtained organic layer. While stirring the organic layer and the aqueous layer (20% brine), 1N hydrochloric acid was added dropwise until the pH of the aqueous layer became 6.8, the organic layer and the aqueous layer were transferred to a separating funnel and the aqueous layer was removed. A similar operation was performed again, the organic layer was washed with stirring with the aqueous layer (20% brine, pH=6.7), and the aqueous layer was removed. The obtained organic layer was washed once with 20% brine (50 ml), once with 10% aqueous sodium carbonate solution (50 ml), and once with 20% brine (50 ml). The obtained organic layer was dried over sodium sulfate, and sodium sulfate was removed by filtration to give a solution (55 ml) of H-Glu(OtBu)-Glu(OtBu)-Tyr(tBu)-Leu-OBzl(3,4,5-OPhy) (5.01 mmol) in CPME.

Example 47

Synthesis of H-Asp(OtBu)-Phe-Glu(OtBu)-Glu(OtBu)-Ile-Pro-Glu(OtBu)-Glu(OtBu)-Tyr(tBu)-Leu-OBzl(3,4,5-OPhy)

Using H-Glu(OtBu)-Glu(OtBu)-Tyr(tBu)-Leu-OBzl(3,4,5-OPhy) and the following protected amino acids: Emoc-Pro, Fmoc-Ile, Fmoc-Glu(OtBu), Fmoc-Glu(OtBu), Fmoc-Phe and Fmoc-Asp(OtBu) in this order and by operations similar to those in Examples 43-46, condensation reaction, deprotection and work-up operation were repeated to elongate the peptide chain, and the resultant product was precipitated from aqueous acetonitrile solution to give H-Asp(OtBu)-Phe-Glu(OtBu)-Glu(OtBu)-Ile-Pro-Glu(OtBu)-Glu(OtBu)-Tyr(tBu)-Leu-OBzl(3,4,5-OPhy) (10.8 g, 4.15 mmol, yield 82% vs. 3,4,5-tri(2',3'-dihydrophytyloxy)benzyl alcohol, ESIMS MH$^+$ 2598.5).

A small amount of this compound was taken, deprotected with trifluoroacetic acid (TFA) and analyzed, whereby ESIMS MH$^+$ 1283.5 of H-Asp-Phe-Glu-Glu-Ile-Pro-Glu-Glu-Tyr-Leu-OH was confirmed.

Comparative Experimental Example

Solubility (20° C.) of Branched Chain-Containing Aromatic Compound of the Present Invention and Straight Chain-Containing Aromatic Compound in Various Solvents Experiment Method The branched chain-containing aromatic compounds (compounds of Examples 4, 5, 19, 20 and 21) of the present invention and straight chain-containing aromatic compounds (Comparative Examples 1-3) as Comparative Examples were saturated in solvents at 20° C., and the solubility (unit: wt %) was measured (Tables 1, 2).

TABLE 1

| solvent | Example 4 | Example 5 | Example 19 | Example 20 | Example 21 |
|---|---|---|---|---|---|
| isopropyl acetate | >25 | >50 | — | >25 | — |
| ethyl acetate | >25 | >50 | >25 | — | >50 |
| CPME | >50 | >50 | >25 | >50 | >50 |
| toluene | — | >50 | — | >50 | — |
| chloroform | >50 | >50 | >50 | >50 | >50 |

TABLE 2

| | Comparative Example 1 (straight chain $C_{18}H_{37}$) | Comparative Example 2 (straight chain $C_{22}H_{45}$) | Comparative Example 3 (straight chain $C_{22}H_{45}$) |
|---|---|---|---|
| solvent | 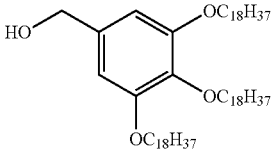 | 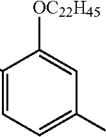 | 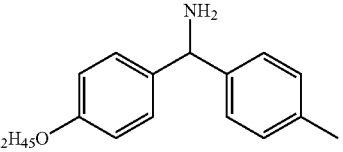 |
| isopropyl acetate | 0.02 | 0.06 | 0.1 |
| ethyl acetate | 0.2 | 0.3 | 0.2 |
| CPME | 4.5 | — | 0.01 |
| toluene | 2.6 | — | 0.01 |
| chloroform | 9.9 | — | 0.8 |

Experiment Results

Any of the compounds of the present invention (i.e., particular branched chain-containing aromatic compound organic groups having at least one aliphatic hydrocarbon group having one or more branched chains, a total number of the branched chain of not less than 3 and a total carbon number of not less than 14 and not more than 300) showed strikingly high solubility not only in isopropyl acetate and ethyl acetate, but also various organic solvents, as compared to Comparative Example compounds 1-3 wherein the corresponding organic group is a straight chain and mostly showed 10- to 1000-fold or more, in some cases 5000-fold or more, higher solubility (see Tables 1, 2). Therefrom it has been found that the compound of the present invention can function as a superior protecting reagent for amino acid and/or peptide in production methods of peptides.

INDUSTRIAL APPLICABILITY

Using the particular branched chain-containing aromatic compound of the present invention, which is easily-soluble in isopropyl acetate superior in liquid-separation operability, a production method of peptide and the like, which provides a final product simply by extraction separation, without crystallization and isolation of each intermediate in each step, can be provided. Moreover, organic synthesis reactions and practical industrial processes can also be provided.

Also, in the production method of peptide of the present invention, peptide can be stably dissolved in solvents irrespective of the sequence and chain length thereof. Therefore, the method is advantageous in that it can simplify isolation and purification steps, and comprehensively ensure high purity and high yield as compared to conventional liquid phase methods.

The invention claimed is:
1. A branched chain-containing aromatic compound adduct which has a carboxyl group,
   wherein
   said carboxyl group is protected by a branched chain-containing aromatic compound selected from the group consisting of:
   2,4-di(2',3'-dihydrophytyloxy)benzyl alcohol;
   3,5-di(2',3'-dihydrophytyloxy)benzyl alcohol;
   4-(2',3'-dihydrophytyloxy)benzyl alcohol;
   1-[(2-chloro-5-(2',3'-dihydrophytyloxy)phenyl)]-1-phenylmethanamine;
   3,4,5-tri(2',3'-dihydrophytyloxy)benzyl alcohol;
   3,4,5-tri(2',3'-dihydrophytyloxy)benzylamine;
   4-(2',3'-dihydrophytyloxy)benzylamine;
   2-[3',4',5'-tri(2'',3''-dihydrophytyloxy)benzyloxy]-4-methoxybenzyl alcohol;
   4-(2',3'-dihydrophytyloxy)-2-methoxybenzyl alcohol;
   4-(2',3'-dihydrophytyloxy)-2-methoxybenzylamine;
   4-(2',3'-dihydrophytyloxy)-2-methylbenzyl alcohol;
   4-(2',3'-dihydrophytyloxy)-2-methylbenzylamine;
   2,2,4,8,10,10-hexamethyl-5-dodecanoic acid (4-hydroxymethyl)phenylamide;
   4-(3,7,11-trimethyldodecyloxy)benzyl alcohol;
   2-(3,7,11-trimethyldodecyloxy)-9-phenylfluoren-9-ol;
   a compound represented by the formula:

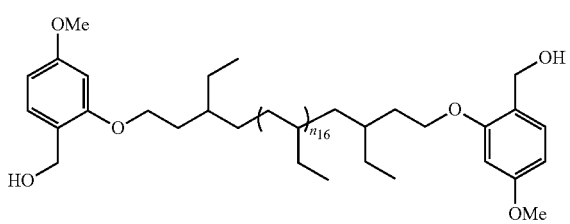

wherein $n_{16}$ is 23 or 34;
   a compound represented by the formula:

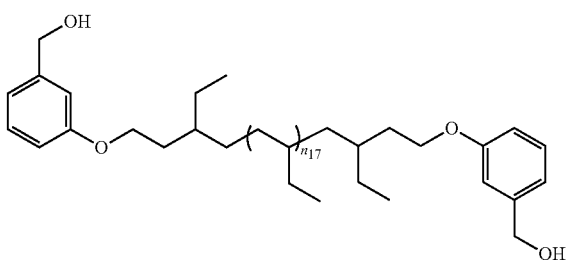

wherein $n_{17}$ is 23 or 34;
a compound represented by the formula:
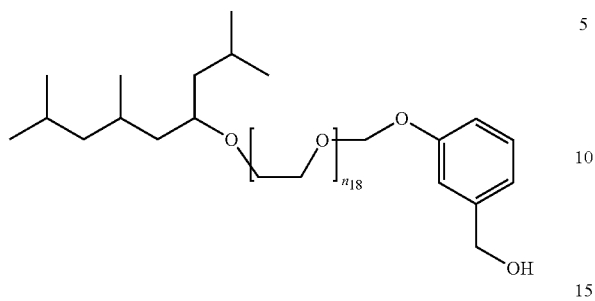
wherein $n_{18}$ is 5 to 7; and
a compound represented by the formula:
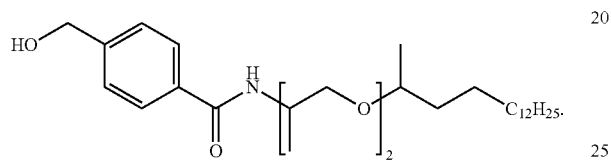
* * * * *